United States Patent
Tawara et al.

(10) Patent No.: US 7,262,278 B2
(45) Date of Patent: Aug. 28, 2007

(54) ANTI-HLA-DR ANTIBODY

(75) Inventors: Tomonori Tawara, Takasaki (JP); Shiro Kataoka, Takasaki (JP)

(73) Assignee: Kirin Beer Kabushiki Kaisha, Tokyo (JP)

(*) Notice: Subject to any disclaimer, the term of this patent is extended or adjusted under 35 U.S.C. 154(b) by 609 days.

(21) Appl. No.: 10/469,304

(22) PCT Filed: Oct. 15, 2002

(86) PCT No.: PCT/JP02/10665

§ 371 (c)(1),
(2), (4) Date: Aug. 29, 2003

(87) PCT Pub. No.: WO03/033538

PCT Pub. Date: Apr. 24, 2003

(65) Prior Publication Data

US 2004/0091974 A1 May 13, 2004

(30) Foreign Application Priority Data

Oct. 15, 2001 (JP) .............................. 2001-317054

(51) Int. Cl.
*C12P 21/08* (2006.01)
*C07K 16/28* (2006.01)
(52) U.S. Cl. .............................. 530/388.7; 530/388.2; 530/388.73
(58) Field of Classification Search ............. 530/388.2, 530/388.7, 388.73, 387.1, 387.3
See application file for complete search history.

(56) References Cited

U.S. PATENT DOCUMENTS

| 6,416,958 B2 | 7/2002 | Vidovic et al. |
| 2001/0053360 A1 | 12/2001 | Vidovic et al. |

FOREIGN PATENT DOCUMENTS

| WO | WO94/29351 | 12/1994 |
| WO | WO96/17874 | 6/1996 |
| WO | WO 01/87337 A1 | 11/2001 |
| WO | WO 01/87338 A1 | 11/2001 |
| WO | WO 02/088186 A1 | 11/2002 |

OTHER PUBLICATIONS

S. A. Kostelny et al., "Humanization and Characterization of the ANTI-HLA-DR Antibody 1D10", *Int. J. Cancer*, Aug. 2001, vol. 93, No. 4, pp. 556-565.
H. L. Niman et al., "Generation of Protein-Reactive Antibodies by Short Peptides is an Event of High Frequency: Implications for the Structural basis of Immune Recognition", *Proc. Natl. Acad. Sci. USA*, Aug. 1983, vol. 80, No. 16, pp. 4949-4953.
R. G. Ulrich et al., "Immune Recognition of Human Major Histocompatibility Antigens: Localization by a Comprehensive Synthetic Strategy of the Continuous Antigenic sites in the First Domain of HLA-DR2 β Chain", *Eur. J. Immunol.*, 1987, vol. 17, No. 4, pp. 497-502.
Johannes Stöckel et al., "Refolding of Human Class II Major Histocompatibility Complex Molecules Isolated from *Escherichia coli*"The Journal of Biological Chemistry, vol. 269, No. 47, Nov. 1994, pp. 29571-29578.
C.B. Lock et al., "MHC class II sequences of an HLA-DR2 narcoleptic", Immunogenetics 27: pp. 449-455, 1988.
Peter McLaughlin et al., "Rituximab Chimeric Anti-CD20 Monoclonal Antibody Therapy for Relapsed Indolent Lymphoma: Half of Patients Respond to a Four Dose Treatment Program", Journal of Clinical Oncology, vol. 16, No. 8 (Aug.), 1998: pp. 2825-2833.
B. Colffier et al., "Rituximab (Anti-CD20 Monoclonal Antibody) for the Treatment of Patients With Relapsing of Refractory Aggressive Lymphoma: A Multicenter Phase II Study", Blood, vol. 92, No. 6, 1998, pp. 1927-1932.
Constantin N. Baxevanis et al., "Genetic Control of T-Cell Proliferative Responses to Poly (Glu$^{40}$Ala$^{60}$) and Poly (Glu$^{51}$Lys$^{34}$Tyr$^{15}$): Subregion-Specific Inhibition of the Responses with Monoclonal Ia Antibodies." Immunogenetics 11, 1980, pp. 617-628.
James T. Rosenbaum et al., "In Vivo Effects of Antibodies to Immune Response Gene Products I. Haplotype-specific Suppression of Humoral Immune Responses with a Monoclonal Anti-I-A", J. Exp. Med., vol. 154, 1981, pp. 1694-1702.
Matthew K. Waldor et al., "In vivo therapy with monoclonal anti-I-A Antibody suppresses immune responses to acetylcholine receptor", Proc. Natl. Acad. Sci. USA, vol. 80, (1983), pp. 2713-2717.
Margreet Jonker et al., "Successful Treatment of EAE in Rhesus Monkeys with MHC Class II Specific Monoclonal Antibodies", Journal of Autoimmunity (1988), 1, pp. 399-414.
H.P.J.D. Stevens et al., "In Vivo Immunosuppressive Effects of Monoclonal Antibodies Specific for CD3+, CD4+, CD8+, and MHC Class II Positive Cells", Transplantation Proceedings, vol. 22, No. 4, 1990, pp. 1783-1784.
R. Billing et al., "Prolongation of Skin Allograft Survival in Monkeys Treated with Anti-Ia and Anti-Blast/Monocyte Monoclonal Antibodies", Transplantation Proceedings, vol. XV, No. 1, (1983), pp. 649-650.
M. Jonker et al., "Complications of Monoclonal Antibody (MAb) Therapy: The Importance of Primate Studies", Transplantation Proceedings, vol. 23, No. 1, (1991), pp. 264-265.

(Continued)

Primary Examiner—Christina Chan
Assistant Examiner—F. Pierre VanderVegt
(74) Attorney, Agent, or Firm—Foley & Lardner LLP

(57) ABSTRACT

This invention provides an anti-HLA-DR monoclonal antibody. This invention relates to an antibody binding to HLA-DR or a functional fragment thereof having (a) life-extending effects in nonhuman animals bearing HLA-DR-expressing cancer cells and (b) activity of suppressing immune responses lower than that of L243, or an antibody binding to HLA-DR or a functional fragment thereof exhibiting immunosuppressive activity equivalent to or higher than that of the mouse anti-HLA-DR monoclonal antibody L243 (ATCC HB-55).

21 Claims, 13 Drawing Sheets

OTHER PUBLICATIONS

Sheri A. Kostelny et al., "Humanization and Characterization of the ANTI-HLA-DR Antibody 1D10", Int. J. Cancer, 93, (2001), pp. 556-565.

Supplementary Partial European Search Report of EP 02 80 1565.

Alberto Chersi et al., "Immunologic and Funcitonal Characterization of ANTI-HLA-DR Rabbit Antibodies Induced by Synthetic Peptides", Molecular Immunology, vol. 21, No. 10, pp. 847-852, 1984.

R.J.T. Hancock et al., "MicroElisa assays of anti-HLA activity and isotype of human monoclonal antibodies", Tissue Antigens (1989), 33, pp. 437-444.

D. Löffler et al., "Recognition of HLA-DR1/DRB1 *0101 molecules presenting HLA-A2 derived peptides by a human recombinant antibody, Fab-4 A1", Erop. J. Immunogenet., vol. 25, 1998, pp. 339-347.

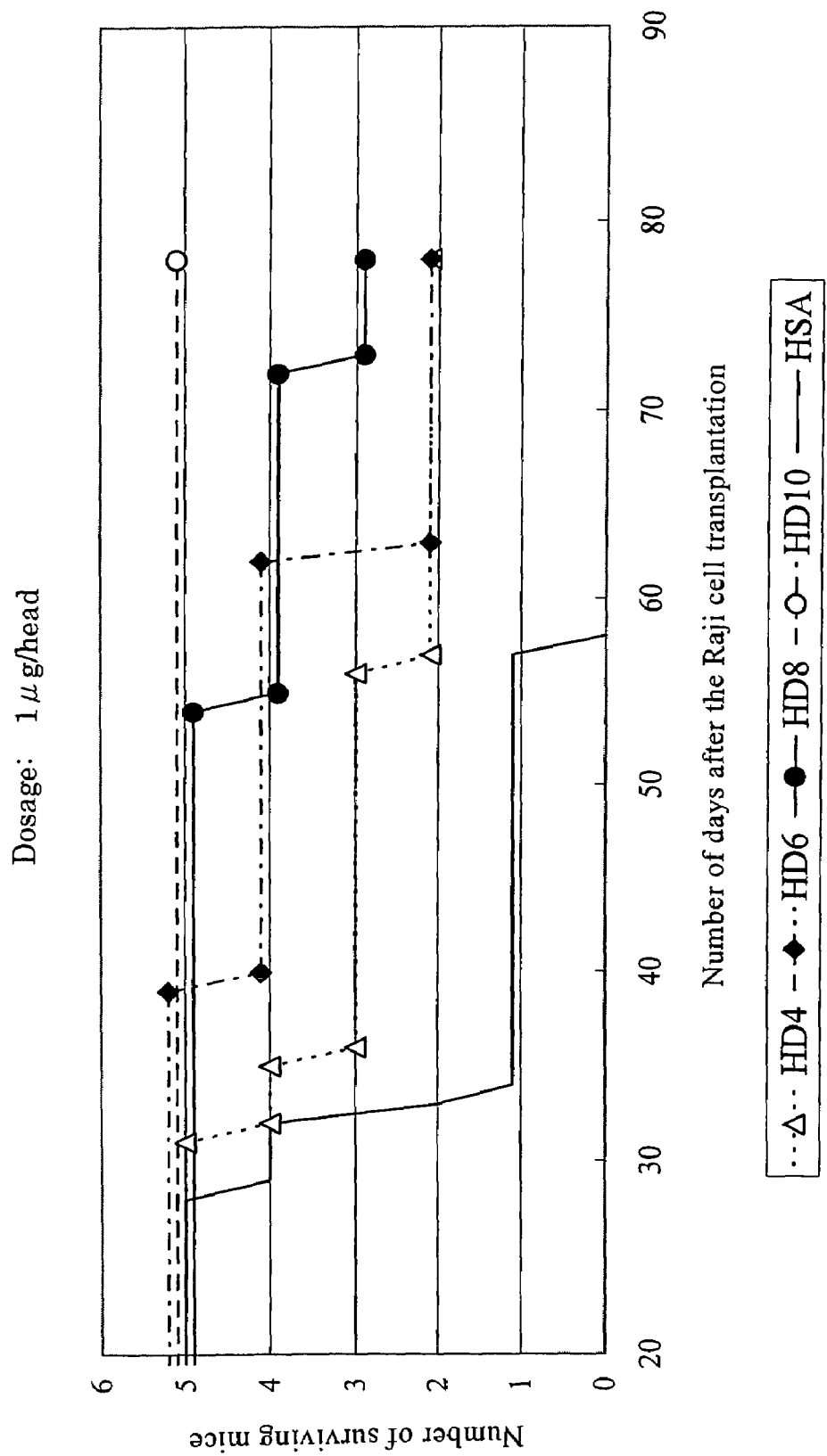

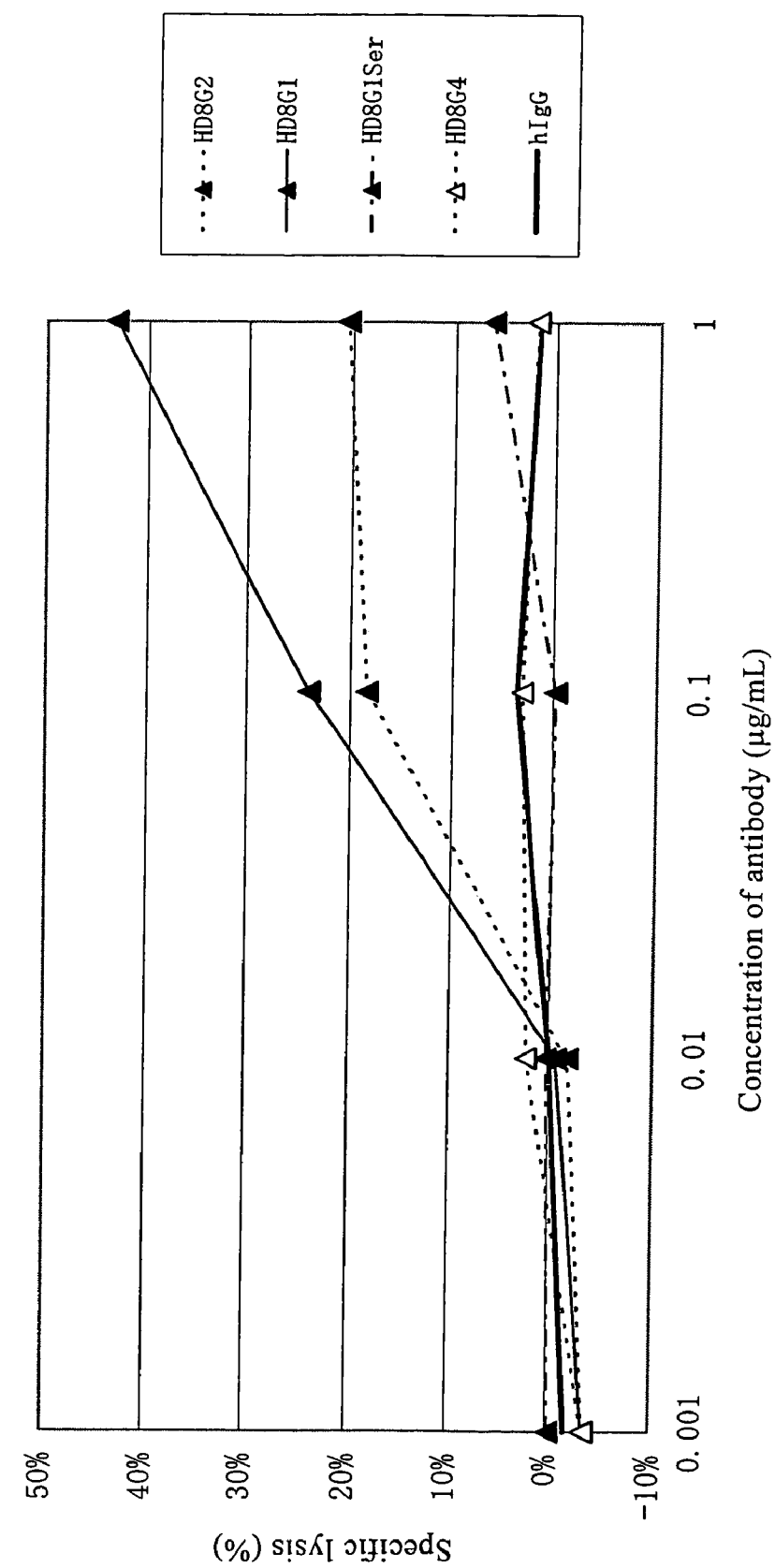

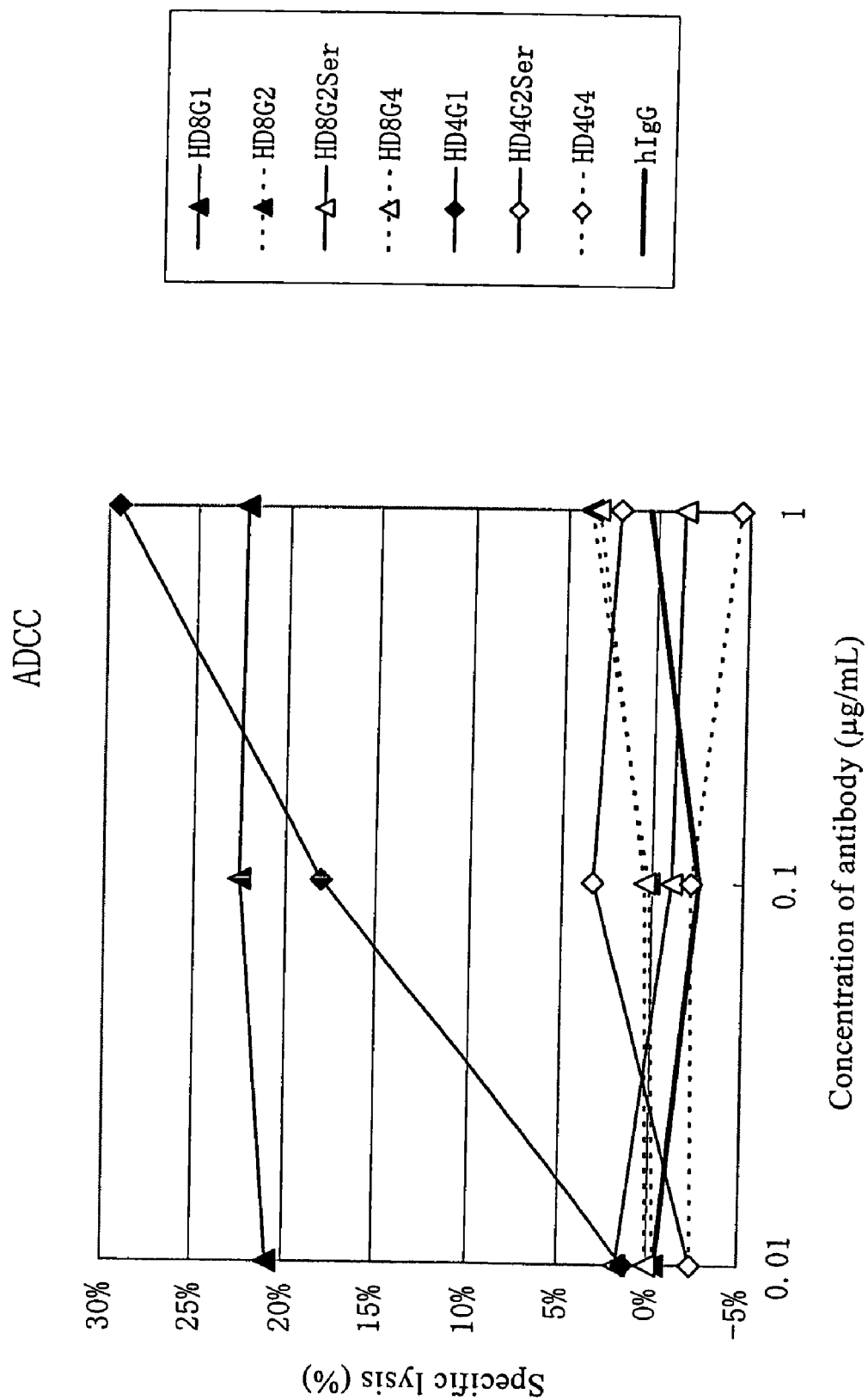

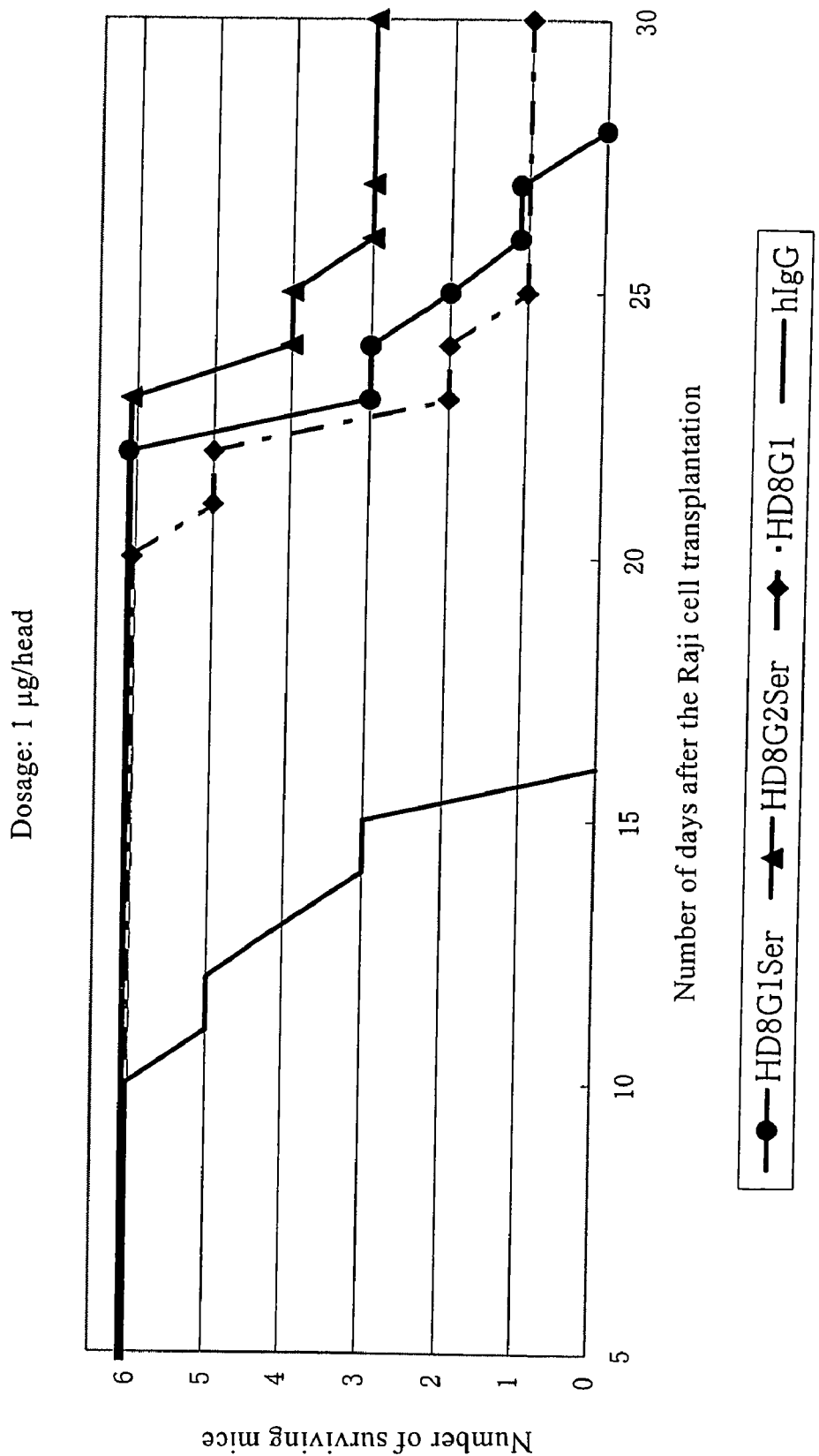

Fig. 6

| SEQ ID NO | 61 | 62 | 63 | 64 | 65 | 66 | 67 | 68 | 69 | 70 | 71 | 72 | 73 | HD4 | HD6 | HD8 |
|---|---|---|---|---|---|---|---|---|---|---|---|---|---|---|---|---|
| 24 | W | N | S | Q | K | D | F | L | E | D | R | R | A | ++++ | +++ | +++ |
| 25 | W | N | S | Q | K | D | F | L | E | R | R | R | A | ++ | ++++ | ++++ |
| 26 | W | N | S | Q | K | D | F | L | E | D | E | R | A | ++++ | − | +++ |
| 27 | W | N | S | Q | K | D | F | L | E | Q | A | R | A | ++++ | ++ | ++++ |
| 28 | W | N | S | Q | K | D | I | L | E | D | E | R | A | +++ | − | ++++ |
| 29 | W | N | S | Q | K | D | I | L | E | Q | K | R | G | +/− | + | ++++ |
| 30 | W | N | S | Q | K | D | I | L | E | D | R | R | A | + | +/− | ++++ |
| 31 | W | N | S | Q | K | D | I | L | E | D | R | R | G | +/− | − | ++++ |
| 32 | W | N | S | Q | K | D | I | L | E | D | K | R | A | +/− | − | ++++ |
| 33 | W | N | S | Q | K | D | I | L | E | Q | A | R | A | +++ | +/− | ++++ |
| 34 | W | N | S | Q | K | D | L | L | E | Q | R | R | A | ++ | +++ | ++++ |
| 35 | W | N | S | Q | K | D | L | L | E | Q | A | R | A | ++++ | − | ++++ |
| 36 | W | N | S | Q | K | D | L | L | E | Q | K | R | G | + | + | +++ |
| 37 | W | N | S | Q | K | D | L | L | E | D | R | R | A | +++ | +/− | ++++ |
| 38 | W | N | S | Q | K | D | L | L | E | R | R | R | A | ++ | ++++ | ++++ |
| 39 | W | N | S | Q | K | D | L | L | E | D | E | R | A | +++ | − | +++ |
| 40 | W | N | S | Q | K | D | A | L | E | Q | R | R | A | + | +++ | ++++ |
| 41 | W | N | S | Q | K | D | L | L | E | A | R | R | A | ++++ | ++++ | ++++ |
| 42 | W | N | S | Q | K | D | L | L | E | Q | A | R | A | +++ | ++ | ++++ |
| 43 | W | N | S | Q | K | D | L | L | E | Q | R | R | G | + | +++ | +++ |
| 48 | W | N | S | Q | A | D | L | L | E | Q | R | R | A | − | +/− | +/− |
| 49 | W | N | S | Q | K | A | L | L | E | Q | R | R | A | − | ++ | +/− |
| 50 | W | N | S | Q | K | D | L | A | Q | R | R | A | | − | ++ | − |
| 51 | W | N | S | Q | K | D | L | L | E | Q | R | A | A | − | +/− | − |
| 44 | A | N | S | Q | K | D | L | L | E | Q | R | R | A | +/− | +++ | ++++ |
| 45 | W | A | S | Q | K | D | L | L | E | Q | R | R | A | + | ++ | ++++ |
| 46 | W | N | A | Q | K | D | L | L | E | Q | R | R | A | + | ++ | ++++ |
| 47 | W | N | S | A | K | D | L | L | E | Q | R | R | A | + | ++ | ++++ |

ND DR ANTIBODY

ANTI-HLA-DR ANTIBODY

TECHNICAL FIELD

The present invention relates to an anti-HLA-DR antibody that recognizes the human leucocyte antigen-DR (HLA-DR), which is a cell membrane molecule associated with immunity. Further, the present invention relates to the following two types of agents comprising, as an active ingredient, the anti-HLA-DR antibody: (1) a preventive or therapeutic agent for diseases caused by an HLA-DR-expressing cell, especially, a therapeutic agent for malignant tumors; and (2) a preventive or therapeutic agent for immune responses caused by an HLA-DR-expressing cell, especially, a therapeutic agent for chronic rheumatism.

BACKGROUND ART

The use of an antibody, which binds to a protein expressed on a cell surface and is capable of leading the cell to death or toxicity, has been attempted in the treatment of cancer, etc. At present, a chimeric antibody (Rituximab) targeting CD20, which is a receptor existing on a cell membrane, and a monoclonal antibody such as a humanized antibody targeting Her2/neu are used in the treatment of malignant tumors, and their therapeutic effects are acknowledged. An antibody is characterized by a long serum half-life and high specificity for an antigen, and thus is particularly useful as an anti-tumor agent. For example, when an antibody targeting a tumor-specific antigen is administered, accumulation thereof in the tumor is presumed. Thus, an attack by the immune system due to the complement-dependent cytotoxicity (CDC) or antibody-dependent cellular cytotoxicity (ADCC) on cancer cells can be expected. Binding of a radionuclide or an agent such as a cytotoxic substance to the antibody enables the effective transmission of the bound agent to a tumor site. This also reduces the amount of the agent reaching other non-specific tissues, and thus reduced side effects can be expected. When a tumor-specific antigen has activity for inducing cell death, an agonistic antibody is administered. In contrast, when a tumor-specific antigen is associated with growth and survival of cells, a neutralizing antibody is administered. This can result in the accumulation of tumor-specific antibodies and arrest or regression of tumor growth due to the activity of the antibody. As mentioned above, antibodies are considered suitable for application as anti-tumor agents because of their features.

Recently, significant anti-tumor effects of Rituximab have been exhibited with respect to B-cell lymphoma, and the side effects thereof are limited. Since Rituximab is a chimeric human-mouse protein, however, the antigenicity of Rituximab itself is strong, an antibody against a mouse moiety is produced inside the body, and the effect could be deteriorated. For some types of cancer, the therapeutic effect of Rituximab is low with the use of Rituximab alone, and the combined use thereof with an anticancer agent is currently being clinically examined (see McLaughlin P. et. al., J Clin Oncol. (1998), 16, 2825–2833; Coiffier B. et al., Blood (1998), 92, 1927–81). Accordingly, a novel anti-tumor antibody targeting an antigen is needed, and a monoclonal antibody against HLA-DR, which is a class II major histocompatibility complex (MHC) molecule, can be expected to have clinical anti-tumor activity as an antibody that recognizes an antigen different from that recognized by Rituximab.

In contrast, class II major histocompatibility complex (MHC) molecules bind to antigen peptide fragments and present these antigen peptide fragments to helper (CD4$^+$) T-cells ("Th" cells) (see Babbin B. et al., Nature (1985), 317, 359–361). A monoclonal antibody that is specific for the class II MHC molecules is reported as a very potent selective inhibitor against the immune response of Th cells in vitro (see Baxevanis C N, et. al., Immunogenetics (1980), 11, 617–625). Since this monoclonal antibody was discovered, it has been considered to be an agent that can be used in the selective immunosuppressive therapy of autoimmune diseases such as chronic rheumatism. Based on the initial in vivo research, significant effects of these monoclonal antibodies on Th cellular heterogeneity and autoimmune response have been elucidated (see Rosenbaum J T. et al., J. Exp. Med. (1981), 154, 1694–1702; Waldor M K. et al., Proc. Natl. Acad. Sci. USA (1983), 80, 2713–2717; Jonker M. et al., J. Autoimmun. (1988), 1, 399–414; Stevens H P. et al., Transplant. Proc. (1990), 22, 1783–1784). Further, as a result of research using primates, it was discovered that graft-versus-host disease in homograft was suppressed (Billing R. & Chatterjee S. (1983), Transplant. Proc., 15, 649–650; Jonker M. et al., Transplant Proc. (1991), 23, 264–265).

Currently, immunological rejection at the time of organ transplantation is clinically suppressed using immunosuppressive agents such as cyclosporin A or FK506. A disadvantage of these immunosuppressive agents is that potent side effects are caused by the non-specific suppression of the immune response.

Accordingly, antibodies are considered suitable for use as immunosuppressive agents with few side effect because of their features.

DISCLOSURE OF THE INVENTION

An immunosuppressive agent using a human antibody having high immunosuppressive activity and low immunogenicity has not yet been developed.

An object of the present invention is to produce such an antibody and use it as an anti-tumor agent or immunosuppressive agent.

The present inventors have conducted concentrated studies in order to produce an antibody against human HLA-DR. As a result, they have succeeded in obtaining a monoclonal antibody exhibiting an anti-tumor effect at very low concentration on HLA-DR-expressing cancer cells and a monoclonal antibody that specifically suppresses immune activity through HLA-DR. Further, they have identified the sequence in the variable region of the monoclonal antibody and determined the epitope to which the monoclonal antibody binds. This has led to the completion of the present invention.

More specifically, the present invention is as follows.

The present invention provides, in the first aspect thereof, a monoclonal antibody that binds to HLA-DR produced from a mouse-mouse hybridoma, for example, a monoclonal antibody that is preferably a human antibody produced from HD4, HD6, HD8, or HD10, or a functional fragment thereof. The monoclonal antibody produced from HD4, HD6, HD8, or HD10 is of an immunoglobulin G (IgG) type. The hybridoma HD8 and the hybridoma HD10 are deposited internationally at the International Patent Organism Depositary of the National Institute of Advanced Industrial Science and Technology (Tsukuba Central 6, 1-1-1 Higashi, Tsukuba, Ibaraki, Japan) as of Oct. 11, 2001 under the accession numbers FERM BP-7773 and FERM BP-7774, respectively. The hybridoma HD4 is deposited internationally at the International Patent Organism Depositary of the National Institute of Advanced Industrial Science and Technology (Tsukuba Central 6, 1-1-1 Higashi, Tsukuba, Ibaraki, Japan) as of Oct. 11, 2001 under the accession number FERM BP-7771. The hybridoma HD6 is deposited internationally at the International Patent Organism Depositary of the National Institute of Advanced Industrial Science and Technology (Tsukuba Central 6, 1-1-1 Higashi, Tsukuba, Ibaraki, Japan) as of Oct. 11, 2001 under the accession number FERM BP-7772.

According to an embodiment of the present invention, the antibody according to the present invention comprises a variable region of the antibody produced from the aforementioned hybridoma or a functional fragment thereof.

In another embodiment of the present invention, the antibody according to the present invention includes an antibody having a modified subclass, which is an antibody produced from the hybridoma HD8 having an IgG1, IgG2, IgG3, or IgG4 subclass or a functional fragment thereof, an antibody produced from the hybridoma HD4 having an IgG1, IgG2, IgG3, or IgG4 subclass or a functional fragment thereof, an antibody produced from the hybridoma HD10 having an IgG1, IgG2, IgG3, or IgG4 subclass or a functional fragment thereof, or an antibody produced from the hybridoma HD6 having an IgG1, IgG2, IgG3, or IgG4 subclass or a functional fragment thereof. According to a further embodiment of the present invention, the antibody according to the present invention is an antibody having a modified amino acid sequence in the constant region of the heavy chain or a functional fragment thereof. For example, an antibody comprises amino acid 331 in the constant region of the heavy chain according to the EU numbering system (see Sequences of Proteins of Immunological Interest, NIH Publication No. 91-3242) being substituted with Ser or a functional fragment thereof.

In another embodiment of the present invention, the subclass of the antibody or a functional fragment thereof is rearranged to IgG1, IgG2, or IgG4, amino acid 331 in the constant region of the heavy chain according to the EU numbering system is substituted with Ser, and the subclass is modified as IgG1, IgG1Ser, IgG2, IgG2Ser, or IgG4. As a result, only an antibody or a functional fragment thereof having an IgG1 or IgG1Ser subclass develops ADCC, and only an antibody or a functional fragment thereof having an IgG1 or IgG2 subclass develops CDC activity.

In another aspect of the present invention, the present invention provides an antibody that binds to HLA-DR or a functional fragment thereof comprising a variable region of an antibody produced from the hybridoma HD4, HD6, HD8, or HD10. In an embodiment of the present invention, the antibody or a functional fragment thereof according to the present invention comprises a variable region of an antibody produced from the hybridoma HD8 having an amino acid sequence in the mature variable region of the amino acid sequences as shown in SEQ ID NOs: 21 and 23. In another embodiment of the present invention, the antibody or a functional fragment thereof according to the present invention comprises a variable region of an antibody produced from the hybridoma HD4 having the amino acid sequence in the mature variable regions in the amino acid sequences as shown in SEQ ID NOs: 17 and 19.

In a further aspect of the present invention, the present invention relates to an antibody or a functional fragment thereof that can bind to a specific epitope of HLA-DR. In embodiments of the present invention, the antibody according to the present invention is an antibody that binds to HLA-DR or a functional fragment thereof, which maximally binds to the peptide as shown in SEQ ID NO: 82. This peptide is selected from among peptides that are prepared by shifting 2 amino acids of the amino acids in the extracellular region (the amino acid sequence being shown in SEQ ID NO: 147 and the nucleotide sequence being shown in SEQ ID NO: 146) of the HLA-DR β chain (DRB1*15011) to prepare 13-mer peptides (preparing 13-mer peptides for 199 amino acids, i.e., amino acids 29 to 227, in the amino acid sequence as shown in SEQ ID NO: 147), binding the resulting peptides to a cellulose membrane through the C-terminus, and acetylating the N-terminus. Also, the antibody according to the present invention is an antibody that binds to HLA-DR or a functional fragment thereof, which potently binds to all three peptides as shown in SEQ ID NOs: 82, 83, and 84. These peptides are selected from among peptides that are prepared by shifting 2 amino acids of the amino acids in the extracellular region of the HLA-DR β chain (DRB1*15011) to prepare 13-mer peptides, binding the resulting peptides to a cellulose membrane through the C-terminus, and acetylating the N-terminus. Further, the antibody according to the present invention is an antibody that binds to HLA-DR or a functional fragment thereof, which significantly binds to all the peptides as shown in SEQ ID NOs: 24 to 39 and all the peptides as shown in SEQ ID NOs: 40 to 43. These peptides are prepared by shifting 2 amino acids of the amino acids in the extracellular region of the HLA-DR β chain (DRB1*15011) to prepare 13-mer peptides, binding the resulting peptides to a cellulose membrane through the C-terminus, and acetylating the N-terminus.

Furthermore, the present invention provides, in another aspect, an antibody or a functional fragment thereof that can extend the survival of individual mice by suppressing tumor growth (for example, those derived from the Raji cell transplanted to SCID mice). The amount of the antibody or a functional fragment thereof according to the present invention to be administered to tumor-bearing test animals (for example, tumor-bearing test animals such as lymphoma cell-bearing mouse models, each with a body weight of 20 g) is 0.1 μg/body to 1 μg/body or 5 μg/kg to 50 μg/kg. Examples of dose are 1 μg/body or 50 μg/kg, and preferably 0.1 μg/body or 5 μg/kg.

In an embodiment of the present invention, the antibody according to the present invention binds to HLA-DR or a functional fragment thereof, which has the following properties (a) and (b):

(a) when a 6-week-old SCID mouse is inoculated intravenously with 10 μl of the anti-asialo GM1 antiserum, on the next day, inoculated intravenously with $5 \times 10^6$ of Burkitt's lymphoma cells Raji (ATCC CCL-86), and 5 days thereafter, inoculated with 5 to 50 μg/kg, based on body weight, of the antibody of the present invention, the survival ratio of the mouse is higher than that achieved when inoculated with the same amount of the human anti-HSA antibody; and (b) the immunosuppressive activity is lower than that achieved when using the mouse anti-HLA-DR monoclonal antibody L243 (ATCC HB-55) at the same concentration, wherein the immunosuppressive activity is assayed as follows: 50 μl of antibody adjusted at 8 μg/mL, and preferably 8 μg/mL using 10% FCS-containing RPMI 1640 medium is mixed with 50 μL of mature dendritic cell suspension derived from a first human donor adjusted at $2 \times 10^5$ cells/mL using 10% FCS-containing RPMI 1640 medium in wells of a 96-well plate, the mixture is allowed to stand at 4° C. for 30 minutes, the resultant is mixed with 100 μL of T-cell suspension (purity: 99% or higher) adjusted at $1 \times 10^6$ cells/mL using 10% FCS-containing RPMI 1640 medium derived from a second human donor having a histocompatible antigen different from that of the first human donor, the mixture is cultured at 37° C. in the presence of 5% $CO_2$ for 5 days, $^3H$ thymidine is added thereto at 1.0 μCi/well, the resultant is cultured at 37° C. in the presence of 5% $CO_2$ for 16 to 20 hours, the $^3H$ thymidine incorporated in the cell is recovered and then measured using a scintillator, and the incorporation of the $^3H$ thymidine into the cell is used as an indicator to assay the immunosuppressive activity.

Further, the present invention provides, in another aspect thereof, an antibody recognizing HLA-DR or a functional fragment thereof, which exhibits immunosuppressive activity equivalent to or higher than that of the mouse anti-HLA-DR monoclonal antibody L243 (ATCC HB-55). In an embodiment of the present invention, the antibody or a functional fragment thereof according to the present invention has the immunosuppressive activity equivalent to or higher than that achieved when using the mouse anti-HLA-DR monoclonal antibody L243 (ATCC HB-55) at the same concentration, wherein the immunosuppressive activity is assayed in the following manner. First, 50 μl of antibody adjusted at 8 μg/mL using 10% FCS-containing RPMI 1640 medium is mixed with 50 μL of mature dendritic cell suspension derived from a first human donor adjusted at $2 \times 10^5$ cells/mL using 10% FCS-containing RPMI 1640 medium in wells of a 96-well plate. The mixture is then allowed to stand at 4° C. for 30 minutes, and the resultant is mixed with 100 μL of T-cell suspension (purity: 99% or higher) adjusted at 1 x 106 cells/mL using 10% FCS-containing RPMI 1640 medium derived from a second human donor having a histocompatible antigen different from that of the first human donor. The resultant is cultured at 37° C. in the presence of 5% $CO_2$ for 5 days, 3H thymidine is added thereto at 1.0 μCi/well, the resultant is further cultured at 37° C. in the presence of 5% CO2 for 16 to 20 hours, the $^3H$ thymidine incorporated in the cell is recovered and then measured using a scintillator, and incorporation of the $^3H$ thymidine into the cell is used as an indicator to assay the immunosuppressive activity.

The present invention further provides, in another aspect, a nucleic acid encoding an antibody comprising a variable region of an antibody produced from a hybridoma or a functional fragment thereof, wherein said nucleic acid is possessed by a hybridoma selected from the group consisting of the hybridoma HD8 (accession number FERM BP-7773), the hybridoma HD10 (accession number FERM BP-7774), the hybridoma HD4 (accession number FERM BP-7771), and the hybridoma HD6 (accession number FERM BP-7772), a protein encoded by the nucleic acid, an expression vector having the nucleic acid, and a host selected from the group consisting of E. coli, yeast cell, insect cell, mammalian cell, plant cell, and mammalians having the expression vector. The present invention provides in its embodiments: a nucleic acid encoding the antibody or a functional fragment thereof, which comprises a variable region having an amino acid sequence of the mature variable regions of the amino acid sequences as shown in SEQ ID NOs: 17 and 19; a nucleic acid encoding the antibody or a functional fragment thereof, which comprises a variable region having an amino acid sequence of the mature variable regions of the amino acid sequences as shown in SEQ ID NOs: 21 and 23; and a nucleic acid encoding the antibody or a functional fragment thereof, wherein the antibody is selected from the group consisting of the antibody HD8G1Ser, the antibody HD8G2Ser, and the antibody HD4G2Ser. The antibody HD8G1Ser is the antibody HD8 having an IgG1 subclass and amino acid 331 according to the EU numbering system being substituted with Ser, the antibody HD8G2Ser is the antibody HD8 having an IgG2 subclass and amino acid 331 according to the EU numbering system being substituted with Ser, and the antibody HD4G2Ser is the antibody HD4 having an IgG2 subclass and amino acid 331 according to the EU numbering system being substituted with Ser.

The present invention further provides, in another aspect thereof, a process for producing the anti-HLA-DR monoclonal antibody, wherein a gene encoding the anti-HLA-DR monoclonal antibody is isolated from a hybridoma selected from the group consisting of the hybridoma HD8 (accession number FERM BP-7773), the hybridoma HD10 (accession number FERM BP-7774), the hybridoma HD4 (accession number FERM BP-7771), and the hybridoma HD6 (accession number FERM BP-7772), an expression vector having said gene is constructed, the expression vector is introduced into a host to express the monoclonal antibody, and the anti-HLA-DR monoclonal antibody is collected from the resulting host, a culture supernatant of the host, or a secretion product of the host.

The present invention further provides, in another aspect thereof, a preventive, therapeutic, or diagnostic agent for tumors, which comprises, as an active ingredient, the aforementioned antibody or a functional fragment thereof.

Examples of tumors that can be prevented or treated include at least one member selected from the group consisting of leukemia (including chronic lymphatic leukemia and acute lymphatic leukemia), lymphoma (including non-Hodgkin's lymphoma, Hodgkin's lymphoma, T-cell lymphoma, B-cell lymphoma, Burkitt's lymphoma, malignant lymphoma, diffuse lymphoma, and follicular lymphoma), myeloma (including multiple myeloma), breast cancer, colon cancer, kidney cancer, gastric cancer, ovarian cancer, pancreatic cancer, cervical cancer, endometrial cancer, esophageal cancer, liver cancer, head and neck squamous cancer, skin cancer, urinary tract cancer, prostate cancer, choriocarcinoma, pharyngeal cancer, laryngeal cancer, pleural tumor, arrhenoblastoma, endometrial hyperplasia, endometriosis, embryoma, fibrosarcoma, Kaposi's sarcoma, angioma, cavernous angioma, hemangioblastoma, retinoblastoma, spongiocytoma, neurofibroma, oligodendroglioma, medulloblastoma, neuroblastoma, neuroglioma, rhabdomyoblastoma, glioblastoma, osteogenic sarcoma, leiomyosarcoma, thyroid sarcoma, and Wilms tumor.

The present invention provides, in another aspect, an immunosuppressive agent comprising, as an active ingredient, the antibody or a functional fragment thereof according to the present invention. The present invention further provides a preventive, therapeutic, or diagnostic agent for autoimmune diseases or allergies, which comprises, as an active ingredient, the antibody or a functional fragment thereof according to the present invention.

In an embodiment of the present invention, a preventive or therapeutic agent is an immunosuppressive agent at the time of organ transplantation (a preventive or therapeutic agent for immunological rejection at the time of pancreatic islet or kidney transplantation or GVHD), a therapeutic agent for autoimmune diseases (for example, rheumatism, arteriosclerosis, multiple sclerosis, systemic erythematodes, idiopathic thrombocythemia, or Crohn's disease), or a preventive or therapeutic agent for allergic diseases such as asthma. In another embodiment of the present invention, the life-extending effects are recognized in the tumor-bearing SCID mice to which the Raji cell had been transplanted 5 days after the tumor transplantation with the administration of 5 μg/kg or lower of the antibody or a functional fragment thereof according to the present invention.

The present invention includes an antibody or a functional fragment comprising the amino acid sequences in the mature variable region of the heavy chain and that of the light chain of the antibody produced from the hybridoma HD4 as shown in SEQ ID NO: 17 or 19 and the amino acid sequences in the mature variable region of the heavy chain and that of the light chain of the antibody produced from the hybridoma HD8 as shown in SEQ ID NO: 21 or 23.

The aforementioned antibody or a functional fragment thereof comprises, for example, the amino acid sequence in the mature variable region of the heavy chain and that of the light chain encoded by the nucleic acid sequence isolated from the hybridoma HD4 as shown in SEQ ID NO: 16 or 18 and the amino acid sequence in the mature variable region of the heavy chain and that of the light chain encoded by the nucleic acid sequence isolated from the hybridoma HD8 as shown in SEQ ID NO: 20 or 22.

The present invention is hereafter described in detail.

It is also reported that the anti-HLA-DR monoclonal antibody has activity of suppressing immune responses. Based on the initial in vivo research, significant effects of the anti-HLA-DR monoclonal antibody on Th cellular heterogeneity and autoimmune response were elucidated (see Rosenbaum J T. et al., J. Exp. Med. (1981), 154, 1694–1702; Waldor M K. et al., Proc. Natl. Acad. Sci. USA (1983), 80, 2713–2717; Jonker M. et al., J. Autoimmun. (1988), 1, 399–414; Stevens H P. et al., Transplant. Proc. (1990), 22, 1783–1784). Further, as a result of research using primates, it was discovered that graft-versus-host disease in homograft was suppressed (Billing R. & Chatterjee S. (1983), Transplant. Proc., 15, 649–650; Jonker M. et al., Transplant Proc. (1991), 23, 264–265). These reported antibodies, however, are mouse antibodies. Recently, Protein Design Labs Inc. has developed a humanized HLA-DR antibody using the mouse anti-HLA-DR antibody 1D10 and converting regions other than the variable region into the sequence of the human antibody by their humanizing techniques and gene recombination (see Sheri A K. et. al., Int. J. Cancer (2001), 93, 556–565). This is clinically examined in the U.S.

The novel human anti-HLA-DR monoclonal antibody according to the present invention is a complete human antibody, and the antigenicity against the mouse sequences, which is always problematic in the mouse antibody, has already been resolved.

Any of the immunoglobulin G (IgG), immunoglobulin A (IgA), immunoglobulin E (IgE), and immunoglobulin M (IgM) antibodies can be suitably used. In general, IgG is preferable.

The terms used in the present invention are defined in order to describe the present invention in more detail.

1. HLA-DR and an Antibody thereof

The antibody according to the present invention is an antibody against HLA-DR, which is a class II major histocompatibility complex (MHC), i.e., an antibody that recognizes and binds to HLA-DR and an antibody that has reactivity with HLA-DR.

The "antibody that binds to HLA-DR" in the present invention is an antibody or a portion thereof having reactivity with human HLA-DR or a portion thereof, and it includes a functional fragment thereof. A "functional fragment" refers to a portion of an antibody (a partial fragment), which has at least one function of the antibody on an antigen. Specific examples thereof include F(ab')$_2$, Fab', Fab, Fv, disulphide-linked Fv, single-chain Fv (scFv), and a polymer thereof (D. J. King, Applications and Engineering of Monoclonal Antibodies, 1998, T. J. International Ltd.). Or, a "functional fragment" is a fragment of an antibody that is capable of binding to an antigen. A functional fragment of the antibody according to the present invention binds to HLA-DR and exhibits an anti-tumor effect or potent immunosuppressive activity.

The term "human antibody" used herein refers to an antibody, which is an expression product of a human-derived antibody gene. The human antibody can be obtained by introducing a human antibody locus and administering an antigen to a transgenic animal that is capable of producing a human-derived antibody as described below. An example of such a transgenic animal is a mouse, and a process for producing a mouse that can produce a human antibody is described in WO 02/43478.

Examples of the antibody according to the present invention include various antibodies exhibiting anti-tumor effects at low concentration on human HLA-DR-expressing cancer cells as described in the examples below.

The antibody according to the present invention includes a monoclonal antibody comprising the heavy chain and/or light chain having an amino acid sequence with deletion, substitution, or addition of one or several amino acids in various amino acid sequences thereof. The aforementioned partial modification of amino acid (deletion, substitution, insertion, or addition) can be introduced into the amino acid sequence of the antibody according to the present invention by partially modifying the nucleotide sequence encoding the amino acid sequence of interest. Such partial modification of the nucleotide sequence can be introduced by a general method of conventional site specific mutagenesis (Proc Natl Acad Sci USA, 1984, Vol. 81: 5662). The antibody used herein refers to an immunoglobulin in which all regions including a variable region and a constant region of the heavy chain and a variable region and a constant region of the light chain constituting the immunoglobulin are derived from a gene encoding the immunoglobulin.

The antibody according to the present invention includes an antibody having any immunoglobulin class and isotype.

The anti-HLA-DR antibody according to the present invention can be produced by a process as described below. Specifically, human HLA-DR, a part thereof, a binding product thereof with a suitable carrier substance for enhancing antigenicity of the antigen (e.g., bovine serum albumin), or the like is administered to a non-human mammalian, such as a human antibody-producing transgenic mouse, for immunization together with an immunopotentiating agent (e.g., Freund's complete or incomplete adjuvant), if necessary. Alternatively, a gene encoding the human HLA-DR α chain or β chain can be introduced, and an animal cell having excessively expressed HLA-DR on its surface can be administered for immunization. A monoclonal antibody can be obtained by culturing a hybridoma obtained by fusing an antibody-producing cell obtained from the immunized animal and a myeloma cell incapable of producing an autoantibody, and selecting a clone that produces a monoclonal antibody having specific affinity to the antigen used for the immunization.

The antibody according to the present invention includes those having different subclasses that were modified by genetic engineering known to a person skilled in the art (see, for example, EP 314161). Specifically, an antibody having a subclass that is different from the original subclass can be obtained using DNA encoding a variable region of the antibody according to the present invention using a genetic engineering technique. For example, the subclass of the antibody according to the present invention can be converted into IgG2 or IgG4 to obtain an antibody having a low degree of binding to the Fc receptor. On the contrary, the subclass of the antibody according to the present invention can be converted into IgG1 or IgG3 to obtain an antibody having a high degree of binding to the Fc receptor. Further, modification of the amino acid sequence in the constant region of the antibody according to the present invention by genetic engineering or binding with a sequence of a constant region having such a sequence enables changing of the degree of binding to the Fc receptor (see Janeway C A. Jr. and Travers P. (1997), Immunobiology, Third Edition, Current Biology Ltd./Garland Publishing Inc.) or that to the complement (see Mi-Hua Tao, et al., 1993, J. Exp. Med). The antibody according to the present invention includes these antibodies having modified amino acid sequences in the constant regions. Modification of the amino acid sequence refers to deletion, substitution, or addition of one or several amino acids of the amino acid sequence. For example, the sequence CCC encoding proline (P) 331 in the constant region of the heavy chain according to the EU numbering system (see Sequences of proteins of immunological interest, NIH Publication No. 91-3242) is varied to TCC encoding serine (S) to substitute proline with serine, thereby changing the degree of binding to the complement. In the case of an anticancer agent, when the antibody itself does not have activity of inducing cell death, a preferable antibody has anti-tumor activity due to the antibody-dependent cellular cytotoxicity (ADCC) or complement-dependent cytotoxicity (CDC) through the Fc receptor. When the antibody itself has activity of inducing cell death, an antibody having a low degree of binding to the Fc receptor may be preferable. In the case of an immunosuppressive agent, an antibody having no ACDD or CDC activity is preferable when, for example, only the binding between the T-cell and the antigen-presenting cell is three-dimensionally suppressed. When ADCC or CDC activity could cause toxicity, an antibody having resolved the toxicity-causing activity by varying the Fc portion or changing the subclass may be preferable.

The antibody according to the present invention includes a modified antibody, the subclass of which has been rearranged to IgG1, IgG2, or IgG4, and a modified antibody, in which amino acid 331 in the constant region of the heavy chain of the modified antibody, the subclass of which has been rearranged to IgG1 or IgG2, according to the EU numbering system, has been substituted with Ser to constitute IgG1Ser or IgG2Ser. Specifically, the present invention includes an antibody in which only IgG1 and the IgG1Ser exhibit ADCC activity and only IgG1 and the IgG2 exhibit CDC activity as a result of the subclass modification into IgG1, IgG1Ser, IgG2, IgG2Ser, or IgG4.

Therapeutic effects on diseases such as cancer can be further enhanced by binding, for example, radionuclides such as iodine, yttrium, indium, and technetium (J. W. Goding, Monoclonal Antibodies: principles and practice, 1993, ACADEMIC PRESS), bacterial toxins such as *Pseudomonas exotoxin*, diphtheria toxin, and ricin, chemotherapeutants such as methotrexate, mitomycin, and calicheamicin (D. J. King, Applications and Engineering of Monoclonal Antibodies, 1998, T. J. International Ltd, M. L. Grossbard, Monoclonal Antibody-Based Therapy of Cancer, 1998, Marcel Dekker Inc), or a prodrug such as maytansinoid (Chari et al., Cancer Res., 1992, Vol. 52: 127, Liu et al., Proc Natl. Acad Sci USA, 1996, Vol. 93: 8681) to the antibody according to the present invention.

In the present invention, the following steps are included in the production of a monoclonal antibody: (1) purification of a biopolymer that is used as an immunogen and/or production of a cell having excessively expressed antigen proteins on its surface; (2) production of an antibody-producing cell by immunizing an animal by injecting an antigen, sampling blood to assay the antibody titer, and determining the stage of excising the spleen or the like; (3) preparation of myeloma cells; (4) cell fusion between an antibody-producing cell and the myeloma cell; (5) selection of a group of hybridomas producing an antibody of interest; (6) division (cloning) into a single cell clone; (7) if necessary, culture of a hybridoma for mass-producing monoclonal antibodies or breeding animals to which the hybtridoma has been transplanted; (8) examination of physiological activity or recognition specificity of the thus produced monoclonal antibody or examination of properties thereof as labeling reagents; and the like.

A process for producing the anti-HLA-DR monoclonal antibody is hereafter described in detail along with the above steps, although the process for producing the antibody is not limited thereto. For example, an antibody-producing cell other than a splenic or myeloma cell can also be used.

(1) Purification of Antigen

A transformant is obtained by incorporating DNA encoding the HLA-DR α chain and β chain into an expression vector for animal cells and introducing the expression vector into an animal cell. This can be used as an antigen in that state. Since the primary structures of the HLA-DR α chain and β chain are known (Steven G E, et al., (2000), The HLA FactsBook, Academic Press), a peptide is chemically synthesized from the amino acid sequence of HLA-DR by a method known to a person skilled in the art, and the resultant can be used as an antigen.

A cell in which the full-length α chain and β chain of the human HLA-DR are introduced into the L929 cell and HLA-DR heterodimers are excessively expressed on its surface is also effective as an immunogen. pEF-neo-HLA-DRα and pEF-neo-HLA-DRβ can be produced by separately incorporating DNA encoding the human HLA-DR α chain protein and DNA encoding the human HLA-DR β chain protein into the expression vector for animal cells, pEF-neo. pEF-neo is a vector comprising a neomycin-resistant gene incorporated into modified pEF-BOS (see Mizushima S. & Nagata S., Nucleic Acids Res (1990), 18, 5332). It should be noted that DNA encoding HLA-DR, a vector, a host, or the like is not limited thereto.

Specifically, a transformant obtained by transforming the L929 cell in pEF-neo-HLA-DRα and pEF-neo-HLA-DRβ is cultured, and confirmation of HLA-DR expression using the trait of neomycin resistance acquired by the cell to which the pEF-neo vector has been inserted and the goat anti-HLA-DR polyclonal antibody (DAKO) are employed as indicators, thereby producing the L929 cell having excessively expressed human HLA-DR on its surface.

(2) Step of Preparing Antibody-producing Cell

The antigen obtained in (1) is mixed with an adjuvant such as Freund's complete or incomplete adjuvant or potash alum, and experimental animals are immunized with the resultant as the immunogen. A transgenic mouse capable of producing a human-derived antibody is most suitably used as an experimental animal, and such a mouse is described in literature by Tomizuka et al. (Tomizuka et al., Proc Natl Acad Sci USA, 2000, Vol. 97: 722).

An immunogen can be administered at the time of mouse immunization by any of hypodermic injection, intraperitoneal injection, intravenous injection, endodermic injection, intramuscular injection, or plantar injection. Intraperitoneal injection, plantar injection, or intravenous injection is preferable.

Immunization can be performed once or several times at suitable intervals (preferably at intervals of 2 to 4 weeks). Thereafter, the antibody titer against the antigen in the serum of the immunized animal is assayed, and the animal having a sufficiently high antibody titer is used as a source of antibody-producing cells. This can enhance the effects of the subsequent procedure. In general, the antibody-producing cell derived from an animal 3 to 5 days after the final immunization can be preferably used for the later cell fusion.

Examples of a method for measuring the antibody titer that is used herein include various conventional techniques such as radioimmunoassay (hereafter referred to as "RIA"), enzyme-linked immunosorbent assay (hereafter referred to as "ELISA"), fluorescent antibody technique, and passive haemagglutination. From the viewpoints of detection sensitivity, rapidity, accuracy, the possibility of automating operations, and the like, the use of RIA or ELISA is preferable.

In the present invention, the antibody titer can be assayed in the following manner in accordance with, for example, ELISA. At the outset, an antibody against a human antibody is allowed to adsorb on the surface of the solid phase such as a 96-well plate for ELISA. Subsequently, the surface of the solid phase having no antigen adsorbed thereon is covered with a protein that is unrelated to an antigen, for example, bovine serum albumin (BSA), the surface is washed, it is brought into contact with a gradually-diluted sample (for example, mouse serum) as a primer antibody, and the anti-HLA-DR antibody in the sample is then bound to the antigen. Further, an antibody against an enzyme-labeled human antibody is added as a secondary antibody and bound to a human antibody, followed by washing. Thereafter, the substrate of the enzyme is added, and changes of the absorbance, etc. are assayed based on the coloration due to substrate decomposition. Thus, the antibody titer is calculated.

(3) Step of Preparing Myeloma Cell

A cell incapable of producing autoantibodies derived from a mammalian such as a mouse, rat, guinea pig, hamster, rabbit, or human can be used as a myeloma cell. In general, established cell lines obtained from a mouse, for example, 8-azaguanine-resistant mouse (BALB/c-derived) myeloma cells P3X63Ag8U.1 (P3-U1) (Yelton, D. E. et al., Current Topics in Microbiology and Immunology, 81, 1–7 (1978)), P3/NSI/1-Ag4-1 (NS-1) (Kohler, G. et al. European J. Immunology, 6 511–519 (1976)), Sp2/O-Ag14 (SP-2) (Shulman, M. et al. Nature, 276, 269–270 (1978)), P3X63Ag8.653 (653) (Kearney, J. F. et al. J. Immunology, 123, 1548–1550 (1979)), and P3X63(X63) (Horibata, K. and Harris, A. W. Nature, 256, 495–497 (1975)) are preferably used. These cell lines are subjected to subculture in suitable medium, for example, 8-azaguanine medium (medium prepared by adding 8-azaguanine to RPMI-1640 medium comprising glutamine, 2-mercaptoethanol, gentamicin, and fetal calf serum (hereafter referred to as "FCS"), Iscove's Modified Dulbecco's Medium (hereafter referred to as "IMDM"), or Dulbecco's Modified Eagle Medium (hereafter referred to as "DMEM"). These cell lines are subjected to subculture in normal medium (for example, DMEM containing 10% FCS) 3 to 4 days before the cell fusion to reliably have $2 \times 10^7$ or more cells on the day of the cell fusion.

(4) Cell Fusion

An antibody-producing cell is a plasma cell or a lymphocyte as its precursor cell. This may be obtained from any site of an individual and can be generally obtained from, for example, the spleen, lymph node, bone marrow, tonsilla, peripheral blood, or suitable combinations thereof, with the spleen cell being most commonly used.

After the final immunization, a site containing an antibody-producing cell therein, for example, the spleen, is excised from a mouse having a predetermined antibody titer to produce a spleen cell, which is an antibody-producing cell. The means for fusing this spleen cell with the myeloma cell obtained in step (3) that is most commonly performed at present is a method using polyethylene glycol having relatively low cytotoxicity and simple fusion operations. This method comprises, for example, the following procedures.

Spleen cells and myeloma cells are thoroughly washed in serum-free medium (for example, DMEM) or phosphate-buffered saline (hereafter referred to as "PBS") and mixed with each other to bring the ratio of spleen cells to myeloma cells to approximately 5:1 to 10:1, followed by centrifugation. The supernatant is removed, the precipitated group of cells is thoroughly unraveled, and 1 mL of serum-free medium containing 50% (w/v) polyethylene glycol (molecular weight: 1,000 to 4,000) is then added thereto dropwise while stirring. Thereafter, 10 mL of serum-free medium is slowly added thereto, followed by centrifugation. The supernatant is discarded again, the precipitated cells are suspended in a suitable amount of normal medium containing a hypoxanthine-aminopterin-thymidine (hereafter referred to as "HAT") solution and human interleukin 6 (hereafter referred to as "IL-6") (this medium is hereafter referred to as "HAT medium"), the resultant is fractionated in each well of the culture plate (hereafter referred to as a "plate"), and cultured in the presence of 5% $CO_2$ at 37° C. for approximately 2 weeks. During the culture, HAT medium is suitably supplemented.

(5) Selection of a Group of Hybridomas

When the aforementioned myeloma cells are 8-azaguanine-resistant, i.e., when they are hypoxanthine-guanine phosphoribosyltransferase (HGPRT) deficient, non-fused myeloma cells and cells fused between myeloma cells cannot survive in HAT-containing medium. While cells fused between antibody-producing cells or hybridomas of antibody-producing cells and myeloma cells can survive, the survival time of cells fused between antibody-producing cells is limited. Accordingly, continuation of culture in HAT-containing medium results in survival of only hybridomas of antibody-producing cells and myeloma cells. In consequence, this enables the selection of hybridomas.

HAT medium for the hybridomas grown as a colony is replaced with a medium from which aminopterin has been removed (hereafter referred to as "HT medium"). Thereafter, a part of the culture supernatant is collected to assay the anti-HLA-DR antibody titer by, for example, ELISA. When the aforementioned fusion protein is used as an antigen for ELISA, an operation of eliminating a clone is required so as not to select a clone that produces an antibody which specifically binds to the Fc region of the human IgG. The presence or absence of such a clone can be inspected by, for example, ELISA using the Fc region of the human IgG as an antigen.

A process using a 8-azaguanine-resistant cell line was exemplified above, although other cell lines can be also used depending on the process used for selecting a hybridoma. In such a case, the composition of the medium to be used is also changed.

(6) Step of Cloning

The antibody titer is assayed in the same manner as described in (2), and the hybridomas, which were found to produce specific antibodies, are transferred to the other plate to perform cloning. Examples of cloning processes include:

limiting dilution in which culture is conducted by diluting, so that one hybridoma is contained in a well of the plate; the soft agar method in which culture is conducted in a soft agar medium and colonies are recovered; a method in which culture is conducted by removing one cell using a micromanipulator, and a "sorter clone" process, in which one cell is separated using a cell sorter. Limiting dilution is simple and often employed.

The wells, the antibody titers of which have been recognized, are repeatedly subjected to cloning by, for example, limiting dilution 2 to 4 times, and those having stable antibody titers are selected as anti-HLA-DR monoclonal antibody-producing hybridomas.

The mouse-mouse hybridomas HD8, HD10, HD4, and HD6, the human anti-HLA-DR monoclonal antibody-producing cells according to the present invention, are deposited internationally at the International Patent Organism Depositary of the National Institute of Advanced Industrial Science and Technology (Tsukuba Central 6, 1-1-1 Higashi, Tsukuba, Ibaraki, Japan) as of Oct. 11, 2001. The accession number of the hybridoma HD8 is FERM BP-7773, that of the hybridoma HD10 is FERM BP-7774, that of the hybridoma HD4 is FERM BP-7771, and that of the hybridoma HD6 is FERM BP-7772.

(7) Preparation of Monoclonal Antibody by Culturing Hybridomas

The hybridomas, which have completed the cloning process, are cultured in normal medium, which is a replacement of the HT medium. Large-scale culture is carried out by rotation culture in a large culture flask, spinner culture, or culture in a hollow-fiber system. The supernatant obtained through this large-scale culture is purified using a technique known to a person skilled in the art such as gel filtration. This enables the production of the anti-HLA-DR monoclonal antibody that comprises, as an active ingredient, the preventive or therapeutic agent of the present invention. Also, the hybridoma is multiplied in the abdominal cavity of a mouse of the same lineage (e.g., BALB/c), a nu/nu mouse, rat, guinea pig, hamster, or rabbit. This can provide ascites fluid containing a large amount of the anti-HLA-DR monoclonal antibodies comprising, as an active ingredient, the preventive or therapeutic agent of the present invention. In order to simply carry out the purification, a commercially available monoclonal antibody purification kit (e.g., Mab-Trap GII Kit, Amersham Pharmacia Biotech) or the like can be used.

The thus obtained monoclonal antibody has high antigen specificity for the human HLA-DR.

(8) Examination of Monoclonal Antibody

The isotype and the subclass of the thus obtained monoclonal antibody can be identified in the following manner. Examples of a method for identification include the Ouchterlony method, ELISA, and RIA. Although the Ouchterlony method is simple, this method requires a concentrating operation when the concentration of the monoclonal antibody is low. In the case of ELISA or RIA, however, the isotype and the subclass of the monoclonal antibody can be identified by allowing the culture supernatant to react with the antigen-adsorbed solid phase, and using antibodies, as secondary antibodies, that correspond to various immunoglobulin isotypes and subclasses.

Proteins can be quantified by the Folin-Lowry method or by calculation based on the absorbance at 280 nm (1.4 (OD 280)=immunoglobulin 1 mg/ml).

The epitope recognized by the monoclonal antibody can be identified in the following manner. Various partial constructs of molecules recognized by the monoclonal antibody are first prepared. Partial constructs can be prepared by, for example, a method in which various partial peptides of the molecule are prepared using a conventional technique of synthesizing oligopeptides or a method in which a DNA sequence encoding a partial peptide of interest is incorporated in a suitable expression plasmid using a gene recombination technique to produce partial constructs inside or outside a host such as *E. coli*. These methods are generally used in combinations to attain the above object. For example, several polypeptide sequences, the lengths of which were successively and suitably shortened from the C-terminus or N-terminus of the antigen protein, are prepared by a gene recombination technique known to a person skilled in the art, and the reactivity of the monoclonal antibody therewith is then examined to roughly determine the recognition site.

Thereafter, various oligopeptides in the corresponding site, variants of the peptides, or the like are synthesized using a technique of synthesizing oligopeptides known to a person skilled in the art. The affinity of the monoclonal antibody, which is an active ingredient of the preventive or therapeutic agent of the present invention, with these peptides is then inspected or competition suppressing activity of peptides against the binding between the monoclonal antibody and the antigen is inspected, thereby more precisely limiting the epitope. In order to simply obtain various oligopeptides, a commercially available kit (for example, SPOTs Kit (Genosys Biotechnologies, Inc), a series of Multipin Peptide Synthesis Kits using the multipin synthesis technique (Chiron Corporation), or the like) can be used.

Alternatively, a gene encoding a human monoclonal antibody is cloned from an antibody-producing cell such as a hybridoma, the clone product is incorporated into a suitable vector, and the resultant is introduced into a host (e.g., a mammalian cell strain, *E. coli*, yeast cell, insect cell, or plant cell) to produce a recombinant antibody using a gene recombination technique (P. J. Delves, ANTIBODY PRODUCTION ESSENTIAL TECHNIQUES, 1997, WILEY, P. Shepherd and C. Dean, Monoclonal Antibodies, 2000 OXFORD UNIVERSITY PRESS, J. W. Goding, Monoclonal Antibodies: principles and practice, 1993, ACADEMIC PRESS).

The present invention includes a nucleic acid comprising a gene sequence of an antibody possessed by a hybridoma which produces the antibody of the present invention. More particularly, the present invention includes a nucleic acid that corresponds to the mature variable regions of the heavy chain and the light chain of the antibody produced from the hybridoma of the present invention as described below. The nucleic acid includes DNA and RNA. The present invention includes a nucleic acid, the sequence of which is modified by means of substitution, deletion, and/or addition of at least one nucleotide in the frame portion in the variable region of the heavy or light chain (see FR1, FR2, FR3, and FR4: Sequences of proteins of immunological interest, NIH Publication No. 91-3242), which hybridizes with a nucleic acid complementary to a nucleic acid before sequence modification under stringent conditions, binds to HLA-DR, has (a) life-extending effects in HLA-DR-expressed cancer cell-bearing non-human animals and (b) lower activity of suppressing immune responses compared with that of L243, and encodes an antibody exhibiting immunosuppressive activity equivalent to or higher than that of the mouse anti-HLA-DR monoclonal antibody L243 (ATCC HB-55) in the nucleic acid comprising a gene sequence of the antibody possessed by a hybridoma which produces the antibody of the present invention. The antibody refers to an immunoglobulin in which a variable region and a constant region of the heavy chain and all regions including a variable region and a constant region of the light chain constituting the immunoglobulin are derived from a gene encoding the immunoglobulin. Stringent conditions involve the occurrence of hybridization only when the sequence is at least 90%, preferably at least 95%, and more preferably at least 97% homologous with the DNA sequence encoding the antibody of the present invention. In general, these conditions involve the occurrence of hybridization at a temperature about 5° C. to about 30° C., and preferably about 10° C. to about 25° C. lower than the melting temperature of the perfect hybrid. Stringent conditions are described in J. Sambrook et al., Molecular Cloning, A Laboratory Mannual, Second Edition, Cold Spring Harbor Laboratory Press (1989), and the conditions described therein can be used.

In order to prepare a gene encoding the monoclonal antibody from a hybridoma, DNAs encoding the V region of the L chain, the C region of the L chain, the V region of the H chain, and the C region of the H chain of the monoclonal antibody are prepared by PCR and the like. Oligo DNA constructed from the anti-HLA-DR antibody gene or the amino acid sequence can be used as a primer, and DNA prepared from a hybridoma can be used as a template. These DNAs are incorporated into a suitable vector, and the resultant is introduced into a host to be expressed. Alternatively, these DNAs are separately incorporated into each suitable vector for co-expression.

A phage or plasmid that can autonomously multiply in a host microorganism is used as a vector. Examples of plasmid DNA include a plasmid derived from *E. coli, Bacillus subtilis*, or yeast, and an example of phage DNA is λ phage.

A host that is used in transformation is not particularly limited as long as the gene of interest can be expressed therein. Examples thereof include bacteria (e.g., *E. coli* or *Bacillus subtilis*), yeast, animal cells (e.g., COS cells or CHO cells), and insect cells.

A method for introducing a gene into a host is known, and examples thereof include any methods such as a method using calcium ions, electroporation, spheroplast, the lithium acetate method, the calcium phosphate method, and lipofection. Examples of a method for introducing a gene into animals as described below include microinjection, a method for introducing a gene into the ES cell by electroporation or lipofection, and nucleus transplantation.

In the present invention, the anti-HLA-DR antibody can be obtained by collecting it from a culture product obtained by culturing a tansformant. The "culture product" refers to any of: (a) a culture supernatant; (b) a cultured cell, cultured bacterial cell, or fragmented product thereof; or (c) a secretion product of the transformant. When culturing a transformant, a medium that is suitable for the host of interest is used, and a culture method such as stationary culture or roller bottle culture is employed.

After the culture, when the protein of interest is produced in a bacterial or other cell, the bacterial or other cell is destroyed to collect the antibody. When the antibody of interest is produced outside the bacterial or other cell, the culture solution remaining unchanged is used, or the bacterial or other cell is removed by centrifugation, etc. Thereafter, general biochemical techniques using various types of chromatography for isolation and purification of proteins are performed singly or in suitable combinations. Thus, the antibody of interest can be isolated and purified from the culture product.

With the use of a technique for preparing transgenic animals, animal hosts comprising the genes of the antibody of interest are incorporated in endogenous genes. For example, transgenic cattle, goats, sheep, or pigs are prepared. From the milk secreted from these transgenic animals, a large amount of monoclonal antibodies derived from the antibody genes thereof can be obtained (Wright, G. et al., (1991), Bio/Technology 9, 830–834). When culturing a hybridoma in vitro, a hybridoma is multiplied, maintained, and stored in accordance with various conditions such as properties of the cells to be cultured, purposes of tests and research, or culture methods. A known nutrient medium that is used for producing a monoclonal antibody in a culture supernatant or various nutrient media derived and prepared from a known basal medium can be used to perform the culture.

(9) Properties of the Antibody

The antibody according to the present invention has the following functional properties a) and b), and these properties can be confirmed by, for example, methods described for each item:

a) HLA-DR-expressing human cancer cells are transplanted in immunodeficient mice such as SCID mice, the survival ratio of mice when inoculated with the antibody of the present invention is inspected, and as a result, the number of days for which the mice survive is prolonged; and b) activity of suppressing immune responses by allogeneic mixed lymphocyte reaction is lower than that of L243. More specifically, the properties a) and b) are as follows:

(a) when a 6-week-old SCID mouse is inoculated intravenously with 10 μl of the anti-asialo GM1 antiserum, on the next day, inoculated intravenously with $5 \times 10^6$ of Burkitt's lymphoma cells Raji (ATCC CCL-86), and 5 days thereafter, inoculated once intravenously with 5 to 50 μg/kg, and preferably 5 μg/kg, based on body weight, of the antibody of the present invention, the survival ratio of the mouse 90 days after the inoculation is higher than that 90 days after the inoculation with the same amount of the human anti-HSA antibody; and (b) the immunosuppressive activity is lower than that achieved when using the mouse anti-HLA-DR monoclonal antibody L243 (ATCC HB-55) at the same concentration, wherein the immunosuppressive activity is assayed as follows: 50 μl of antibody adjusted at 8 to 200 μg/mL, and preferably 8 μg/mL using 10% FCS-containing RPMI 1640 medium is mixed with 50 μL of mature dendritic cell suspension derived from a first human donor adjusted at $2 \times 10^5$ cells/mL using 10% FCS-containing RPMI 1640 medium in wells of a 96-well plate, the mixture is allowed to stand at 4° C. for 30 minutes, the resultant is mixed with 100 μL of T-cell suspension (purity: 99% or higher) adjusted at $1 \times 10^6$ cells/mL using 10% FCS-containing RPMI 1640 medium derived from a second human donor having a histocompatible antigen different from that of the first human donor, the mixture is cultured at 37° C. in the presence of 5% $CO_2$ for 5 days, $^3H$ thymidine is added thereto at 1.0 μCi/well, the resultant is cultured at 37° C. in the presence of 5% $CO_2$ for 16 to 20 hours, the $^3H$ thymidine incorporated in the cell is recovered and then measured using a scintillator, and the incorporation of the $^3H$ thymidine into the cell is used as an indicator to assay the immunosuppressive activity.

Examples of such an antibody include an antibody produced from the hybridoma HD4 (accession number: FERM BP-7771), an antibody produced from the hybridoma HD8 (accession number: FERM BP-7773), and an antibody produced from the hybridoma HD10 (accession number: FERM BP-7774).

The aforementioned property a) indicates that the antibody has potent anti-tumor activity.

The antibody according to the present invention has a functional property, that is, activity of suppressing immune responses by allogeneic mixed lymphocyte reaction is equivalent to or higher than that of L243. More specifically, the immunosuppressive activity is equivalent to or higher than that achieved when using the mouse anti-HLA-DR monoclonal antibody L243 (ATCC HB-55) at the same concentration, wherein the immunosuppressive activity is assayed as follows. First, 50 µl of antibody adjusted at 8–200 µg/mL, preferably 8 µg/mL using 10% FCS-containing RPMI 1640 medium is mixed with 50 µL of mature dendritic cell suspension derived from a first human donor adjusted at $2 \times 10^5$ cells/mL using 10% FCS-containing RPMI 1640 medium in wells of a 96-well plate. The mixture is then allowed to stand at 4° C. for 30 minutes, and the resultant is mixed with 100 µL of T-cell suspension (purity: 99% or higher) adjusted at $1 \times 10^6$ cells/mL using 10% FCS-containing RPMI 1640 medium derived from a second human donor having a histocompatible antigen different from that of the first human donor. The resultant is cultured at 37° C. in the presence of 5% $CO_2$ for 5 days, $^3H$ thymidine is added thereto at 1.0 µCi/well, the resultant is further cultured at 37° C. in the presence of 5% $CO_2$ for 16 to 20 hours, the $^3H$ thymidine incorporated in the cell is recovered and then measured using a scintillator, and incorporation of the $^3H$ thymidine into the cell is used as an indicator to assay the immunosuppressive activity. An example of such an antibody is one produced from the hybridoma HD6 (accession number: FERM BP-7772).

The antibody having the aforementioned activity according to the present invention is useful as an ingredient for a preventive or therapeutic agent for malignant tumors or an ingredient for an immunosuppressive agent.

Even more surprisingly, the antibody according to the present invention significantly suppress a lowering in the survival ratio of tumor-bearing mouse models caused by the tumor cell growth at a low dose of 0.1 µg per mouse (5 µg per kg of body weight), and exhibits life extending-effects in mouse models. If the survival ratio of the mice to which the antibody of the present invention has been administered is significantly enhanced compared with that of the control mice when the human anti-human serum albumin (HSA) antibody is administered as a control simultaneously with the antibody according to the present invention, the antibody of the present invention can be determined to exhibit the life extending-effects. For example, the antibody according to the present invention and the anti-HSA antibody are administered to 5 each of tumor-bearing mouse models to which lymphoma cells have been transplanted. If at least one mouse to which the antibody of the present invention has been administered is alive when all of the mice in the group of mice to which the anti-HSA antibody has been administered have died, it can be said that the life extending-effects can be exhibited in tumor-bearing mouse models.

The immunosuppressive effects can be evaluated based on activity of suppressing the immune response by allogeneic mixed lymphocyte reaction (MLR) as described above, and MLR can be carried out in a conventional manner.

Also, the epitope of the HLA-DR recognized by the antibody of the present invention can be identified by a conventional method. For example, regarding 199 amino acids in the extracellular region of the HLA-DR β chain (DRB1*15011) (199 amino acids from amino acids 29 to 227 in the amino acid sequence as shown in SEQ ID NO: 147, and the nucleotide sequence encoding the amino acid sequence as shown in SEQ ID NO: 147 is shown in SEQ ID NO: 146), peptides are prepared by shifting an amino acid in the 13-mer peptides (for example, peptides having amino acid sequences as shown in SEQ ID NOs: 52 to 145), and the reactivity is inspected. In such a case, the antibody according to the present invention maximally binds to the peptide having the amino acid sequence as shown in SEQ ID NO: 82, or potently binds to at least one of the three peptides as shown in SEQ ID NOs: 82, 83, and 84. The term "potently binds" refers to the binding which exhibits fluorescence intensity at least 10 times as great as that of the background in the method as described in Example 17 (2). The antibody of the present invention has reactivity with peptides 61 to 71 of the HLA-DR β chain. Further, HLA-DR is known to have approximately 350 types of polymorphisms (see the IMGT/HLA database of EMBL-EBI, etc.). The antibody according to the present invention is capable of recognizing substantially almost all of these polymorphisms. Whether or not this is true can be determined by preparing a group of peptides including substantially almost all of the approximately 350 types of polymorphisms and assaying the reactivity with substantially almost all of these peptides. For example, if an antibody reacts with 12 or more types of peptides among 16 types of peptides as shown in SEQ ID NOs: 24 to 39, this antibody is capable of recognizing substantially almost all of the polymorphisms of the HLA-DR. The antibody according to the present invention significantly binds to all the peptides as shown in SEQ ID NOs: 24 to 39 and all the peptides as shown in SEQ ID NOs: 40 to 43. The term "significantly binds" refers to the binding which exhibits fluorescence intensity at least 10% as great as the background in the method as described in Example 17 (3).

2. Pharmaceutical Composition

A preparation that comprises a purified preparation of the human anti-HLA-DR antibody of the present invention is also within the scope of the present invention. Such a preparation preferably comprises a physiologically acceptable diluent or carrier in addition to the antibody, and it may be a mixture of the aforementioned antibody with another antibody or another agent such as an antibiotic. Examples of a suitable carrier include, but are not limited to, physiological saline, phosphate-buffered saline, phosphate-buffered saline glucose solution, and a buffered saline solution. Alternatively, the antibody may be lyophilized and used by being recomposed with the addition of the above buffered aqueous solution, when it is needed. The preventive or therapeutic agent can be administered in various dosage forms, and examples of dosage forms include oral administration in the form of, for example, a tablet, capsule, granule, powder, or syrup and parenteral administration in the form of, for example, an injection, drop, or suppository.

The dose may vary depending on symptom, age, body weight, etc. In the case of oral administration, the dose is generally about 0.01 mg to 1,000 mg per day per adult, and this amount of preparation can be administered in one dose or several separate doses. In the case of parenteral administration, about 0.01 mg to 1,000 mg can be administered per dose through hypodermic injection, intramascular injection, or intravenous injection.

The antibody or a pharmaceutical composition according to the present invention can be applied to the treatment or prevention of various diseases or symptoms that could be caused by an HLA-DR-expressing cell. Examples of such diseases or symptoms include various malignant tumors, and examples of the application thereof are use as an immunosuppressive agent at the time of organ transplantation (a preventive or therapeutic agent for immunological rejection at the time of pancreatic islet or kidney transplantation, or GVHD), a therapeutic agent for autoimmune diseases (for example, rheumatism, arteriosclerosis, multiple sclerosis, systemic erythematodes, idiopathic thrombocythemia, or Crohn's disease), and a therapeutic agent for allergic diseases such as asthma.

For example, the antibody according to the present invention and a pharmaceutical composition comprising this antibody having the following functional properties a) and b) can be used for preventing or treating various malignant tumors:

a) HLA-DR-expressing human cancer cells are transplanted in immunodeficient mice such as SCID mice, the survival ratio of mice when inoculated with the antibody of the present invention is inspected, and as a result, the number of days for which the mice survive is prolonged; and b) activity of suppressing immune responses by allogeneic mixed lymphocyte reaction is lower than that of L243.

The antibody according to the present invention and a pharmaceutical composition comprising this antibody having activity of suppressing immune responses by allogeneic mixed lymphocyte reaction equivalent to or higher than that of L243 can be used for preventing or treating rheumatism or graft-versus-host disease (GvHD).

The present invention includes a process for preventing or treating the aforementioned diseases using the antibody or pharmaceutical composition according to the present invention. The present invention also includes the use of the antibody according to the present invention in the production of a preventive or therapeutic agent for the aforementioned diseases.

Examples of tumors that can be prevented or treated are leukemia (including chronic lymphatic leukemia and acute lymphatic leukemia), lymphoma (including non-Hodgkin's lymphoma, Hodgkin's lymphoma, T-cell lymphoma, B-cell lymphoma, Burkitt's lymphoma, malignant lymphoma, diffuse lymphoma, and follicular lymphoma), myeloma (including multiple myeloma), breast cancer, colon cancer, kidney cancer, gastric cancer, ovarian cancer, pancreatic cancer, cervical cancer, endometrial cancer, esophageal cancer, liver cancer, head and neck squamous cancer, skin cancer, urinary tract cancer, prostate cancer, choriocarcinoma, pharyngeal cancer, laryngeal cancer, pleural tumor, arrhenoblastoma, endometrial hyperplasia, endometriosis, embryoma, fibrosarcoma, Kaposi's sarcoma, angioma, cavernous angioma, hemangioblastoma, retinoblastoma, spongiocytoma, neurofibroma, oligodendroglioma, medulloblastoma, neuroblastoma, neuroglioma, rhabdomyoblastoma, glioblastoma, osteogenic sarcoma, leiomyosarcoma, thyroid sarcoma, and Wilms tumor. When the antibody of the present invention is applied, the kind of a tumor is not limited to one, and combinations of several kinds of tumors may be involved.

3. Preparation Example

The molecule according to the present invention is used as an ampule for an aseptic solution or suspension dissolved in water or another pharmaceutically acceptable solution. Also, the ampule is filled with an aseptic powder preparation (preferably lyophilized molecules of the present invention), and it may be diluted with a pharmaceutically acceptable solution at the time of use thereof.

BRIEF DESCRIPTION OF THE DRAWINGS

FIG. 2 is a diagram showing the life-extending effects of the purified human anti-HLA-DR monoclonal antibody on the tumor-bearing mouse model. FIG. 2A shows a case where the dose is 1 µg/head.

FIG. 3 is a diagram showing the antibody-dependent cellular cytotoxicity (ADCC) and the complement-dependent cytotoxicity (CDC) of the purified human anti-HLA-DR monoclonal antibody. FIG. 3B shows the CDC activities of HD8G2CHO, HD8G1, HD8G1Ser, and HD8G4, FIG. 3C shows the ADCC activities of HD8G1, HD8G2, HD8G2Ser, HD8G4, HD4G1, HD4G2Ser, and HD4G4.

FIG. 4 is a diagram showing the life-extending effects of the antibodies according to the present invention, HD8G1Ser, HD8G2Ser, and HD8G1, on the tumor-bearing mouse model. FIG. 4B shows the results attained when the dose is 1.0 µg per mouse.

FIG. 5 is a diagram showing the analysis of the purified human anti-HLA-DR monoclonal antibody epitope using the synthetic peptide in the HLA-DR β chain sequence.

FIG. 6 is a diagram showing the analysis of the purified human anti-HLA-DR monoclonal antibody epitope using the synthetic peptide in the polymorphic sequence in the HLA-DR β chain epitope sequence.

FREE TEXT OF SEQUENCE LISTING

Figure 1:
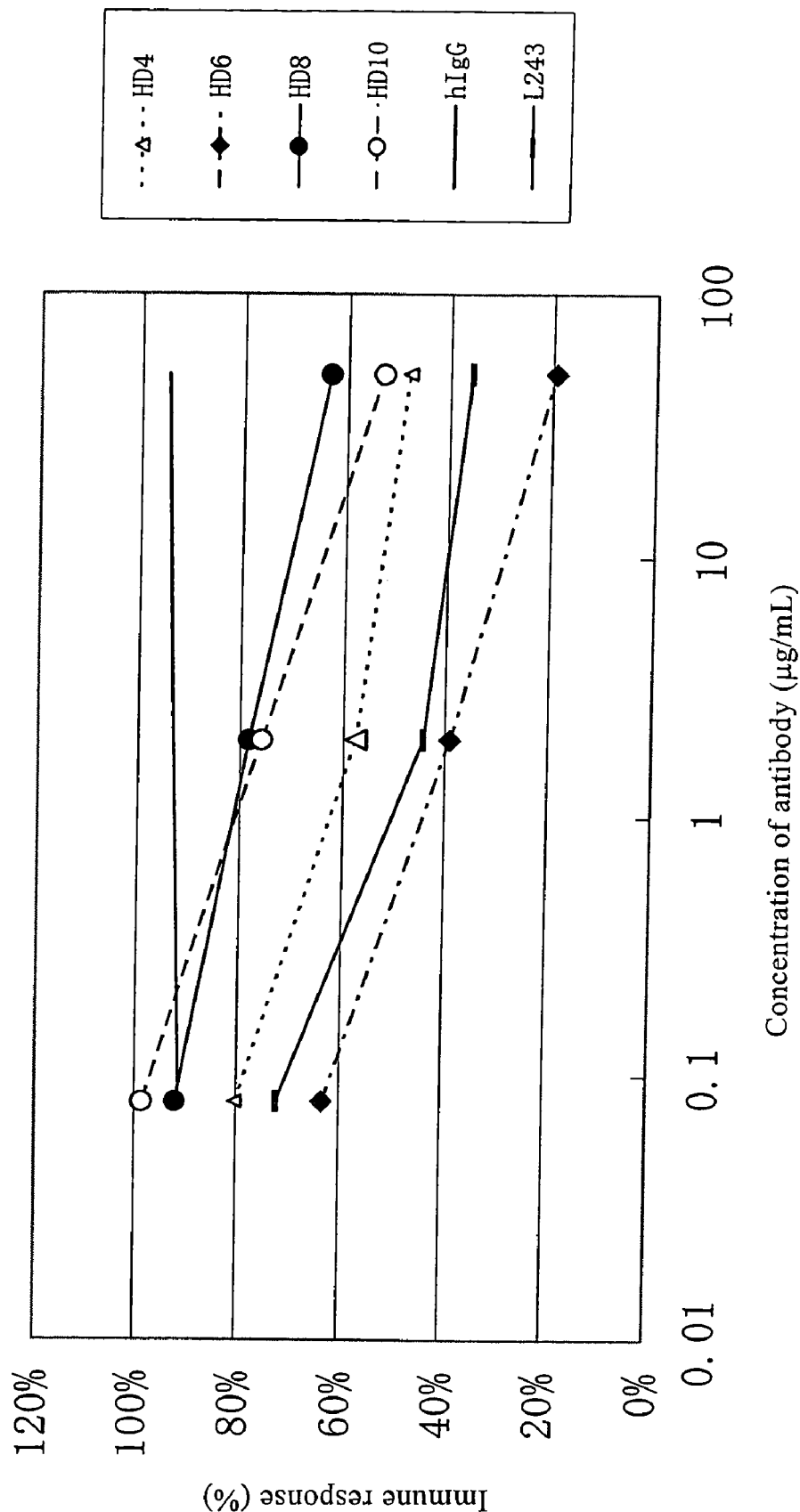
FIG. 1 is a diagram showing the immunosuppressive activity of the purified human anti-HLA-DR monoclonal antibody on MLR.

SEQ ID Nos: 1 to 15: description of artificial sequence: primer

SEQ ID Nos: 24 to 145: description of artificial sequence: peptide

BEST MODES FOR CARRYING OUT THE INVENTION

The present invention is hereafter described in more detail with reference to the following examples, although the technical scope of the present invention is not limited to the embodiments described in these examples.

EXAMPLE 1

Preparation of Antigen

In order to obtain a cell having excessively expressed human HLA-DR on its cell membrane, plasmid vectors for the expression of full-length amino acids in the human HLA-DR α chain and β chain were prepared. DNA encoding the HLA-DR α chain and β chain was prepared by PCR.

a) Preparation of Expression Vectors for Full-length Human HLA-DR α Chain and β Chain In template PCR, plasmid vectors pEF-neo-HLA-DRα and pEF-neo-HLA-DRβ holding cDNA encoding the human HLA-DR α chain and β chain were used as the templates. pEF-neo-HLA-DRα and pEF-neo-HLA-DRβ were prepared in the manner as described below. DNA of the full-length human HLA-DR α chain and that of the HLA-DR β chain were modified by the polymerase chain reaction (PCR) for adding the EcoRI sequence at the 5'-terminus and the NotI sequence and a stop codon at the 3'-terminus. PCR was carried out for 30 PCR cycles of 94° C. for 15 seconds, 55° C. for 30 seconds, and 72° C. for 60 seconds using, as a template, the cDNA derived from human peripheral blood mononuclear cells, as primers, synthesizing 5'-CCGGAAT-TCCCACCATGGCCATAAGTGGAGTCCCTGTG-3' (SEQ ID NO: 1) with 5'-AAAGCGGCCGCTCATFACA-GAGGCCCCCTGCGTTCTGC-3' (SEQ ID NO: 2) for the HLA-DRα and synthesizing 5'-CCGGAATTCCTGGTCCT-GTCCTGTTCTCCAGCA-3' (SEQ ID NO: 3) with 5'-AAAGCGGCCGCTCATCAGCTCAGGAATC-CTGTTGGCTG-3' (SEQ ID NO: 4) for the HLA-DRβ, and the LA-Taq DNA polymerase (Gibco BRL). The synthesized sequence was isolated as the EcoRI-NotI fragment and linked to the pEF-neo vector cleaved with the same enzyme (a vector comprising the neomycin-resistant gene incorporated in modified pEF-BOS (see Mizushima S. & Nagata S., Nucleic Acids Res (1990), 18, 5332)). The resulting plasmids were designated as pEF-neo-HLA-DRα and pEF-neo-HLA-DRβ. 765 bp cDNA was encoded in the HLA-DRα incorporated in pEF-neo-HLA-DRα, and 801 bp cDNA was encoded in the HLA-DRβ incorporated in pEF-neo-HLA-DRβ. In all of PCRs in the following examples, the reaction temperature was regulated using the Gene Amp PCR System 9700 (Perkin Elmer Japan).

c) Preparation of a Human HLA-DR-expressing Cell pEF-neo-HLA-DRα and pEF-neo-HLA-DRβ prepared in b) were introduced in the L929 cell (American Type Culture Collection (ATCC) No. CCL-1) using LipofectAMINE Plus (Gibco BRL). Gene introduction was carried out in accordance with the method described in the instructions therefor. The gene-introduced cells were cultured in a cell culture flask (culture area: 75 cm$^2$) at 37° C. in the presence of 5.0% $CO_2$ for 24 hours, and G418 (Gibco BRL) was added thereto at 1 mg/mL, followed by culture for a week. Subsequently, flow cytometry (FCM, Becton Dickinson) was carried out using the R-phycoerythrin-labeled mouse anti-human-HLA-DR antibody (BD Pharmingen), and cells having HLA-DR expressed on the surfaces of their cell membranes were selectively sorted from those that had attained G418-resistance among the gene-introduced cells.

All oligonucleotides such as PCR primers were synthesized using a DNA automatic synthesizer (Model: 3948, Perkin-Elmer's Applied Biosystems Division) in accordance with the attached instructions (see Matteucci, M. D. and Caruthers, M. H., (1981), J. Am. Chem. Soc. 103, 3185–3191). After the completion of the synthesis, each of the oligonucleotides was cleaved from the support and then deprotected. The resulting solution was exsiccated, dissolved in distilled water, and then cryopreserved at −20° C. before use.

EXAMPLE 2

Preparation of Human Antibody-producing Mouse

The mouse used for immunization is genetically homozygous for both endogenous Ig heavy chain breakdown and κ light chain breakdown, and simultaneously retains a chromosome 14 fragment (SC 20) containing a human Ig heavy chain locus and a human Igκ chain transgene (KCo5). This mouse was prepared by mating a mouse having a human Ig heavy chain locus (lineage A) with a mouse having a human Igκ chain transgene (lineage B). Lineage A is homozygous for both endogenous Ig heavy chain breakdown and κ light chain breakdown, and retains a chromosome 14 fragment (SC20) that is transmittable. For example, it is described in the report by Tomizuka et al. (Tomizuka et al., Proc. Natl. Acad. Sci. USA, 2000, Vol. 97: 722). Lineage B is homozygous for both endogenous Ig heavy chain breakdown and κ light chain breakdown, and retains a human Igκ chain transgene (KCo5, a transgenic mouse). It is described for example, in the report by Fishwild et al. (Nat. Biotechnol., 1996, Vol. 114: 845).

An individual obtained by mating a male mouse of lineage A with a female mouse of lineage B or a female mouse of lineage A with a male mouse of lineage B in which the human Ig heavy chain and the κ light chain can be simultaneously detected in the serum (Ishida & Lonberg, IBC's 11th Antibody Engineering, Abstract 2000) was used in the following immunity experiment. The aforementioned human antibody-producing mouse (referred to as a "KM mouse") can be obtained from Kirin Brewery Co., Ltd. by making a contract.

EXAMPLE 3

Preparation of Human Monoclonal Antibody Against Human HLA-DR

In this example, a monoclonal antibody was prepared in accordance with a common technique as described in, for example, "Tan-kuron koutai jikken sousa nyuumon (A guide to monoclonal antibody experiments)" (Tamie ANDO et al., Kodansha Ltd. Publishers, 1991). The HLA-DR-expressing L929 cell prepared in Example 1 was used as the immunogen human HLA-DR. A human immunoglobulin-producing human antibody-producing mouse prepared in Example 2 was used as an animal to be immunized.

In order to prepare a human monoclonal antibody against human HLA-DR, human antibody-producing mice were subjected to initial immunization intraperitoneally with the HLA-DR-expressing L929 cells ($5 \times 10^6$ cells per mouse) prepared in Example 1. After the initial immunization, the same cells were administered for immunization 2, 4, and 8 weeks later. Three days before obtaining the spleen and the lymph node as described below, cells ($1 \times 10^6$ cells per mouse) were administered to the tail veins, and recombinant human IL-6 (hereafter referred to as "IL-6," 5 ng per mouse, prepared at the Pharmaceutical Research Laboratory, Kirin Brewery Co., Ltd.) was administered subcutaneously.

The spleen and/or lymph node were surgically obtained from the immunized mouse, the recovered organs were placed in 10 mL of serum-free DMEM medium containing 350 mg/mL sodium bicarbonate, 50 units/mL of penicillin, and 50 μg/mL of streptomycin (Gibco BRL, hereafter referred to as "serum-free DMEM medium"), and mashed on a mesh (cell strainer, Falcon) using a spatula. The cell suspension that had passed through the mesh was centrifuged to precipitate the cells. Thereafter, these cells were washed twice in serum-free DMEM medium and then suspended in serum-free DMEM medium to count the number of cells. In contrast, myeloma cells SP2/0 (ATCC No. CRL-1581), which were cultured in DMEM medium (Gibco BRL) containing 10% FCS (SIGMA) (this medium is hereafter referred to as "serum-containing DMEM medium") at 37° C. in the presence of 5% $CO_2$ in such a manner that the cell concentration did not exceed $1 \times 10^6$ cells/mL, were similarly washed in serum-free DMEM medium and then suspended in serum-free DMEM medium to count the number of cells. The recovered cell suspension and the mouse myeloma cell suspension were mixed with each other at a ratio of 5:1, the mixture was centrifuged, and the supernatant was completely removed. 1 mL of 50% (w/v) polyethylene glycol 1500 (Boehringer Mannheim) was slowly added as a fusing agent to the pellet while stirring the pellet with the tip of a pipette, 1 mL of serum-free DMEM medium previously heated at 37° C. was slowly added two separate times, and 7 mL of serum-free DMEM medium was further added. After the centrifugation, the supernatant was removed, and the resulting fusion cell was subjected to screening by limiting dilution as described below. A hybridoma was selected by culturing it in DMEM medium containing 10% FCS, IL-6 (10 ng/mL), and hypoxanthine (H), aminopterin (A), and thymidine (I) (hereafter referred to as "HAT," SIGMA). Further, a single clone was obtained by limiting dilution using HT (SIGMA), 10% FCS, and IL-6-containing DMEM medium. Culture was conducted in a 96-well microtiter plate (Becton Dickinson). The selection (screening) of a hybridoma clone that produces the anti-human HLA-DR human monoclonal antibody and the characterization of the human monoclonal antibody that is produced by each hybridoma were carried out with enzyme-linked immunosorbent assay (ELISA) and FCM as described later.

In the screening of human monoclonal antibody-producing hybridomas, many human monoclonal antibody-producing hybridomas were obtained, which have human immunoglobulin γ chain (hIgγ) and human immunoglobulin light chain κ, and which have specific reactivity with human HLA-DR through Cell ELISA as described in Examples 4 and 5.

EXAMPLE 4

Selection of Human Anti-HLA-DR Monoclonal Antibody-producing Clones Having Human Immunoglobulin Light Chain κ (Igκ)

Burkitt's lymphoma cells, Daudi (ATCC No. CCL-213), were added to each well in quantities of 1×10⁵ cells, the hybridoma supernatant was added thereto, and the mixture was incubated at 4° C. for 20 minutes. Subsequently, the incubation product was washed twice with 1% FCS-containing PBS, the horseradish peroxidase-labeled goat anti-human immunoglobulin light chain κ (Igκ) antibody (50 μg/well, DAKO) was added thereto, and the resultant was incubated at 4° C. for 20 minutes. The incubation product was washed twice with 1% FCS-containing PBS, and 100 μL each of a TMB chromogenic substrate solution (DAKO) was added to each well, followed by incubation at room temperature for 20 minutes. 0.5M sulfuric acid (100 μL/well) was added to each well to terminate the reaction. Absorbance at a 450 nm wavelength (reference wavelength: 570 nm) was assayed using a microplate reader (1420 ARVO multilabel counter, Wallac) to select positive antibody-producing clones.

EXAMPLE 5

Identification of Subclass of Each Monoclonal Antibody

After the addition of 1×10⁵ Daudi cells to each well, the hybridoma supernatant was added thereto, and the resultant was incubated at 4° C. for 20 minutes. Subsequently, the incubation product was washed twice with 1% FCS-containing PBS, and horseradish peroxidase-labeled sheep anti-human IgG1 antibody, sheep anti-human IgG2 antibody, sheep anti-human IgG3 antibody, or sheep anti-human IgG4 antibody (2000-fold diluted, 50 μL/well, The Binding Site) was added to each well, followed by incubation at room temperature for 1 hour. After being washed three times with 1% FCS-containing PBS, a substrate buffer (TMB, 100 μL/well, DAKO) was added to each well, and incubation was carried out at room temperature for 20 minutes. Subsequently, 0.5M sulfuric acid (100 μL/well) was added to terminate the reaction. Absorbance at a 450 nm wavelength (reference wavelength: 570 nm) was assayed using a microplate reader (1420 ARVO multilabel counter, Wallac) to identify the subclass for each clone. Clones which were not positive for any subclass were excluded from the selection since they were not IgG The results only on the finally selected clones are shown in Table 1.

TABLE 1

Properties of selected anti-HLA-DR monoclonal antibodies

| | Subclass | Activity of suppressing immune responses by allogeneic mixed lymphocyte reaction | Reactivity L929 | Reactivity with L929/ HLA-DR |
|---|---|---|---|---|
| Human IgG | Poly | − | − | − |
| HD3 | IgG1 | ++ | − | + |
| HD4 | IgG1 | ++ | − | + |
| HD6 | IgG1 | +++ | − | + |
| HD7 | IgG3 | + | − | + |
| HD8 | IgG2 | + | − | + |
| HD10 | IgG2 | + | − | + |

EXAMPLE 6

Process for Obtaining Normal Human Mononuclear Cell and Normal Human Dendritic Cell At the outset, a normal human peripheral blood-derived mononuclear cell was prepared in accordance with a conventional method using Ficoll (Ficoll-PaquePLUS, Amersham Pharmacia Biotech). The normal human blood contained in a blood-sampling bag (Terumo) containing a sodium citrate solution as an anticoagulant was centrifuged (600 G, room temperature, 5 minutes) to separate a cell fraction from blood plasma. The cell fraction was diluted with PBS, superposed on Ficoll, and mononuclear cells were separated by specific gravity-based centrifugation (400 G, room temperature, 30 minutes). The intermediate layer was extracted as a mononuclear cell and washed twice with PBS. The resultant was further diluted with PBS, and centrifuged at 100 G for 10 minutes to remove blood platelets remaining in the supernatant. Thus, normal human peripheral blood-derived mononuclear cells (PBMC) were obtained.

Subsequently, the obtained PBMC was allowed to react with CD14 antibody attached to magnetic beads (Miltenyi Biotec (MB)) at 4° C. for 30 minutes, and positive selection for CD14-positive cells was carried out through a MACS separating column (MB). The MACS separating column was used in accordance with the attached instruction. The CD14-positive cells were cultured in 10% FCS-containing RPMI medium comprising GM-CSF (final concentration: 50 ng/mL, prepared at the Pharmaceutical Research Laboratory, Kirin Brewery Co., Ltd.) and interleukin 4 (final concentration: 200 ng/mL, Genzyme Corporation) for 5 to 8 days. Thereafter, lipopolysaccharide (LPS, final concentration: 40 ng/mL, Difco) was added thereto, and the resultant was cultured overnight. The culture product was then used as a mature dendritic cell (mature DC).

EXAMPLE 7

Activity of Suppressing Immune Responses by Allogeneic Mixed Lymphocyte Reaction In an allogeneic transplantation having different major histocompatibility antigens (MHC), the T-cell is activated by recognizing the nonself (histoincompatible) MHC molecular complex (alloantigen), thereby generating immunological rejection. The human MHC is referred to as human leukocyte antigen (HLA), and there are class I antigens to which HLA-A, B, and C belong, and class II antigens to which HLA-DP, DQ, and DR belong. Further, since each molecule has a polymorphic property, several thousand combinations of human HLA are possible. Thus, histoincompatibility is very highly likely to occur with another person. The allogeneic mixed lymphocyte culture is a test to inspect in vitro the growth of T-cells which react with alloantigens by subjecting lymphocytes having different histocompatible antigens (hereafter referred to as donor A and donor B for convenience) to mixed culture.

Activity of suppressing the immune response by allogeneic mixed lymphocytes was assayed using the culture supernatant of hybridomas selected in Examples 4 and 5. A normal human peripheral blood mononuclear cell was obtained in the manner as described in Example 6. The mononuclear cells of donor A were allowed to react in RPMI 1640 medium containing mitomycin C (25 µg/mL, 37° C., 30 minutes) to suppress the multiplication of cells. After the reaction, they were washed at least three times in RPMI 1640 medium and suspended in RPMI 1640 medium at $1\times10^6$/mL. The mononuclear cells of donor B were fractionated in a 96-well plate at $1\times10^5$ cell/well, the medium was removed by centrifugation, the culture supernatant was added at 100 µL/well, and the resultant was allowed to stand at 4° C. for 30 minutes.

Subsequently, the mononuclear cells of donor A were fractionated at 100 µL/well in a 96-well plate containing the mononuclear cells of donor B and the culture supernatant, followed by culturing at 37° C. for 4 days in the presence of 5% $CO_2$. Thereafter, $^3H$ thymidine (Amersham Pharmacia Biotech) was added thereto at 1.0 µCi/well, and culture was further conducted at 37° C. for 16 to 20 hours in the presence of 5% $CO_2$. The $^3H$ thymidine incorporated in cells were collected on a glass filter mat (Printed Filtermat, Wallac) using the Micro96 Harvester (SKATRON), dehydrated, well immersed in scintillator (Betap, Scint, Wallac), and packaged. Thereafter, activity of the β dose was assayed using a liquid scintillation counter (1205 BETAPLATE, Wallac).

Properties of the anti-human HLA-DR antibodies selected as a result of the assay are shown in Table 1. Among those, HD8, HD10, HD4, and HD6 are deposited internationally at the International Patent Organism Depositary of the National Institute of Advanced Industrial Science and Technology (Tsukuba Central 6, 1-1-1 Higashi, Tsukuba, Ibaraki, Japan) as of Oct. 11, 2001. The accession number of the hybridoma HD8 is FERM BP-7773, that of the hybridoma HD10 is FERM BP-7774, that of the hybridoma HD4 is FERM BP-7771, and that of the hybridoma HD6 is FERM BP-7772.

EXAMPLE 8

Preparation of Each Antibody

Thu human anti-HLA-DR monoclonal antibody was purified from the culture supernatant of hybridomas obtained in Examples 4 and 5 in the following manner. The culture supernatant containing the human anti-HLA-DR monoclonal antibody was subjected to affinity purification using rmp Protein A (Amersham Pharmacia Biotech) and a 0.8× 4.0 cm column (Biorad), PBS as an adsorption buffer, and a 0.02M glycin buffer (pH 3) as an elution buffer. The elution fraction was adjusted at around pH 7.2 with the addition of 1M Tris (pH 9.0). The prepared antibody solution was converted into PBS using a dialysis membrane (molecular weight cutoff: 10,000, Spectrum Laboratories), filter-sterilized with a membrane filter MILLEX-GV (pore diameter: 0.22 µm, MILLIPORE), and the purified human anti-HLA-DR monoclonal antibody was obtained. The concentration of the purified antibody was calculated by assaying the absorbance at 280 nm and on the basis of 1 mg/mL=1.4 OD.

The culture supernatant containing the human anti-HLA-DR monoclonal antibody was prepared in the following manner. At the outset, the human anti-HLA-DR monoclonal antibody-producing hybridoma was adapted to eRDF medium (Kyokuto Seiyaku) containing 10 ng/ml of IL-6 and 10% fetal calf serum (FCS, SIGMA). Subsequently, a part thereof was adapted to eRDF medium (Kyokuto Seiyaku) containing bovine insulin (5 µg/ml, Gibco BRL), human transferin (5 µg/ml, Gibco BRL), ethanolamine (0.01 mM, SIGMA), sodium selenite ($2.5\times10^{-5}$ mM, SIGMA), and 1% low IgG FCS (HyClone) to purify the antibody. These adapted hybridomas were cryopreserved. Culture was conducted in a flask, and the culture supernatant was collected when the rate of surviving hybridomas reached 90%. The collected supernatant was applied to 10 µm- and 0.2 µm-filters (Gelman Science) to eliminate waste such as hybridomas.

EXAMPLE 9

Activity of Suppressing Immune Responses by Allogeneic Mixed Lymphocytes by Purified Human Anti-HLA-DR Monoclonal Antibody The allogeneic mixed lymphocyte culture is a test to inspect in vitro the growth of T-cells which react with alloantigens by subjecting lymphocytes having different histocompatible antigens (hereafter referred to as donor A and donor B for convenience) to mixed culture. The mature dendritic cell (DC) derived from a monocyte in vitro induced from the peripheral blood of donor A and the T-cells separated from the peripheral blood of donor B are exclusively subjected to mixed culture. This enables the inspection of similar reactivity of T-cells with an alloantigen when the antibody-dependent cellular cytotoxicity (ADCC) of the macrophage, etc. has been removed. Mixed culture using allogeneic DC and T-cells was carried out in the presence of the anti-HLA-DR monoclonal antibody to inspect the function of the anti-HLA-DR monoclonal antibody on the T-cell alloantigen reactivity. Specifically, the mature DC of donor A was suspended in 10% FCS-containing RPMI 1640 medium (RPMI-10% FCS) at 2×10 cells/mL on a round-bottom, 96-well plate (Falcon). The anti-HLA-DR monoclonal antibody, the human polyclonal IgG (hIgG) as a negative control, and the mouse anti-HLA-DR monoclonal antibody L243 (ATCC HB-55) as a positive control were diluted with RPMI-10% FCS to 200, 40, and 8 µg/mL, respectively. The T-cells separated from the peripheral blood of donor B (purity: 99% or higher) were suspended in RPMI-10% FCS at $1\times10^6$ cells/mL. At the outset, 50 µL of the mature DC derived from donor A was mixed with the same amount of the anti-HLA-DR monoclonal antibody on a 96-well plate, and the resultant was allowed to stand at 4° C. for 30 minutes. Subsequently, 100 µL of T-cells derived from donor B was mixed therewith, cultured at 37° C. for 5 days in the presence of 5% $CO_2$, $^3H$ thymidine (Amersham Pharmacia Biotech) was added at 1.0 µCi/well, and culture was further conducted at 37° C. for 16 to 20 hours in the presence of 5% $CO_2$. The $^3H$ thymidine incorporated in the cells was collected on a glass filter mat (Printed Filtermat, Wallac) using the Micro96 Harvester (SKATRON), dehydrated, well immersed in a scintillator (Betap, Scint, Wallac), and packaged. Thereafter, activity of the jβ-ray dose was assayed using a liquid scintillation counter (1205 BETAPLATE, Wallac).

The results are shown in FIG. 1. The immunosuppressive activities of HD4, HD6, HD8, and HD10 were more dose-dependent compared with those of the hIgG group, those of HD8, HD4, and HD10 were lower than those of L243, and those of HD6 were equivalent to or higher than those of the positive control antibody L243.

This suggests that HD8, HD4, and HD10 can be used as antibodies having low immunosuppressive activities, and HD6 can be used as an immunosuppressive agent.

EXAMPLE 10

Examination of Reactivity of Each Monoclonal Antibody with HLA-DR-expressing Cells Reactivity of each purified monoclonal antibody obtained in Example 3 with the HLA-DR-expressing L929 cells prepared in Example 1 was analyzed by FCM. The L929 cells and the HLA-DR-expressing L929 cells were suspended in PBS containing 0.1% sodium azide and 1% fetal calf serum (Staining Medium, hereinafter abbreviated to "SM") at $2\times10^7$/mL, and the suspension was fractionated in a 96-well, round-bottom plate at 100 µl/well. After the centrifugation (600 G, 4° C., 2 minutes), the supernatant was removed, the culture supernatant (50 µl) of hybridomas cultured in Example 3 was added, and the mixture was stirred and allowed to stand under ice cooling for 30 minutes. Centrifugation (600 G, 4° C., 2 minutes) was then carried out to remove the supernatant. The pellet was washed twice with 100 µl/well SM, 30 µL of 0.0125 mg/mL RPE fluorescence-labeled rabbit anti-human Igκ $F(ab')_2$ antibody (DAKO) was added thereto, and the resultant was incubated under ice cooling for 30 minutes. After being washed twice with SM, the incubation product was suspended in SM, and the fluorescence intensity of each cell was assayed by FCM.

The results are shown in Table 1 above. All the antibodies exhibited potent binding activities to HLA-DR-expressing L929 cells alone, but none exhibited the binding activity to the L929 cell. This indicates that these antibodies specifically bind to HLA-DR.

EXAMPLE 11

Effect of Purified Human Anti-HLA-DR Monoclonal Antibody on Tumor-bearing Mouse Models The effects of the purified human anti-HLA-DR monoclonal antibody obtained in Example 8 were examined using tumor-bearing mouse models in accordance with a method described below.

First, 5-week-old C.B-17/ICR SCID mice (CLEA Japan, Inc.) were purchased, anti-asialo GM1 antiserum (Wako Chemicals) was diluted, and 10 µL each thereof was intravenously administered to each of the mice when they were 6 weeks old. On the next day, Burkitt's lymphoma cells Raji (ATCC CCL-86) were intravenously administered in amounts of $5\times10^6$ cells per mouse. Five days after the Raji transplantation, the purified human anti-HLA-DR monoclonal antibody was administered once in tail veins of mice in amounts of 0.1 µg or 1 µg per mouse. As an antibody negative control, the same amount of human anti-HSA antibody was used. The survival ratio after the transplantation was observed for about 3 months or longer.

Figure 2B:
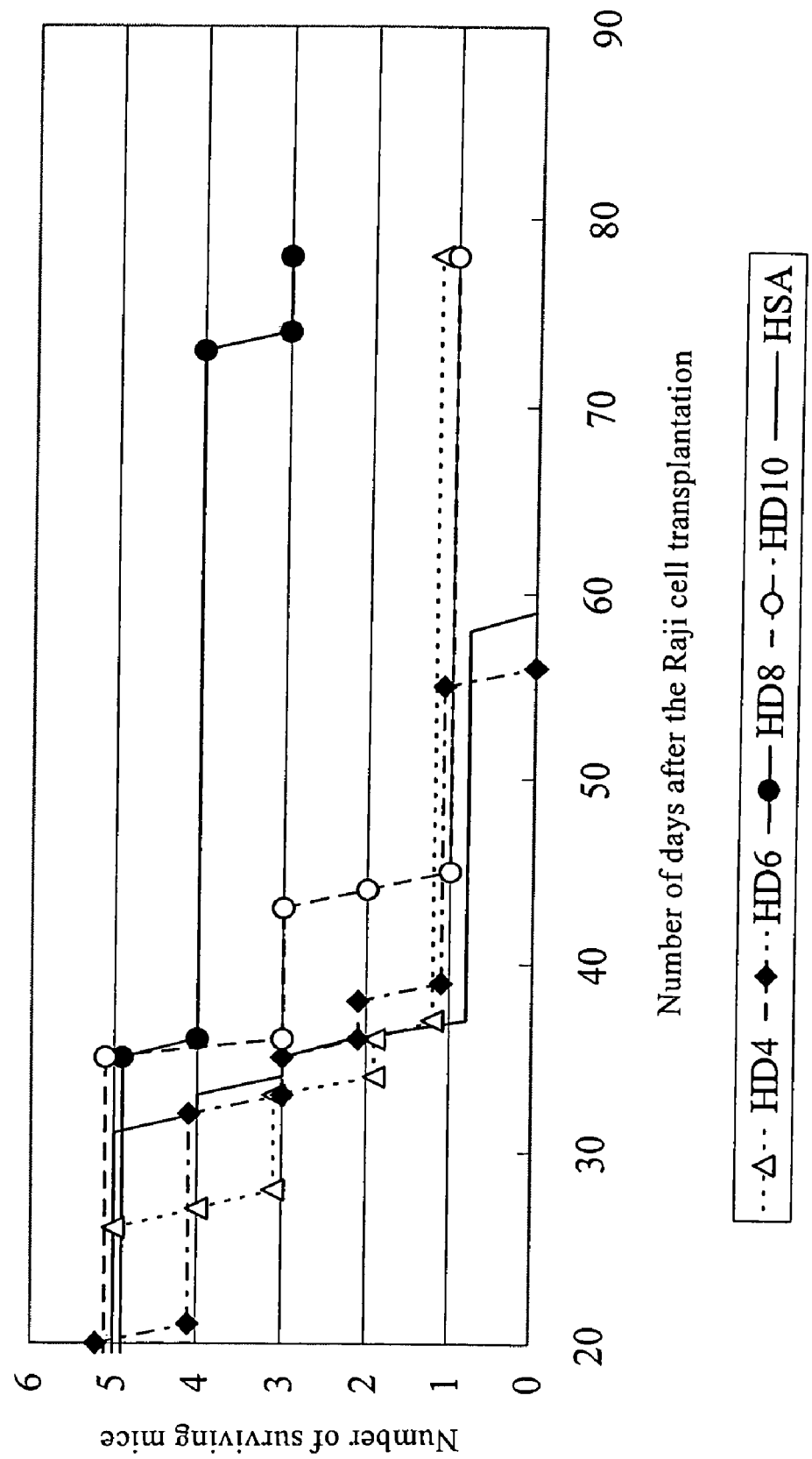
FIG. 2B shows the effects attained when the dose is 0.1 µg/head.

The results of the experiment are shown in FIG. 2. In the group of mice to which the purified human anti-HLA-DR monoclonal antibody was administered in amounts of 0.1 µg per mouse, the number of surviving mice 90 days later was 3 for HD8, and 1 for HD10 and HD4 out of a group of 5 mice (FIG. 2B). In contrast, in the group of mice to which the antibody was administered in amounts of 1.0 µg per mouse, the number of surviving mice was 3 for HD8, 5 for HD10, and 2 for HD 4 out of a group of 5 mice (FIG. 2A). In the negative control group to which the anti-HSA antibody was administered, all mice died within 60 days after the Raji transplantation.

At the time of the antibody administration, the body weight of each mouse was about 20 g. Thus, 0.1 µg and 1 µg per mouse means 5 µg/kg and 50 µg/kg based on body weight, respectively. This revealed that HD8 exhibits an anti-tumor effect at very low dosages. Based on this and the results attained in Example 9 together, HD8 can be said to be an antibody having low immunosuppressive activity and potent anti-tumor activity. This suggests that HD8 can be used as an anti-cancer agent with few side effects.

EXAMPLE 12

Preparation of a Gene Encoding a Monoclonal Antibody and Construction of a Recombinant Antibody-expressing Vector (1) cDNA Cloning of HD4 and HD8 Antibody Genes and Preparation of Expression Vector Hybridomas HD4 and HD8 were cultured in eRDF medium (Kyokuto Seiyaku) containing 10 ng/ml of IL-6 (R & D Systems) and 10% fetal bovine serum (SIGMA) and centrifuged to collect cells. Thereafter, TRIZOL (Gibco BRL) was added thereto, and total RNA was extracted in accordance with the instructions therefor. Cloning of the variable region in the antibody cDNA was carried out using the SMART RACE cDNA amplification Kit (Clontech) in accordance with the attached instruction.

First-strand cDNA was prepared using 5 µg of the total RNA as a template.

1) Synthesis of First-strand cDNA

Total RNA 5 µg/3 µL

5'CDS 1 µL

SMART oligo 1 µL

The reaction solution having the above composition was incubated at 70° C. for 2 minutes, 5× Buffer 2 µL

DTT 1 µL

DNTP mix 1 µL

Superscript II 1 µL were then added, and the mixture was incubated at 42° C. for 1.5 hours.

Further, 100 µL of Tricine Buffer was added, followed by incubation at 72° C. for 7 minutes. Thus, fist-strand cDNA was obtained.

2) Amplification of a Heavy Chain Gene and a Light Chain Gene by PCR and Construction of a Recombinant Antibody-expressing Vector cDNA was amplified using Z-Taq (Takara).
cDNA 2 µL
10×Z-Taq Buffer 5 µL
dNTP mix 4 µL
Z-Taq 1 µL
Primer 1
Primer 2

The final volume of the reaction solution having the above composition was brought to 50 µL with the aid of double distilled water and then subjected to PCR.

The heavy chain was amplified by 30 PCR cycles of 98° C. for 1 second and 68° C. for 30 seconds using UMP (SMART RACE cDNA amplification Kit, Clontech) and the hh-6 primer (5'-GGT CCG GGA GAT CAT GAG GGT GTC CTT-3') (SEQ ID NO: 5). Further, 1 µL of this reaction solution was used as a template, and 20 PCR cycles of 98° C. for 1 second and 68° C. for 30 seconds were repeated using NUMP (SMART RACE cDNA amplification Kit, Clontech) and the hh-3 primer (5'-GTG CAC GCC GCT GGT CAG GGC GCC TG-3') (SEQ ID NO: 6). Thereafter, the amplified PCR product was purified using a PCR purification kit (QIAGEN), and nucleotide sequencing was carried out using hh-4 (5'-GGT GCC AGG GGG AAG ACC GAT GG-3') (SEQ ID NO: 7) as a primer. Based on the sequence information, the HD4 heavy chain specific primer tnHD4Sal (5'-ata tgt cga cCC AGC CCT GGG ATT TTC AGG TGT TTT C-3') (SEQ ID NO: 8) and the HD8 heavy chain specific primer tnHD8Sal (5'-ata tgt cga cTGG CTG ACC AGG GCA GTC ACC AGA G-3') (SEQ ID NO: 9) were synthesized, and the resultant primer was used to determine the sequence also from the opposite direction. PCR was carried out using a specific primer and tnCHNhe (5'-gat ggg ccc ttg gtg cta gct gag gag acg g-3') (SEQ ID NO: 10) (98° C. for 1 second, 60° C. for 30 seconds, and 72° C. for 30 seconds), the amplified cDNA fragment of the heavy chain was digested with SalI and NheI, and introduced into the N5KG1-Val Lark vector (a modified vector of IDEC Pharmaceuticals, N5KG1 (U.S. Pat. No. 6,001,358)) that was cleaved with the same enzyme. The inserted sequence was confirmed to be identical to the one identified by direct sequencing by identifying the sequence using the vector as a template.

The light chain was amplified by repeating 30 PCR cycles of 98° C. for 1 second and 68° C. for 30 seconds using UMP (SMART RACE cDNA amplification Kit, Clontech) and the hk-2 primer (5'-GTT GAA GCT CTT TGT GAC GGG CGA GC-3') (SEQ ID NO: 11). Further, 1 µL of this reaction solution was used as a template, and 20 PCR cycles of 98° C. for 1 second and 68° C. for 30 seconds were repeated using NUMP (SMART RACE cDNA amplification Kit, Clontech) and hk-6 (5'-TGGC GGG AAG ATG AAG ACA GAT GGT G-3') (SEQ ID NO: 12). Thereafter, the amplified PCR product was purified using a PCR purification kit (QIAGEN), and nucleotide sequencing was carried out using the hk-6 primer (SEQ ID NO: 12). Based on the sequence information, the HD4 light chain specific primer tnHD4Bgl (5'-ata tag atc tGC TGC TCA GTT AGG ACC CAG AGG GAA CC-3') (SEQ ID NO: 13) and the HD8 light chain specific primer tnHD8Bgl (5'-ata tag atc tGG GAG TCA GAC CCA CTC AGG ACA CAG C-3') (SEQ ID NO: 14) were synthesized, and the resultant primer was used to determine the sequence also from the opposite direction. PCR was carried out using a specific primer and tnCkBsi (5'-aag aca gat ggt gca gcc acc gta cgt ttg at-3') (SEQ ID NO: 15) (98° C. for 1 second, 60° C. for 30 seconds, and 72° C. for 30 seconds), the amplified cDNA fragment of the light chain was digested with BglII and BsiWI and introduced into the N5KG1-Val Lark vector that was cleaved with the same enzyme. The inserted sequence was confirmed to be identical to the one identified by direct sequencing by identifying the sequence using the vector as a template.

DNAs encoding the variable region of the heavy chain, that of the light chain of HD4, amino acid sequences of the variable region of the heavy chain, and that of the light chain of HD4 are shown below.

<The Variable Region of the Heavy Chain of HD4> (SEQ ID NO: 16)

GTCGACCCAGCCCTGGGATTTTCAGGTGTTTTCAGGTGTTTTCATTTGGT

GATCAGGACTGAACAGAGAGAACTCACC<u>ATG</u>GAGTTTGGGCTGAGCTGGC

TTTTTCTTGTGGCTATTTTAAAAGGTGTCCAGTGTGAGGTGCAACTGTTG

GAGTCTGGGGGAGGCTTGGTACAGCCTGGGGGGTCCCTGAGACTCTCCTG

TGCAGCCTCTGGATTCACCTTTAGCAGCTATGCCATGACCTGGGTCCGCC

AGGCTCCAGGGAAGGGGCTGGAGTGGGTCTCAGGTATTAGTGGTGGTGGT

GATAGCACATACTACGCAGACTCCGTGAAGGGCCGGTTCACCATCTCCAG

AGACAATTCCAAGAACACGCTGTATCTGCAAATGAACAGCCTGAGAGCCG

AGGACACGGCCGTATATTACTGTGCGAGAGATCATGGTTCGGGGAGTTAT

TATCCCTACTGGTTTGACTACTGGGGCCAGGGAACCCTGGTCACCGTCTC

CTCAGCTAGC

<The Variable Region of the Heavy Chain of HD4> (SEQ ID NO: 17)

MEFGLSWLFLVAILKGVQC<u>EVQL</u>LESGGGLVQPGGSLRLSCAASGFTFSS

YAMTWVRQAPGKGLEWVSGISGGGDSTYYADSVKGRFTISRDNSKNTLYL

QMNSLRAEDTAVYYCARDHGSGSYYPYWFDYWGQGTLVTVSSA

<The Variable Region of the Light Chain of HD4> (SEQ ID NO: 18)

AGATCTGCTGCTCAGTTAGGACCCAGAGGGAACC<u>ATG</u>GAAACCCCAGCGC

AGCTTCTCTTCCTCCTGCTACTCTGGCTCCCAGATACCACCGGAGAACTT

GTGTTGACGCAGTCTCCAGGCACCCTGTCTTTGTCTCCAGGGGAAAGAGC

CACCCTCTCCTGCAGGGCCAGTCAGAGTGTTAGCAGCCGCTACTTAGCCT

GGTACCAGCAGAAACCTGGCCAGGCTCCCAGGCTCCTCATCTATGGTGCA

TCCAGCAGGGCCACTGGCATCCCAGACAGGTTCAGTGGCAGTGGGTCTGG

GACAGACTTCACTCTCACCATCAGCAGACTGGAGCCTGAAGATTTTGCAG

TGTATTACTGTCAGCAGTATGGTAGCTCACCGCTCACTTTCGGCGGAGGG

ACCAAGGTGGAGATCAAACGTACG

<The Variable Region of the Light Chain of HD4> (SEQ ID NO: 19)

METPAQLLFLLLLWLPDTTG<u>ELVL</u>TQSPGTLSLSPGERATLSCRASQSVS

SRYLAWYQQKPGQAPRLLIYGASSRATGIPDRFSGSGSGTDFTLTISRLE

PEDFAVYYCQQYGSSPLTFGGGTKVEIKRT

The translation initiation site in the heavy chain DNA is the ATG codon starting from the 79th adenine (A) from the 5'-terminus of the sequence as shown in SEQ ID NO: 16, and the boundary between the variable region and the constant region of the antibody is located between the 504th adenine (A) and the 505th guanine (G) from the 5'-terminus. In the amino acid sequence, the variable region of the heavy chain is a portion between the N-terminus and the 142nd serine (S) residue in the sequence as shown in SEQ ID NO: 17, and a portion comprising the 143rd alanine (A) and thereafter is the constant region. The N-terminus of the purified heavy chain protein was analyzed. This demonstrated that the signal sequence of the heavy chain was a portion between the N-terminus and the 19th cysteine (C) of the sequence as shown in SEQ ID NO: 17, and the N-terminus of the matured body was the 20th glutamic acid (E) of the sequence as shown in SEQ ID NO: 17. Accordingly, the matured portion in the amino acid sequence as shown in SEQ ID NO: 17 is a portion between the 20th glutamic acid and the 142nd serine.

The translation initiation site in the light chain DNA is the ATG codon starting from the 35th A from the 5'-terminus of the sequence as shown in SEQ ID NO: 18, and the variable region is the portion between the 5'-terminus and the 418th adenine (A). In the amino acid sequence, the variable region is the portion between the N-terminus and the 128th lysine (K) of the sequence as shown in SEQ ID NO: 19. The N-terminus of the purified light chain protein was analyzed. This demonstrated that the signal sequence of the light chain was the portion between the N-terminus and the 20th glycine (G) of the sequence as shown in SEQ ID NO: 19, and the N-terminus of the matured body was the 21st glutamic acid (B) of the sequence as shown in SEQ ID NO: 19. Accordingly, the matured portion in the amino acid sequence as shown in SEQ ID NO: 19 is the portion between the 21st glutamic acid and the 128th lysine.

DNAs encoding the variable region of the heavy chain, that of the light chain of HD8, amino acid sequences of the variable region of the heavy chain, and that of the light chain of HD8 are shown below.

<The Variable Region of the Heavy Chain of HD8> (SEQ ID NO: 20)

GTCGACTGGCTGACCAGGGCAGTCACCAGAGCTCCAGACA<u>ATG</u>TCTGTCT

CCTTCCTCATCTTCCTGCCCGTGCTGGGCCTCCCATGGGGTGTCCTGTCA

CAGGTTCAGCTGCAGCACTCAGGTCCAGGACTGGTGAAGCCCTCGCAGAC

CCTCTCACTCACCTGTGCCATCTCCGGGGACAGTGTCTCTAGCAACAGTG

CTTCTTGGAACTGGATCAGGCAGTCCCCATCGAGGGGCCTTGAGTGGCTG

GGAAGGACATACTACAGGTCCAAGTGGTATAATGATTATGCAGTATCTGT

GAAAAGTCGAATAGTCATCAACCCAGACACATCCAAGAACCAGTTCTCCC

TGCAGCTGAACTCTGTGACTCCCGAGGACACGGCTGTGTATTACTGTGCG

AGAGAAAATTTCTATGGTTCGGAGACTTGTCATAAGAAGTATTACTGCTA

CGGTATGGACGTCTGGGGCCAAGGGACCACGGTCACCGTCTCCTCAGCTA

GC

<The Variable Region of the Heavy Chain of HD8> (SEQ ID NO: 21)

MSVSFLIFLPVLGLPWGVLSQ<u>VQL</u>QHSGPGLVKPSQTLSLTCAISGDSVS

SNSASWNWIRQSPSRGLEWLGRTYYRSKWYNDYAVSVKSRIVINPDTSKN

QFSLQLNSVTPEDTAVYYCARENFYGSETCHKKYYCYGMDVWGQGTTVTV

SSAS

<The Variable Region of the Light Chain of HD8> (SEQ ID NO: 22)

AGATCTGGGAGTCAGACCCACTCAGGACACAGC<u>ATG</u>GACATGAGGGTCCC

CGCTCAGCTCCTGGGGCTTCTGCTGCTCTGGCTCCCAGGTGCCAGATGTG

CCATCCAGTTGACCCAGTCTCCATCCTCCCTGTCTGCATCTGTAGGAGAC

AGAGTCACCATCACTTGCCGGGCAAGTCAGGGCATTAGCAGTGCTTTAGC

CTGGTATCAGCAGAAACCAGGGAAAGCTCCTAAACTCCTGATCTATGATG

CCTCCAGTTTGGAAAGTGGGGTCCCATCAAGGTTCAGCGGCAGTGGATCT

GGGACAGATTTCACTCTCACCATCAGCAGCCTGCAGCCTGAAGATTTTGC

AACTTATTACTGTCAACAGTTTAATAGTTTCCCGCTCACTTTCGGCGGAG

GGACCAAGGTGGAGATCAAACGTACG

<The Variable Region of the Light Chain of HD8> (SEQ ID NO: 23)

MDMRVPAQLLGLLLLWLPGARC<u>AIQL</u>TQSPSSLSASVGDRVTTTCRASQG

ISSALAWYQQKPGKAPKLLIYDASSLESGVPSRFSGSGSGTDFTLTISSL

QPEDFATYYCQQFNSFPLTFGGGTKVEIKRTV

The translation initiation site in the heavy chain DNA is the ATG codon starting from the 41st adenine (A) from the 5'-terminus of the sequence as shown in SEQ ID NO: 20, and the boundary between the variable region and the constant region of the antibody is located between the 496th adenine (A) and the 497th guanine (G) from the 5'-terminus. In the amino acid sequence, the variable region of the heavy chain is the portion between the N-terminus and the 152nd serine (S) residue in the sequence as shown in SEQ ID NO: 21, and the portion comprising the 153rd alanine (A) and thereafter is the constant region. The N-terminus of the purified heavy chain protein was analyzed. This demonstrated that the signal sequence of the heavy chain was the portion between the N-terminus and the 20th serine (S) of the sequence as shown in SEQ ID NO: 21, and the N-terminus of the matured body was the 21st glutamine (Q) of the sequence as shown in SEQ ID NO: 21. Accordingly, the matured portion in the amino acid sequence as shown in SEQ ID NO: 21 is the portion between the 21st glutamine and the 152nd serine.

The translation initiation site in the light chain DNA is the ATG codon starting from the 34th A from the 5'-terminus of the sequence as shown in SEQ ID NO: 22, and the variable region is the portion between the 5'-terminus and the 420th adenine (A). In the amino acid sequence, the variable region is the portion between the N-terminus and the 129th lysine (K) of the sequence as shown in SEQ ID NO: 23. The N-terminus of the purified light chain protein was analyzed. This demonstrated that the signal sequence of the light chain is the portion between the N-terminus and the 22nd cysteine (C) of the sequence as shown in SEQ ID NO: 23, and the N-terminus of the matured body was the 23rd alanine (A) of the sequence as shown in SEQ ID NO: 23. Accordingly, the matured portion in the amino acid sequence as shown in SEQ ID NO: 23 is the portion between the 23rd alanine and the 129th lysine.

TABLE 2

Nucleotide sequences of synthetic DNA

| No | Primer | Sequence (5' to 3') | Length | SEQ ID NO. |
|---|---|---|---|---|
| 1 | hh-6 | GGT CCG GGA GAT CAT GAG GGT GTC CCT | 27 | 5 |
| 2 | hh-3 | GTG CAC GCC GCT GGT CAG GGC GCC TG | 26 | 6 |
| 3 | hh-4 | GGT GCC AGG GGG AAG ACC GAT GG | 23 | 7 |
| 4 | tnHD4Sal | ata tgt cga cCC AGC CCT GGG ATT TTC AGG TGT TTT C | 37 | 8 |
| 5 | tnHD8Sal | ata tgt cga cTGG CTG ACC AGG GCA GTC ACC AGA G | 35 | 9 |
| 6 | tnCHNhe | gat ggg ccc ttg gtg cta gct gag gag acg g | 31 | 10 |
| 7 | hk-2 | GTT GAA GCT CTT TGT GAC GGG CGA GC | 26 | 11 |
| 8 | hk-6 | T GGC GGG AAG ATG AAG ACA GAT GGT G | 26 | 12 |
| 9 | tnHD4Bgl | ata tag atc tGC TGC TCA GTT AGG ACC CAG AGG GAA CC | 38 | 13 |
| 10 | tnHD8Bgl | ata tag atc tGG GAG TCA GAC CCA CTC AGG ACA CAG C | 37 | 14 |
| 11 | tnCkBsi | aag aca gat ggt gca gcc acc gta cgt ttg at | 32 | 15 |

EXAMPLE 13

Preparation of Subclass Recombinant Vectors

Figure 3A:
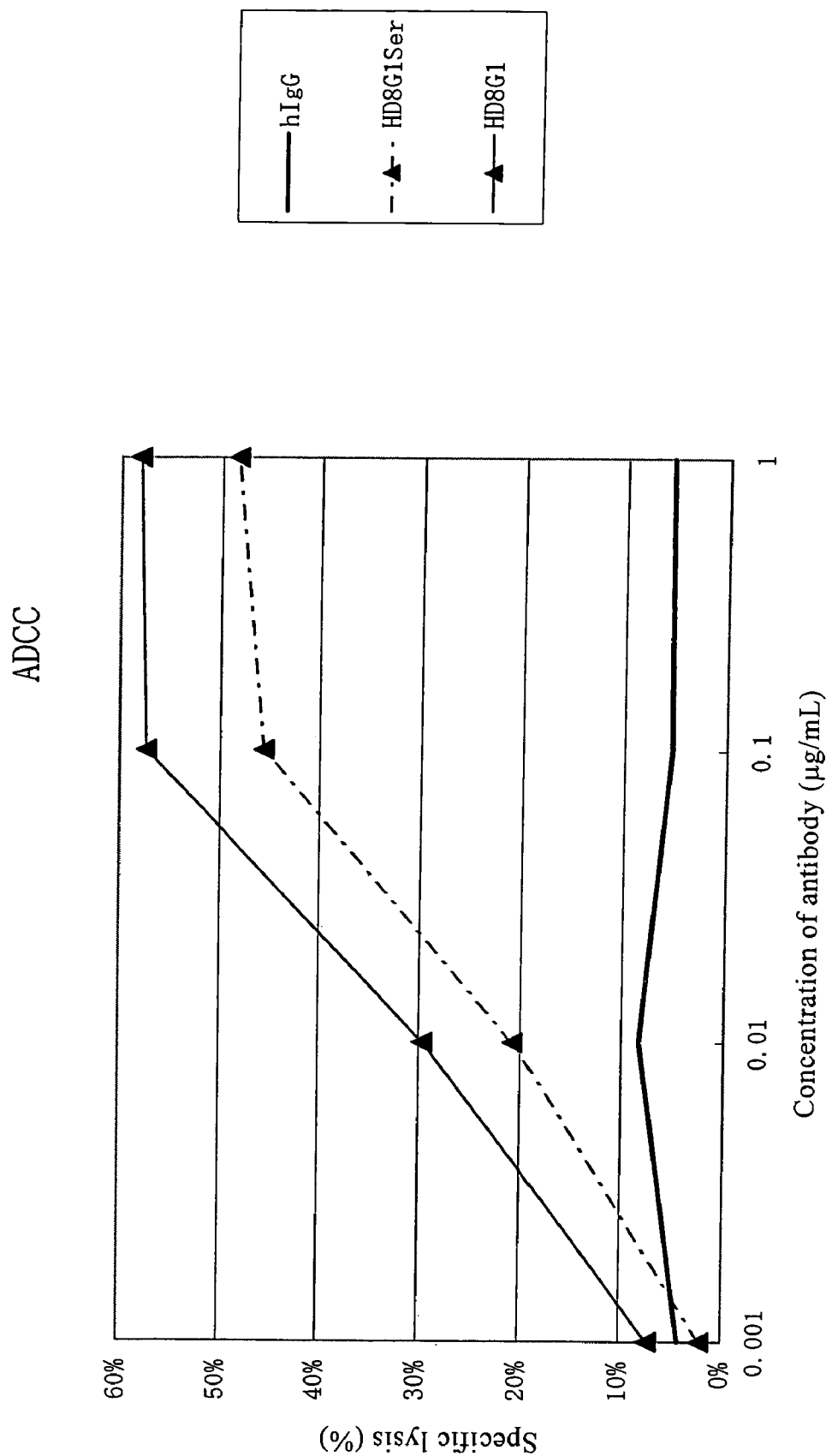
FIG. 3A shows the ADCC activities of HD8G1Ser and HD8G1.
Figure 3D:
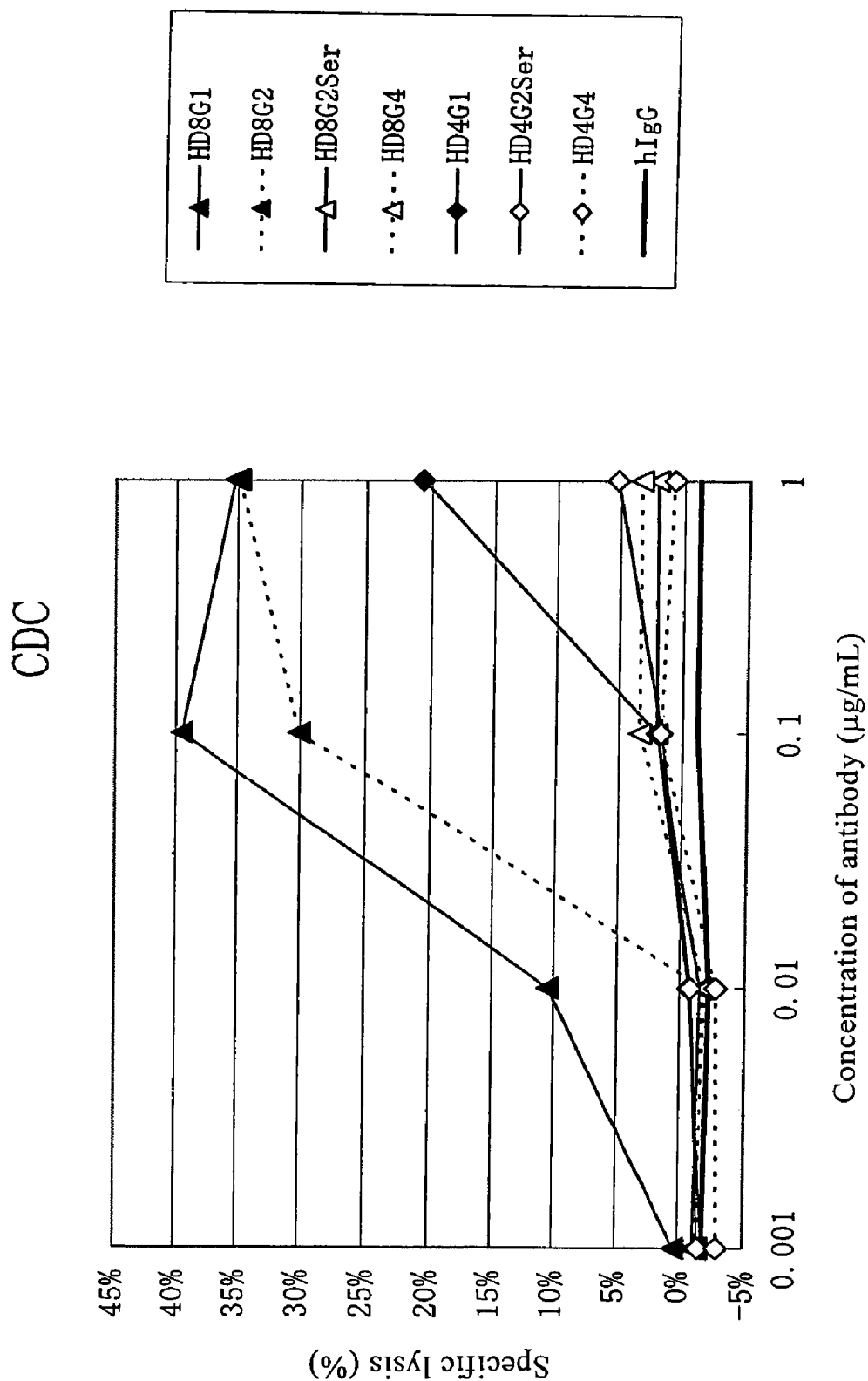
FIG. 3D shows the CDC activities of HD8G1, HD8G2, HD8G2Ser, HD8G4, HD4G1, HD4G2Ser, and HD4G4.

The variable regions of the HD4 and HD8 antibodies were incorporated into the following variety of vectors. The N5KG1-Val Lark vector was used for the IgG1 type, the N5KG4 Lark vector was used for the IgG4 type (both vectors were manufactured by IDEC Pharmaceuticals, modified vectors of N5KG1 were disclosed in U.S. Pat. No. 6,001,358, N5KG1-Val Lark was modified while sustaining IgG1 as with N5KG1, and N5KG4 Lark was rearranged to the IgG4 type), a vector in which the constant region of the heavy chain of the N5KG1-Val Lark was rearranged into the IgG2 type (N5KG2) was used for the IgG2 type, and the variable regions of HD4 and HD8 were incorporated into the vector in the same manner as in Example 12. Separately, a vector in which the sequence CCC encoding proline (P) 331 according to the EU numbering system in the constant region of the heavy chain that was incorporated into the IgG1 or IgG2 vector was varied to TCC encoding serine (S) (Mi-Hua Tao et al., 1993, J. Exp. Med.) was prepared (hereafter referred to as N5KG1Ser and N5KG2Ser in that order), and the variable regions of HD4 and HD8 were incorporated into the vector in the same manner as in Example 12. In FIG. 3 and Table 3 below, for example, the HD4 antibody having an IgG1 subclass is referred to as HD4IgG1 or HD4G1, and the antibody that expresses the gene in which the sequence CCC encoding proline (P) 331 according to the EU numbering system in the constant region of the heavy chain was varied to TCC encoding serine (S) is referred to as HD4IgG1Ser or HD4G1Ser.

TABLE 3

Names of recombinant vectors and produced recombinant antibodies

Recombinant antibody and its cytotoxic activity

| Antibody | Vector | Subclass | Recombinant antibody | ADCC activity | CDC activity |
|---|---|---|---|---|---|
| HD4 | N5KG1-Val Lark | IgG1 | HD4G1 | + | + |
| HD4 | N5KG2Ser | IgG2Ser | HD4G2Ser | − | − |
| HD4 | N5KG4 Lark | IgG4 | HD4G4 | − | − |
| HD8 | N5KG1-Val Lark | IgG1 | HD8G1 | + | + |
| HD8 | N5KG1Ser | IgG1Ser | HD8G1Ser | + | − |
| HD8 | N5KG2 | IgG2 | HD8G2 | − | + |
| HD8 | N5KG2Ser | IgG2Ser | HD8G2Ser | − | − |
| HD8 | N5KG4 Lark | IgG4 | HD8G4 | − | − |

EXAMPLE 14

Preparation of Recombinant Antibody

The recombinant antibody-expressing vectors constructed in Examples 12 and 13 were introduced into host cells to prepare a recombinant antibody-expressing cell. Examples of host cells for expression that can be used include dhfr-deficient CHO cells (ATCC CRL-9096), CHO-Ras (Katakura Y., et al., Cytotechnology, 31: 103–109, 1999), and HEK293T (ATCC CRL-11268).

Vectors were introduced into host cells by electroporation, lipofection, or the like. Electroporation was carried out linearizing about 2 μg of an antibody-expressing vector with a restriction enzyme, introducing the genes into $4 \times 10^6$ CHO cells using Bio-Rad electrophoreter at 350 V and 500 μF, and sowing them on a 96-well culture plate. Lipofection was carried out using LipofectAMINE Plus (Gibco BRL) in accordance with the instructions therefor. After introducing the vectors, an agent that corresponds to the selection marker for the expression vector was added, and the culture was continued. After the colonies were confirmed, the antibody-expressing cells were selected by the method described in Example 4. Antibodies were purified from the selected cells in accordance with Example 8.

EXAMPLE 15

Examination of Cytotoxic Activity

Cytotoxic activities through an antibody were assayed. These activities comprised cytotoxic activity on the target cell in the presence of the NK cell or a cell with killer activity such as a neutrophil and an antibody, i.e., antibody-dependent cellular cytotoxicity (ADCC), and cytotoxic activity on the target cell in the presence of a complement and an antibody, i.e., complement-dependent cytotoxicity (CDC). The hybridoma-derived HD4 and HD8 antibodies prepared in Example 8 and recombinant antibodies derived from each of the CHO cells prepared in Example 14 were used. In this case, hIgG was used as a control.

In simple terms, radioactive chromium ($Cr^{51}$) was incorporated into the cytoplasm of the target cell, and the amount of $Cr^{51}$ released in the culture solution due to the cell death was measured based on the γ dose.

More specifically, $10^6$ Burkitt's lymphoma cells, Raji (ATCC CCL-86), as the target cells were suspended in 15 μL of fetal calf serum (FCS), 50 μL (37 MBq/mL) of $Cr^{51}$-labeled sodium chromate (Perkin Elmer, hereafter referred to as "$Cr^{51}$") was added, and culture was then conducted at 37° C. for 1 hour. Subsequently, 10 mL of medium was added, centrifugation was carried out, and the medium was discarded. This procedure was repeated three times to remove $Cr^{51}$ that was not incorporated in the cell.

In the ADCC assay, 200,000 mononuclear cells, which were derived from the peripheral blood of a healthy person obtained by the method described in Example 6, relative to 2,000 $Cr^{51}$-labeled target cells (total volume: 200 μL) were cultured in a round-bottom, 96-well plate (Falcon) together with antibodies at each concentration level at 37° C. in the presence of 5% $CO_2$ for 4 hours.

In the CDC assay, human serum-derived complements (final concentration: 5%, SIGMA) relative to 2,000 $Cr^{51}$-labeled target cells (total volume: 200 μL) were cultured in a round-bottom, 96-well plate together with antibodies at each concentration level at 37° C. in the presence of 5% $CO_2$ for 2 hours.

In both of the ADCC and CDC assays, the plate was subjected to centrifugation after the culture in order to deposit cells. Thereafter, 50 μL of supernatant was transferred to a powder scintillator-containing 96-well plate (Lumaplate™-96, Packard) and dehydrated at 55° C. for 1.5 hours. After confirming the dehydration, the plate was covered with a dedicated-purpose cover (TopSeal™-A, 96-well Microplates, Packard), and the γ dose was measured using a scintillation counter (TopCount, Packard).

The results are shown in FIG. 3 and Table 3. HD8IgG1Ser, HD8IgG2Ser, HD8IgG4, HD4G2Ser, and HD4G4 had no CDC activity, and HD8IgG1, HD8IgG2, and HD4G1 had CDC activity. Only HD8IgG1, HD8IgG1Ser, and HD4G1 had ADCC activity.

EXAMPLE 16

Effects of Recombinant Antibody on Tumor-bearing Mouse Model

Similar models as used in Example 11 were used to examine the pharmacological function of the HD8 recombinant antibody using tumor-bearing mouse models.

At the outset, 5-week-old C.B-17/ICR-SCID mice (CLEA Japan, Inc.) were purchased, anti-asialo GM1 antiserum (Wako Chemicals) was diluted, and 10 μL each thereof was intravenously administered to each of the mice when they were 6 weeks old. On the next day, Burkitt's lymphoma cells Raji (ATCC CCL-86) were intravenously administered in amounts of $5 \times 10^6$ cells per mouse. Three days after the Raji transplantation, each antibody was administered once in tail veins of mice in amounts of 0.1 μg or 1 μg per mouse. The number of surviving mice after the transplantation was observed.

The HD8G1Ser and HD8G2Ser prepared in Example 14 were administered once in amounts of 0.1 or 1 μg per mouse. As an antibody negative control, a group of mice to which the hIgG antibody used as a negative control in Example 9 was administered at 1 μg/head was provided. As a positive control, a group of mice to which HD8G1 was administered at 1 μg/mouse was provided.

Figure 4A:
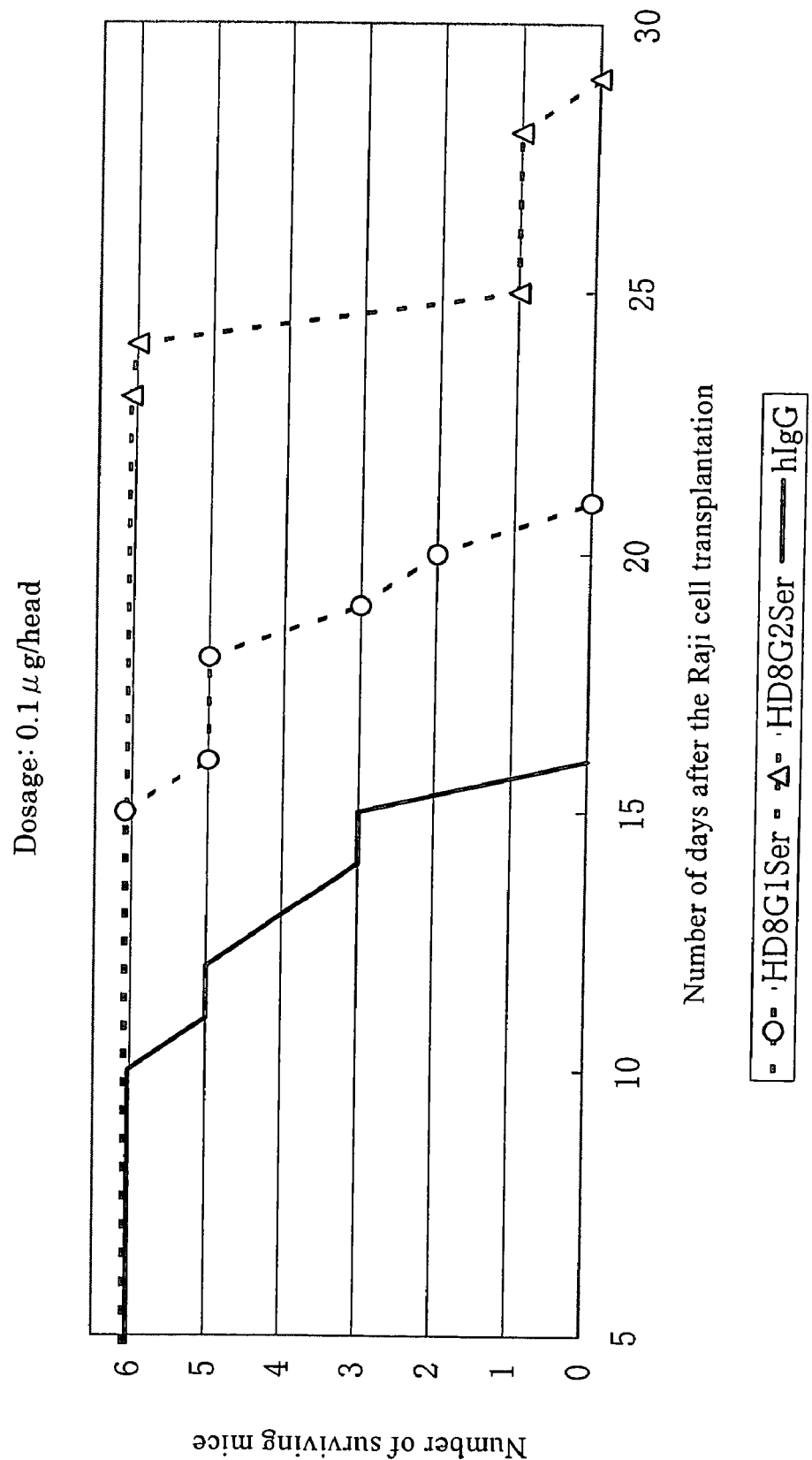
FIG. 4A shows the results attained when the dose is 0.1 µg per mouse.

The results of the above experiment are shown in FIG. 4. All the samples died within 16 days after the Raji transplantation in the negative control, i.e., the hIgG-administered group. The number of surviving mice 20 days later is as follows. With the administration of 1 μg per mouse, all 6 samples survived except for the hIgG group (FIG. 4A), and with the administration of 0.1 μg per mouse, all 6 samples in the HD8G2Ser group and 2 samples in the HD8G1Ser group survived (FIG. 4B). The number of surviving mice 25 days later is as follows. With the administration of 1 μg per mouse, 2 mice in the HD8G1Ser group, 1 mouse in the HD8G1 group, and 4 mice in the HD8G2Ser group survived (FIG. 4A), and with the administration of 0.1 μg per mouse, 1 mouse only in the HD8G2Ser group survived (FIG. 4B).

These results demonstrated that the HD8 recombinant antibodies, HD8G1Ser and HD8G2Ser, also exhibited antitumor effects at very low dosages as with HD8. Although HD8G2Ser had neither of ADCC or CDC activity, it exhibited beneficial effects on animal models.

EXAMPLE 17

Epitope Analyses of HD4, HD6, and HD8

The epitope of each antibody was analyzed by Western blotting in accordance with a conventional technique. In simple terms, a cellulose or PVDF membrane was blocked with Block Ace (Yukijirushi), etc., each antibody was allowed to react therewith at 1 μg/mL as a primary antibody and at 0.5 μg/mL as a secondary antibody using HRP conjugated anti rabbit IgG (DAKO), the HRP-labeled anti-human antibody (e.g., DAKO) was allowed to react therewith, and the chemiluminescence was detected using a chemiluminescent reagent (e.g., ECL Western blotting detection reagent, Amersham Bioscience) and a chemiluminescence detector (e.g., LAS-1000, Fuji Film).

(1) A membrane fraction was extracted from the HLA-DR-expressing lymphoma cell SKW 6.4 (ATCC TIB-215), and the HLA-DR protein was purified from the anti-HLA-DR antibody (K28N, the name of produced cell: mouse-mouse hybridoma K28, deposited internationally at the International Patent Organism Depositary of the National Institute of Advanced Industrial Science and Technology (Tsukuba Central 6, 1-1-1 Higashi, Tsukuba, Ibaraki, Japan) as of Feb. 22, 1994 under the accession number of FERM BP4577) using an affinity column. The obtained protein was boiled using 4–20% gradient gel (Daiichi Pure Chemicals Co., Ltd.) under nonreducing conditions (95° C., 5 minutes), electrophoresis was carried out at a constant current of 25 mA for 1.5 hours per gel, and the resultant was transferred to a PVDF membrane at a constant current of 150 mA for 1 hour per gel. Subsequently, Western blot analysis was carried out in accordance with a conventional technique, and as a result, all of HD4, HD6, and HD8 were found to recognize the HLA-DR β chain located at approximately 30 Kda.

(2) Subsequently, regarding 199 amino acids in the extracellular region of the HLA-DR β chain (DRB1*15011) (199 amino acids from amino acids 29 to 227 in the amino acid sequence as shown in SEQ ID NO: 147 and the nucleotide sequence encoding the amino acid sequence as shown in SEQ ID NO: 147 is shown in SEQ ID NO: 146), 94 types of peptides in total (SEQ ID NOs: 52 to 145) were spot synthesized from the C terminus on the cellulose membrane by shifting two amino acids in the 13-mer peptides, and the N terminus was acetylated (JERINI Germany). The subsequent reaction was carried out based on conventional Western blot analysis (see, for example, Reineke, U. et al., (2001), "Epitope mapping with synthetic peptides prepared by SPOT synthesis." Antibody Engineering (Springer Lab Manual) Eds.: Kontermann/Dubel, 433–459). In the analysis, LumilmagerTM (Boehringer-Mannheim) was used to represent the color intensity in each spot by numerical values.

Figure 5A:
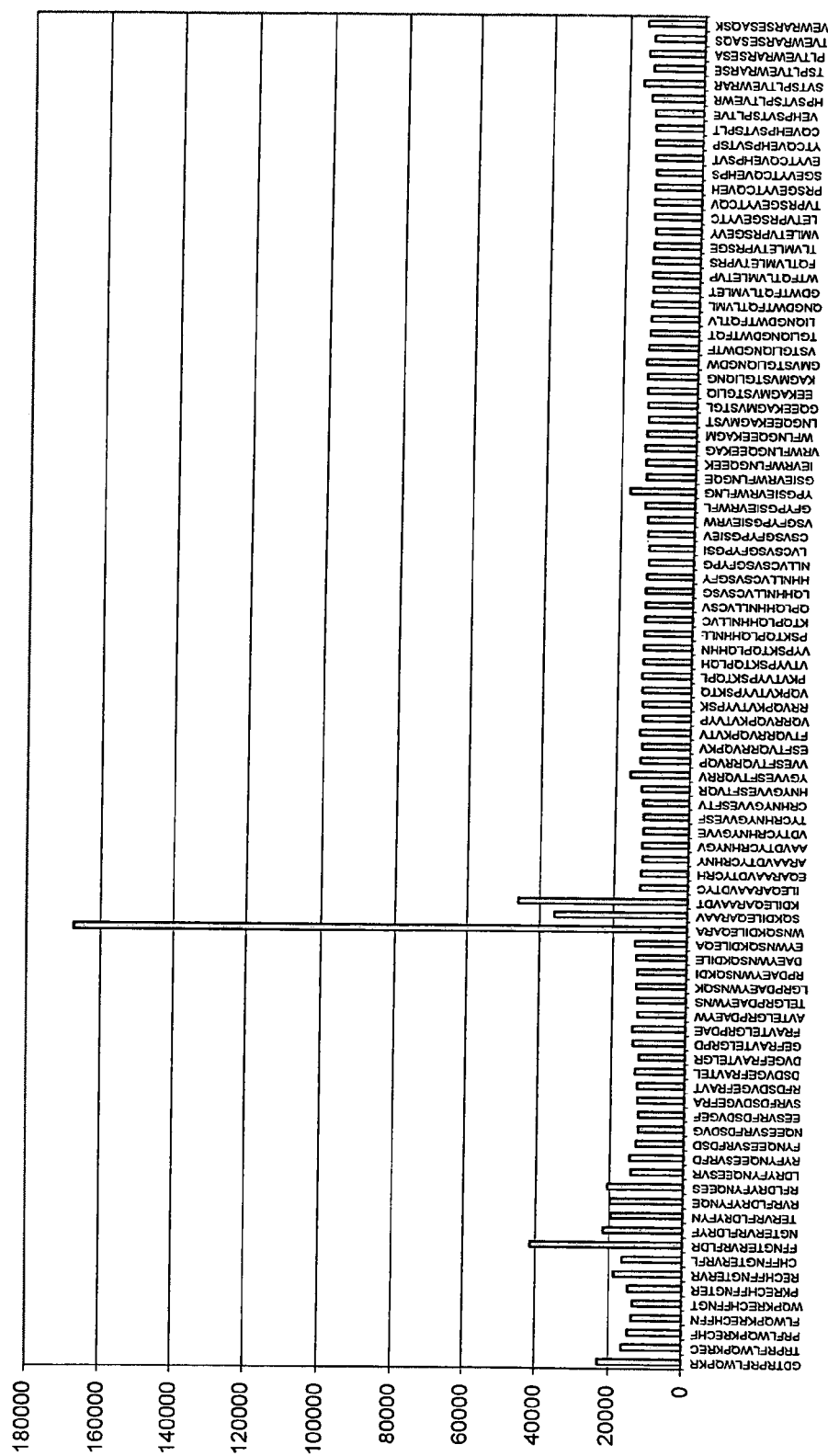
FIGS. 5A, 5B, and 5C show analyses on HD4, HD6, and HD8, respectively.
Figure 5B:
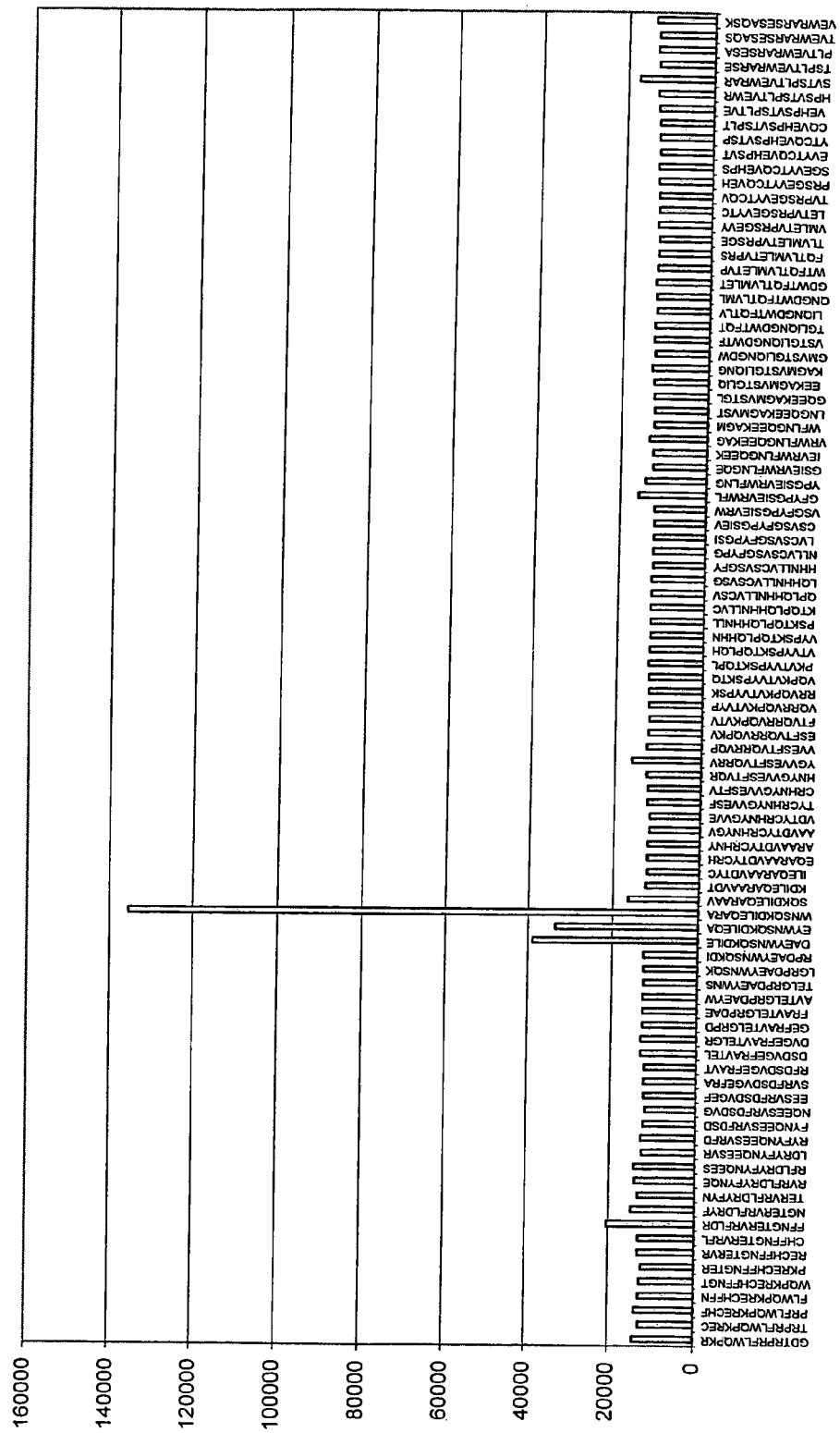
Figure 5C:
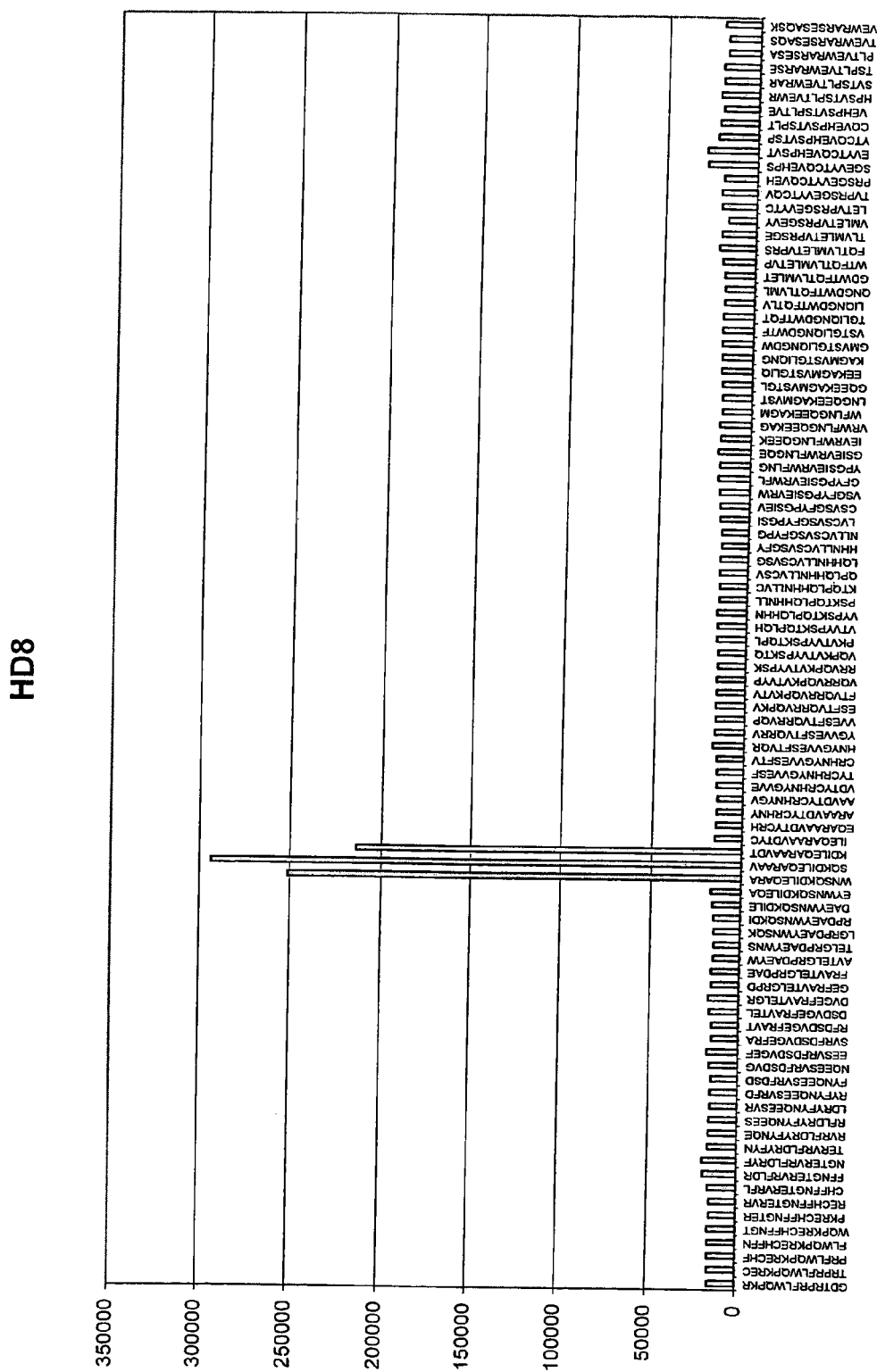

The results are shown in FIG. 5. HD4 (FIG. 5A) exhibited potent reactivity with amino acids 61 to 73 and low reactivity with amino acids 17 to 29, 63 to 75, and 65 to 77, and maximally bound to a peptide having the amino acid sequence as shown in SEQ ID NO: 82. HD6 (FIG. 5B) exhibited potent reactivity with amino acids 61 to 73 and low reactivity with amino acids 57 to 69 and 59 to 71, and maximally bound to a peptide having the amino acid sequence as shown in SEQ ID NO: 82. HD8 (FIG. 5C) exhibited very potent reactivity with amino acids 61 to 73, 63 to 75, and 65 to 77 and potently bound to at least one peptide having the amino acid sequences as shown in SEQ ID Nos: 82, 83, and 84. In contrast, based on the conformation of HLA-DR (see, for example, Dessen A et al., Immunity (1997), 7, 473–481), amino acids 61 to 73 form the a helix structure at the site where antigen-presenting peptides are retained.

(3) The β-chain polymorphisms of the 13 amino acids (amino acids 61 to 73) that exhibit maximal reactivity with all of HD4, HD6, and HD8 were taken into consideration, and 16 types of peptides including substantially almost all of the currently known about 350 types of polymorphisms (see the IMGT/HLA database of EMBL-EBI, etc.) were prepared. Further, 12 peptides (SEQ ID Nos: 40 to 51) in which each amino acid has been substituted with alanine (guanidine if it is originally alanine) were subjected to Western blotting under similar conditions. In the analysis, LAS2000 and ImageGauge analyzing software (Fuji Photo Film) were used to represent the color intensity in each spot by numerical values. FIG. 6 shows 28 types of peptide sequences and their reactivity with HD4, HD6, and HD8. The sequence to which each antibody positively reacted was represented by + to ++++ depending on its intensity, and represented by − in case of negative reactivity.

Positive or negative reaction was judged in accordance with the following criteria.
Less than 5% of the background: −
5% to less than 10% of the background: +/−
10% to less than 20% of the background: +
20% to less than 30% of the background: ++
30% to less than 50% of the background: +++
50% or more of the background: ++++

HD8 positively reacted with all sequences except for those as shown in SEQ ID Nos: 48 to 51 in which amino acids 65, 66, 69, and 72 had been substituted with alanine. The amino acids 65, 66, 69, and 72 are conserved in substantially almost all of the discovered HLA-DR β chains (see the IMGT/HLA database of EMBL-EBI, etc.) Since they cover most of the HLA-DR β chain sequences including major sequences among those as shown in SEQ ID Nos: 24 to 39, HD8 is very highly likely to be a Pan-HLA-DR antibody that binds to substantially almost all the HLA-DR β chains.

Furthermore, reactivity of HD8 was examined using the HLA-DR positive cell strain in the same manner as in Example 10. As a result, it was found to react with ARH77 (ATCC CRL-1621), Daudi (ATCC CCL-213), HS-Sultan (ATCC CRL-1484), IM-9 (ATCC CCL-159), MC/CAR (ATCC CRL-8083), Raji (ATCC CCL-86), Ramos (ATCC CRL-1596), RL (ATCC CRL-2261), SKW6.4 (ATCC TIB-215), and the L-cell (ATCC CCL-1) in which DRB1*15011/DRA*0101 were forcibly expressed and 5 specimens of human peripheral blood mononuclear cells derived from a healthy Japanese person. It has not yet been discovered in a cell in which nonreactive HLA-DR is expressed. Further, it reacts with 15 out of 15 crab-eating monkey specimens and 1 out of 1 chimpanzee specimen. In contrast, HD8 did not react with RPMI 8226 (ATCC CCL-155), which is a B-cell strain in which HLA-DR is not expressed.

INDUSTRIAL APPLICABILITY

The present invention provides a preventive or therapeutic agent for diseases caused by HLA-DR-expressing cells, and more particularly, a molecule that is useful as a therapeutic agent for malignant tumors for patients having substantially almost all HLA-DR polymorphisms.

Further, the present invention provides a immunosuppressive agent for suppressing immunological activity associated with HLA-DR, and more particularly, a molecule that is useful as a therapeutic agent for rheumatisms.

All publications cited herein are incorporated herein by reference in their entirety. A person skilled in the art would easily understand that various modifications and changes are possible within the technical idea and the scope of the invention as described in the attached claims. The present invention is intended to include such modifications and changes.

The invention claimed is:

1. An antibody or an antigen-binding fragment that binds to HLA-DR and that is produced by the hybridoma HD8, deposited under accession number: FERM BP-7773.

2. An antibody or an antigen-binding fragment that binds to HLA-DR which comprises the heavy chain and light chain variable regions of an antibody produced by the hybridoma HD8, deposited under accession number: FERM BP-7773.

3. The antibody or an antigen-binding fragment thereof according to claim 2, wherein the antibody subclass is IgG.

4. The antibody or an antigen-binding fragment thereof according to claim 3, wherein IgG is IgG1.

5. The antibody or an antigen-binding fragment thereof according to claim 4, wherein an amino acid sequence in the constant region of the heavy chain is modified by substitution of amino acid residue 331 according to the EU numbering system with serine.

6. The antibody or an antigen-binding fragment thereof according to claim 3, wherein IgG is IgG2.

7. The antibody or an antigen-binding fragment thereof according to claim 6, wherein an amino acid sequence in the constant region of the heavy chain is modified by substitution of amino acid residue 331 according to the EU numbering system with serine.

8. The antibody or an antigen-binding fragment thereof according to claim 3, wherein IgG is IgG3.

9. The antibody or an antigen-binding fragment thereof according to claim 3, wherein IgG is IgG4.

10. The hybridoma HD8, deposited under accession number FERM BP-7773.

11. An antibody or an antigen-binding fragment that binds to HLA-DR and that comprises (i) a first amino acid sequence, in its heavy chain, consisting of the sequence from the glutamine in amino acid position 21 through the serine in amino acid position 152 of SEQ ID NO:21 and (ii) a second amino acid sequence, in its light chain, consisting of the sequence from the alanine in amino acid position 23 through the lysine in amino acid position 129 of SEQ ID NO:23.

12. The antibody or an antigen-binding fragment thereof according to claim 11, wherein the antibody subclass is IgG.

13. The antibody or an antigen-binding fragment thereof according to claim 12, wherein IgG is IgG1.

14. The antibody or an antigen-binding fragment thereof according to claim 13, wherein an amino acid sequence in the constant region of the heavy chain is modified by substitution of amino acid residue 331 according to the EU numbering system with serine.

15. The antibody or an antigen-binding fragment thereof according to claim 12, wherein IgG is IgG2.

16. The antibody or an antigen-binding fragment thereof according to claim 15, wherein an amino acid sequence in the constant region of the heavy chain is modified by substitution of amino acid residue 331 according to the EU numbering system with serine.

17. The antibody or an antigen-binding fragment thereof according to claim 12, wherein IgG is IgG3.

18. The antibody or an antigen-binding fragment thereof according to claim 12, wherein IgG is IgG4.

19. An antibody or an antigen-binding fragment that binds to HLA-DR and that comprises (i) a first amino acid sequence, in its heavy chain, that is encoded by a nucleic acid sequence consisting of the sequence from the cytosine in nucleotide position 101 through the adenosine in nucleotide position 496 of SEQ ID NO:20 and (ii) a second amino acid sequence, in its light chain, that is encoded by a nucleic acid sequence consisting of the sequence from the guanine in nucleotide position 100 through the adenosine in amino acid position 420 of SEQ ID NO:22.

20. The antibody HD8G1 Ser or an antigen-binding fragment thereof, which is the antibody HD8 having an IgG1 subclass and amino acid 331 in the constant region of the heavy chain according to the EU numbering system being substituted with Ser.

21. The antibody HD8G2 or an antigen-binding fragment thereof, which is the antibody HD8 having an IgG2 subclass and amino acid 331 in the constant region of the heavy chain according to the EU numbering system being substituted with Ser.

* * * * *

SEQUENCE LISTING

```
<160> NUMBER OF SEQ ID NOS: 147

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence:primer

<400> SEQUENCE: 1
ccggaattcc caccatggcc ataagtggag tccctgtg                             38

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence:primer

<400> SEQUENCE: 2
aaagcggccg ctcattacag aggcccctg cgttctgc                              38

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 3
ccggaattcc tggtcctgtc ctgttctcca gca                                  33

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence:primer

<400> SEQUENCE: 4
aaagcggccg ctcatcagct caggaatcct gttggctg                             38

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 5
ggtccgggag atcatgaggg tgtcctt                                         27
```

```
<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 6
gtgcacgccg ctggtcaggg cgcctg                                          26

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 7
ggtgccaggg ggaagaccga tgg                                             23

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 8
atatgtcgac ccagccctgg gattttcagg tgttttc                              37

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence:primer

<400> SEQUENCE: 9
atatgtcgac tggctgacca gggcagtcac cagag                                35

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 10
gatgggccct tggtgctagc tgaggagacg g                                    31

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 11
gttgaagctc tttgtgacgg gcgagc                                          26

<210> SEQ ID NO 12
<211> LENGTH: 26
<212> TYPE: DNA
<213> ORGANISM: Artificial Sequence
<220> FEATURE:
```

-continued

<223> OTHER INFORMATION: Description of Artificial Sequence:primer

<400> SEQUENCE: 12
tggcgggaag atgaagacag atggtg                                          26

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence:primer

<400> SEQUENCE: 13
atatagatct gctgctcagt taggacccag agggaacc                             38

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 14
atatagatct gggagtcaga cccactcagg acacagc                              37

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 15
aagacagatg gtgcagccac cgtacgtttg at                                   32

<210> SEQ ID NO 16
<211> LENGTH: 510
<212> TYPE: DNA
<213> ORGANISM: Homo sapiens

<400> SEQUENCE: 16
gtcgacccag ccctgggatt ttcaggtgtt ttcaggtgtt ttcatttggt gatcaggact      60
gaacagagag aactcaccat ggagtttggg ctgagctggc tttttcttgt ggctatttta    120
aaaggtgtcc agtgtgaggt gcaactgttg gagtctgggg gaggcttggt acagcctggg    180
gggtccctga gactctcctg tgcagcctct ggattcacct ttagcagcta tgccatgacc    240
tgggtccgcc aggctccagg aaggggctg gagtgggtct caggtattag tggtggtggt    300
gatagcacat actacgcaga ctccgtgaag ggccggttca ccatctccag agacaattcc    360
aagaacacgc tgtatctgca aatgaacagc ctgagagccg aggacacggc cgtatattac    420
tgtgcgagag atcatggttc ggggagttat tatccctact ggtttgacta ctggggccag    480
ggaaccctgg tcaccgtctc ctcagctagc                                    510

<210> SEQ ID NO 17
<211> LENGTH: 143
<212> TYPE: PRT
<213> ORGANISM: Homo sapiens

<400> SEQUENCE: 17

Met Glu Phe Gly Leu Ser Trp Leu Phe Leu Val Ala Ile Leu Lys Gly
1               5                   10                  15

-continued

```
Val Gln Cys Glu Val Gln Leu Leu Glu Ser Gly Gly Leu Val Gln
             20                  25                  30

Pro Gly Gly Ser Leu Arg Leu Ser Cys Ala Ala Ser Gly Phe Thr Phe
             35                  40                  45

Ser Ser Tyr Ala Met Thr Trp Val Arg Gln Ala Pro Gly Lys Gly Leu
             50                  55                  60

Glu Trp Val Ser Gly Ile Ser Gly Gly Asp Ser Thr Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
             100                 105                 110

Tyr Tyr Cys Ala Arg Asp His Gly Ser Gly Ser Tyr Tyr Pro Tyr Trp
             115                 120                 125

Phe Asp Tyr Trp Gly Gln Gly Thr Leu Val Thr Val Ser Ser Ala
             130                 135                 140
```

<210> SEQ ID NO 18
<211> LENGTH: 424
<212> TYPE: DNA
<213> ORGANISM: Homo sapiens

<400> SEQUENCE: 18

```
agatctgctg ctcagttagg acccagaggg aaccatggaa accccagcgc agcttctctt       60
cctcctgcta ctctggctcc cagataccac cggagaactt gtgttgacgc agtctccagg      120
caccctgtct ttgtctccag gggaaagagc caccctctcc tgcagggcca gtcagagtgt      180
tagcagccgc tacttagcct ggtaccagca gaaacctggc caggctccca ggctcctcat      240
ctatggtgca tccagcaggg ccactggcat cccagacagg ttcagtggca gtgggtctgg      300
gacagacttc actctcacca tcagcagact ggagcctgaa gattttgcag tgtattactg      360
tcagcagtat ggtagctcac cgctcacttt cggcggaggg accaaggtgg agatcaaacg      420
tacg                                                                  424
```

<210> SEQ ID NO 19
<211> LENGTH: 130
<212> TYPE: PRT
<213> ORGANISM: Homo sapiens

<400> SEQUENCE: 19

```
Met Glu Thr Pro Ala Gln Leu Leu Phe Leu Leu Leu Trp Leu Pro
  1               5                  10                  15

Asp Thr Thr Gly Glu Leu Val Leu Thr Gln Ser Pro Gly Thr Leu Ser
             20                  25                  30

Leu Ser Pro Gly Glu Arg Ala Thr Leu Ser Cys Arg Ala Ser Gln Ser
             35                  40                  45

Val Ser Ser Arg Tyr Leu Ala Trp Tyr Gln Gln Lys Pro Gly Gln Ala
             50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
             100                 105                 110

Gly Ser Ser Pro Leu Thr Phe Gly Gly Gly Thr Lys Val Glu Ile Lys
             115                 120                 125
```

<210> SEQ ID NO 20
<211> LENGTH: 502
<212> TYPE: DNA
<213> ORGANISM: Homo sapiens

<400> SEQUENCE: 20

```
gtcgactggc tgaccagggc agtcaccaga gctccagaca atgtctgtct ccttcctcat    60
cttcctgccc gtgctgggcc tcccatgggg tgtcctgtca caggttcagc tgcagcactc   120
aggtccagga ctggtgaagc cctcgcagac cctctcactc acctgtgcca tctccgggga   180
cagtgtctct agcaacagtg cttcttggaa ctggatcagg cagtccccat cgaggggcct   240
tgagtggctg ggaaggacat actacaggtc caagtggtat aatgattatg cagtatctgt   300
gaaaagtcga atagtcatca acccagacac atccaagaac cagttctccc tgcagctgaa   360
ctctgtgact cccgaggaca cggctgtgta ttactgtgcg agagaaaatt tctatggttc   420
ggagacttgt cataagaagt attactgcta cggtatggac gtctggggcc aagggaccac   480
ggtcaccgtc tcctcagcta gc                                            502
```

<210> SEQ ID NO 21
<211> LENGTH: 154
<212> TYPE: PRT
<213> ORGANISM: Homo sapiens

<400> SEQUENCE: 21

```
Met Ser Val Ser Phe Leu Ile Phe Leu Pro Val Leu Gly Leu Pro Trp
1               5                   10                  15
Gly Val Leu Ser Gln Val Gln Leu Gln His Ser Gly Pro Gly Leu Val
            20                  25                  30
Lys Pro Ser Gln Thr Leu Ser Leu Thr Cys Ala Ile Ser Gly Asp Ser
        35                  40                  45
Val Ser Ser Asn Ser Ala Ser Trp Asn Trp Ile Arg Gln Ser Pro Ser
    50                  55                  60
Arg Gly Leu Glu Trp Leu Gly Arg Thr Tyr Tyr Arg Ser Lys Trp Tyr
65                  70                  75                  80
Asn Asp Tyr Ala Val Ser Val Lys Ser Arg Ile Val Ile Asn Pro Asp
                85                  90                  95
Thr Ser Lys Asn Gln Phe Ser Leu Gln Leu Asn Ser Val Thr Pro Glu
            100                 105                 110
Asp Thr Ala Val Tyr Tyr Cys Ala Arg Glu Asn Phe Tyr Gly Ser Glu
        115                 120                 125
Thr Cys His Lys Lys Tyr Tyr Cys Tyr Gly Met Asp Val Trp Gly Gln
    130                 135                 140
Gly Thr Thr Val Thr Val Ser Ser Ala Ser
145                 150
```

<210> SEQ ID NO 22
<211> LENGTH: 426
<212> TYPE: DNA
<213> ORGANISM: Homo sapiens

<400> SEQUENCE: 22

```
agatctggga gtcagaccca ctcaggacac agcatggaca tgagggtccc cgctcagctc    60
ctggggcttc tgctgctctg gctcccaggt gccagatgtg ccatccagtt gacccagtct   120
```

```
ccatcctccc tgtctgcatc tgtaggagac agagtcacca tcacttgccg ggcaagtcag    180
ggcattagca gtgctttagc ctggtatcag cagaaaccag ggaaagctcc taaactcctg    240
atctatgatg cctccagttt ggaaagtggg gtcccatcaa ggttcagcgg cagtggatct    300
gggacagatt tcactctcac catcagcagc ctgcagcctg aagattttgc aacttattac    360
tgtcaacagt ttaatagttt cccgctcact ttcggcggag ggaccaaggt ggagatcaaa    420
cgtacg                                                               426
```

```
<210> SEQ ID NO 23
<211> LENGTH: 132
<212> TYPE: PRT
<213> ORGANISM: Homo sapiens

<400> SEQUENCE: 23

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Ala Leu Ala Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Phe Pro Leu Thr Phe Gly Gly Gly Thr Lys Val Glu Ile
        115                 120                 125

Lys Arg Thr Val
    130

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 24

Trp Asn Ser Gln Lys Asp Phe Leu Glu Asp Arg Arg Ala
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 25

Trp Asn Ser Gln Lys Asp Phe Leu Glu Arg Arg Arg Ala
1               5                   10

<210> SEQ ID NO 26
<211> LENGTH: 13
<212> TYPE: PRT
<213> ORGANISM: Artificial Sequence
```

```
<220> FEATURE:
<223> OTHER INFORMATION: Description of Artificial Sequence:peptide

<400> SEQUENCE: 26

Trp Asn Ser Gln Lys Asp Phe Leu Glu Asp Glu Arg Ala
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 27

Trp Asn Ser Gln Lys Asp Phe Leu Glu Gln Ala Arg Ala
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 28

Trp Asn Ser Gln Lys Asp Ile Leu Glu Asp Glu Arg Ala
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 29

Trp Asn Ser Gln Lys Asp Ile Leu Glu Gln Lys Arg Gly
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 30

Trp Asn Ser Gln Lys Asp Ile Leu Glu Asp Arg Arg Ala
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 31

Trp Asn Ser Gln Lys Asp Ile Leu Glu Asp Arg Arg Gly
1               5                   10

<210> SEQ ID NO 32
<211> LENGTH: 13
<212> TYPE: PRT
<213> ORGANISM: Artificial Sequence
<220> FEATURE:
```

```
<223> OTHER INFORMATION: Description of Artificial Sequence:peptide

<400> SEQUENCE: 32

Trp Asn Ser Gln Lys Asp Ile Leu Glu Asp Lys Arg Ala
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 33

Trp Asn Ser Gln Lys Asp Ile Leu Glu Gln Ala Arg Ala
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 34

Trp Asn Ser Gln Lys Asp Leu Leu Glu Gln Arg Arg Ala
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 35

Trp Asn Ser Gln Lys Asp Leu Leu Glu Gln Ala Arg Ala
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 36

Trp Asn Ser Gln Lys Asp Leu Leu Glu Gln Lys Arg Gly
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 37

Trp Asn Ser Gln Lys Asp Leu Leu Glu Asp Arg Arg Ala
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence:peptide
```

```
<400> SEQUENCE: 38

Trp Asn Ser Gln Lys Asp Leu Leu Glu Arg Arg Arg Ala
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 39

Trp Asn Ser Gln Lys Asp Leu Leu Glu Asp Glu Arg Ala
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 40

Trp Asn Ser Gln Lys Asp Ala Leu Glu Gln Arg Arg Ala
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 41

Trp Asn Ser Gln Lys Asp Leu Leu Glu Ala Arg Arg Ala
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 42

Trp Asn Ser Gln Lys Asp Leu Leu Glu Gln Ala Arg Ala
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 43

Trp Asn Ser Gln Lys Asp Leu Leu Glu Gln Arg Arg Gly
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence:peptide
```

```
<400> SEQUENCE: 44

Ala Asn Ser Gln Lys Asp Leu Leu Glu Gln Arg Arg Ala
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 45

Trp Ala Ser Gln Lys Asp Leu Leu Glu Gln Arg Arg Ala
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 46

Trp Asn Ala Gln Lys Asp Leu Leu Glu Gln Arg Arg Ala
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 47

Trp Asn Ser Ala Lys Asp Leu Leu Glu Gln Arg Arg Ala
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 48

Trp Asn Ser Gln Ala Asp Leu Leu Glu Gln Arg Arg Ala
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 49

Trp Asn Ser Gln Lys Ala Leu Leu Glu Gln Arg Arg Ala
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 50
```

```
Trp Asn Ser Gln Lys Asp Leu Leu Ala Gln Arg Arg Ala
1               5                   10
```

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 51

```
Trp Asn Ser Gln Lys Asp Leu Leu Glu Gln Arg Ala Ala
1               5                   10
```

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 52

```
Gly Asp Thr Arg Pro Arg Phe Leu Trp Gln Pro Lys Arg
1               5                   10
```

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 53

```
Thr Arg Pro Arg Phe Leu Trp Gln Pro Lys Arg Glu Cys
1               5                   10
```

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 54

```
Pro Arg Phe Leu Trp Gln Pro Lys Arg Glu Cys His Phe
1               5                   10
```

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 55

```
Phe Leu Trp Gln Pro Lys Arg Glu Cys His Phe Phe Asn
1               5                   10
```

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 56

```
Trp Gln Pro Lys Arg Glu Cys His Phe Phe Asn Gly Thr
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 57

Pro Lys Arg Glu Cys His Phe Phe Asn Gly Thr Glu Arg
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 58

Arg Glu Cys His Phe Phe Asn Gly Thr Glu Arg Val Arg
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 59

Cys His Phe Phe Asn Gly Thr Glu Arg Val Arg Phe Leu
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 60

Phe Phe Asn Gly Thr Glu Arg Val Arg Phe Leu Asp Arg
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 61

Asn Gly Thr Glu Arg Val Arg Phe Leu Asp Arg Tyr Phe
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 62

Thr Glu Arg Val Arg Phe Leu Asp Arg Tyr Phe Tyr Asn
```

-continued

```
1               5                   10
```

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 63

```
Arg Val Arg Phe Leu Asp Arg Tyr Phe Tyr Asn Gln Glu
1               5                   10
```

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 64

```
Arg Phe Leu Asp Arg Tyr Phe Tyr Asn Gln Glu Glu Ser
1               5                   10
```

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 65

```
Leu Asp Arg Tyr Phe Tyr Asn Gln Glu Glu Ser Val Arg
1               5                   10
```

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 66

```
Arg Tyr Phe Tyr Asn Gln Glu Glu Ser Val Arg Phe Asp
1               5                   10
```

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 67

```
Phe Tyr Asn Gln Glu Glu Ser Val Arg Phe Asp Ser Asp
1               5                   10
```

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 68

```
Asn Gln Glu Glu Ser Val Arg Phe Asp Ser Asp Val Gly
1               5                   10
```

```
<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 69

Glu Glu Ser Val Arg Phe Asp Ser Asp Val Gly Glu Phe
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 70

Ser Val Arg Phe Asp Ser Asp Val Gly Glu Phe Arg Ala
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 71

Arg Phe Asp Ser Asp Val Gly Glu Phe Arg Ala Val Thr
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 72

Asp Ser Asp Val Gly Glu Phe Arg Ala Val Thr Glu Leu
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 73

Asp Val Gly Glu Phe Arg Ala Val Thr Glu Leu Gly Arg
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 74

Gly Glu Phe Arg Ala Val Thr Glu Leu Gly Arg Pro Asp
1               5                   10
```

```
<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 75

Phe Arg Ala Val Thr Glu Leu Gly Arg Pro Asp Ala Glu
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 76

Ala Val Thr Glu Leu Gly Arg Pro Asp Ala Glu Tyr Trp
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 77

Thr Glu Leu Gly Arg Pro Asp Ala Glu Tyr Trp Asn Ser
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 78

Leu Gly Arg Pro Asp Ala Glu Tyr Trp Asn Ser Gln Lys
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 79

Arg Pro Asp Ala Glu Tyr Trp Asn Ser Gln Lys Asp Ile
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 80

Asp Ala Glu Tyr Trp Asn Ser Gln Lys Asp Ile Leu Glu
1               5                   10
```

```
<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 81

Glu Tyr Trp Asn Ser Gln Lys Asp Ile Leu Glu Gln Ala
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 82

Trp Asn Ser Gln Lys Asp Ile Leu Glu Gln Ala Arg Ala
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 83

Ser Gln Lys Asp Ile Leu Glu Gln Ala Arg Ala Ala Val
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 84

Lys Asp Ile Leu Glu Gln Ala Arg Ala Ala Val Asp Thr
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 85

Ile Leu Glu Gln Ala Arg Ala Ala Val Asp Thr Tyr Cys
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 86

Glu Gln Ala Arg Ala Ala Val Asp Thr Tyr Cys Arg His
1               5                   10

<210> SEQ ID NO 87
```

```
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 87

Ala Arg Ala Ala Val Asp Thr Tyr Cys Arg His Asn Tyr
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 88

Ala Ala Val Asp Thr Tyr Cys Arg His Asn Tyr Gly Val
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 89

Val Asp Thr Tyr Cys Arg His Asn Tyr Gly Val Val Glu
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 90

Thr Tyr Cys Arg His Asn Tyr Gly Val Val Glu Ser Phe
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 91

Cys Arg His Asn Tyr Gly Val Val Glu Ser Phe Thr Val
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 92

His Asn Tyr Gly Val Val Glu Ser Phe Thr Val Gln Arg
1               5                   10

<210> SEQ ID NO 93
<211> LENGTH: 13
```

<212> TYPE: PRT
<213> ORGANISM: Artificial Sequence
<220> FEATURE:
<223> OTHER INFORMATION: Description of Artificial Sequence:peptide

<400> SEQUENCE: 93

Tyr Gly Val Val Glu Ser Phe Thr Val Gln Arg Arg Val
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 94

Val Val Glu Ser Phe Thr Val Gln Arg Arg Val Gln Pro
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 95

Glu Ser Phe Thr Val Gln Arg Arg Val Gln Pro Lys Val
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 96

Phe Thr Val Gln Arg Arg Val Gln Pro Lys Val Thr Val
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 97

Val Gln Arg Arg Val Gln Pro Lys Val Thr Val Tyr Pro
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 98

Arg Arg Val Gln Pro Lys Val Thr Val Tyr Pro Ser Lys
1               5                   10

<210> SEQ ID NO 99
<211> LENGTH: 13
<212> TYPE: PRT

<213> ORGANISM: Artificial Sequence
<220> FEATURE:
<223> OTHER INFORMATION: Description of Artificial Sequence:peptide

<400> SEQUENCE: 99

Val Gln Pro Lys Val Thr Val Tyr Pro Ser Lys Thr Gln
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 100

Pro Lys Val Thr Val Tyr Pro Ser Lys Thr Gln Pro Leu
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 101

Val Thr Val Tyr Pro Ser Lys Thr Gln Pro Leu Gln His
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 102

Val Tyr Pro Ser Lys Thr Gln Pro Leu Gln His His Asn
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 103

Pro Ser Lys Thr Gln Pro Leu Gln His His Asn Leu Leu
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 104

Lys Thr Gln Pro Leu Gln His His Asn Leu Leu Val Cys
1               5                   10

<210> SEQ ID NO 105
<211> LENGTH: 13
<212> TYPE: PRT
<213> ORGANISM: Artificial Sequence

```
<220> FEATURE:
<223> OTHER INFORMATION: Description of Artificial Sequence:peptide

<400> SEQUENCE: 105

Gln Pro Leu Gln His His Asn Leu Leu Val Cys Ser Val
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 106

Leu Gln His His Asn Leu Leu Val Cys Ser Val Ser Gly
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 107

His His Asn Leu Leu Val Cys Ser Val Ser Gly Phe Tyr
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 108

Asn Leu Leu Val Cys Ser Val Ser Gly Phe Tyr Pro Gly
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 109

Leu Val Cys Ser Val Ser Gly Phe Tyr Pro Gly Ser Ile
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 110

Cys Ser Val Ser Gly Phe Tyr Pro Gly Ser Ile Glu Val
1               5                   10

<210> SEQ ID NO 111
<211> LENGTH: 13
<212> TYPE: PRT
<213> ORGANISM: Artificial Sequence
<220> FEATURE:
```

<223> OTHER INFORMATION: Description of Artificial Sequence:peptide

<400> SEQUENCE: 111

Val Ser Gly Phe Tyr Pro Gly Ser Ile Glu Val Arg Trp
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 112

Gly Phe Tyr Pro Gly Ser Ile Glu Val Arg Trp Phe Leu
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 113

Tyr Pro Gly Ser Ile Glu Val Arg Trp Phe Leu Asn Gly
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 114

Gly Ser Ile Glu Val Arg Trp Phe Leu Asn Gly Gln Glu
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 115

Ile Glu Val Arg Trp Phe Leu Asn Gly Gln Glu Glu Lys
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 116

Val Arg Trp Phe Leu Asn Gly Gln Glu Glu Lys Ala Gly
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 117

Trp Phe Leu Asn Gly Gln Glu Glu Lys Ala Gly Met Val
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 118

Leu Asn Gly Gln Glu Glu Lys Ala Gly Met Val Ser Thr
1               5                   10

<210> SEQ ID NO 119
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 119

Gly Gln Glu Glu Lys Ala Gly Met Val Ser Thr Gly Leu
1               5                   10

<210> SEQ ID NO 120
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 120

Glu Glu Lys Ala Gly Met Val Ser Thr Gly Leu Ile Gln
1               5                   10

<210> SEQ ID NO 121
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 121

Lys Ala Gly Met Val Ser Thr Gly Leu Ile Gln Asn Gly
1               5                   10

<210> SEQ ID NO 122
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 122

Gly Met Val Ser Thr Gly Leu Ile Gln Asn Gly Asp Trp
1               5                   10

<210> SEQ ID NO 123
<211> LENGTH: 13
<212> TYPE: PRT
<213> ORGANISM: Artificial Sequence
<220> FEATURE:
<223> OTHER INFORMATION: Description of Artificial Sequence:peptide

```
<400> SEQUENCE: 123

Val Ser Thr Gly Leu Ile Gln Asn Gly Asp Trp Thr Phe
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 124

Thr Gly Leu Ile Gln Asn Gly Asp Trp Thr Phe Gln Thr
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 125

Leu Ile Gln Asn Gly Asp Trp Thr Phe Gln Thr Leu Val
1               5                   10

<210> SEQ ID NO 126
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 126

Gln Asn Gly Asp Trp Thr Phe Gln Thr Leu Val Met Leu
1               5                   10

<210> SEQ ID NO 127
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 127

Gly Asp Trp Thr Phe Gln Thr Leu Val Met Leu Glu Thr
1               5                   10

<210> SEQ ID NO 128
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 128

Trp Thr Phe Gln Thr Leu Val Met Leu Glu Thr Val Pro
1               5                   10

<210> SEQ ID NO 129
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 129
```

```
Phe Gln Thr Leu Val Met Leu Glu Thr Val Pro Arg Ser
1               5                   10
```

<210> SEQ ID NO 130
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 130

```
Thr Leu Val Met Leu Glu Thr Val Pro Arg Ser Gly Glu
1               5                   10
```

<210> SEQ ID NO 131
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 131

```
Val Met Leu Glu Thr Val Pro Arg Ser Gly Glu Val Tyr
1               5                   10
```

<210> SEQ ID NO 132
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 132

```
Leu Glu Thr Val Pro Arg Ser Gly Glu Val Tyr Thr Cys
1               5                   10
```

<210> SEQ ID NO 133
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 133

```
Thr Val Pro Arg Ser Gly Glu Val Tyr Thr Cys Gln Val
1               5                   10
```

<210> SEQ ID NO 134
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 134

```
Pro Arg Ser Gly Glu Val Tyr Thr Cys Gln Val Glu His
1               5                   10
```

<210> SEQ ID NO 135
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 135

-continued

Ser Gly Glu Val Tyr Thr Cys Gln Val Glu His Pro Ser
1               5                   10

<210> SEQ ID NO 136
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 136

Glu Val Tyr Thr Cys Gln Val Glu His Pro Ser Val Thr
1               5                   10

<210> SEQ ID NO 137
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 137

Tyr Thr Cys Gln Val Glu His Pro Ser Val Thr Ser Pro
1               5                   10

<210> SEQ ID NO 138
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 138

Cys Gln Val Glu His Pro Ser Val Thr Ser Pro Leu Thr
1               5                   10

<210> SEQ ID NO 139
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 139

Val Glu His Pro Ser Val Thr Ser Pro Leu Thr Val Glu
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 140

His Pro Ser Val Thr Ser Pro Leu Thr Val Glu Trp Arg
1               5                   10

<210> SEQ ID NO 141
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 141

Ser Val Thr Ser Pro Leu Thr Val Glu Trp Arg Ala Arg

-continued

<210> SEQ ID NO 142
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 142

Thr Ser Pro Leu Thr Val Glu Trp Arg Ala Arg Ser Glu
1               5                   10

<210> SEQ ID NO 143
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 143

Pro Leu Thr Val Glu Trp Arg Ala Arg Ser Glu Ser Ala
1               5                   10

<210> SEQ ID NO 144
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 144

Thr Val Glu Trp Arg Ala Arg Ser Glu Ser Ala Gln Ser
1               5                   10

<210> SEQ ID NO 145
<211> LENGTH: 13
<212> TYPE: PRT
<213> ORGANISM: Artificial Sequence
<220> FEATURE:
<223> OTHER INFORMATION: Description of Artificial Sequence:peptide

<400> SEQUENCE: 145

Val Glu Trp Arg Ala Arg Ser Glu Ser Ala Gln Ser Lys
1               5                   10

<210> SEQ ID NO 146
<211> LENGTH: 801
<212> TYPE: DNA
<213> ORGANISM: Homo sapiens

<400> SEQUENCE: 146
atggtgtgtc tgaagctccc tggaggctcc tgcatgacag cgctgacagt gacactgatg    60
gtgctgagct ccccactggc tttgtctggg acacccgac cacgtttcct gtggcagcct   120
aagagggagt gtcatttctt caatgggacg gagcgggtgc ggttcctgga cagatacttc   180
tataaccagg aggagtccgt gcgcttcgac agcgacgtgg gggagttccg ggcggtgacg   240
gagctggggc ggcctgacgc tgagtactgg aacagccaga aggacatcct ggagcaggcg   300
cgggccgcgg tggacaccta ctgcagacac aactacgggg ttgtggagag cttcacagtg   360
cagcggcgag tccaacctaa ggtgactgta tatccttcaa agacccagcc cctgcagcac   420
cacaacctcc tggtctgctc tgtgagtggt ttctatccag gcagcattga agtcaggtgg   480
ttcctgaacg gccaggaaga gaaggctggg atggtgtcca caggcctgat ccagaatgga   540

```
gactggacct tccagaccct ggtgatgctg gaaacagttc ctcgaagtgg agaggtttac    600
acctgccaag tggagcaccc aagcgtgaca agccctctca cagtggaatg agagcacgg     660 tctgaatctg cacagagcaa gatgctgagt ggagtcgggg gctttgtgct gggcctgctc    720
ttccttgggg ccgggctgtt catctacttc aggaatcaga aggacactc tggacttcag     780 ccaacaggat tcctgagctg a                                              801
```

```
<210> SEQ ID NO 147
<211> LENGTH: 266
<212> TYPE: PRT
<213> ORGANISM: Homo sapiens

<400> SEQUENCE: 147
```

| | | | | | | | | | | | | | | | |
|---|---|---|---|---|---|---|---|---|---|---|---|---|---|---|---|
| Met | Val | Cys | Leu | Lys | Leu | Pro | Gly | Gly | Ser | Cys | Met | Thr | Ala | Leu | Thr |
| 1 | | | | 5 | | | | | 10 | | | | | 15 | |
| Val | Thr | Leu | Met | Val | Leu | Ser | Ser | Pro | Leu | Ala | Leu | Ser | Gly | Asp | Thr |
| | | | 20 | | | | | 25 | | | | | 30 | | |
| Arg | Pro | Arg | Phe | Leu | Trp | Gln | Pro | Lys | Arg | Glu | Cys | His | Phe | Phe | Asn |
| | | 35 | | | | | 40 | | | | | 45 | | | |
| Gly | Thr | Glu | Arg | Val | Arg | Phe | Leu | Asp | Arg | Tyr | Phe | Tyr | Asn | Gln | Glu |
| | 50 | | | | | 55 | | | | | 60 | | | | |
| Glu | Ser | Val | Arg | Phe | Asp | Ser | Asp | Val | Gly | Glu | Phe | Arg | Ala | Val | Thr |
| 65 | | | | | 70 | | | | | 75 | | | | | 80 |
| Glu | Leu | Gly | Arg | Pro | Asp | Ala | Glu | Tyr | Trp | Asn | Ser | Gln | Lys | Asp | Ile |
| | | | | 85 | | | | | 90 | | | | | 95 | |
| Leu | Glu | Gln | Ala | Arg | Ala | Ala | Val | Asp | Thr | Tyr | Cys | Arg | His | Asn | Tyr |
| | | | 100 | | | | | 105 | | | | | 110 | | |
| Gly | Val | Val | Glu | Ser | Phe | Thr | Val | Gln | Arg | Arg | Val | Gln | Pro | Lys | Val |
| | | | 115 | | | | | 120 | | | | | 125 | | |
| Thr | Val | Tyr | Pro | Ser | Lys | Thr | Gln | Pro | Leu | Gln | His | His | Asn | Leu | Leu |
| | 130 | | | | | 135 | | | | | 140 | | | | |
| Val | Cys | Ser | Val | Ser | Gly | Phe | Tyr | Pro | Gly | Ser | Ile | Glu | Val | Arg | Trp |
| 145 | | | | | 150 | | | | | 155 | | | | | 160 |
| Phe | Leu | Asn | Gly | Gln | Glu | Glu | Lys | Ala | Gly | Met | Val | Ser | Thr | Gly | Leu |
| | | | | 165 | | | | | 170 | | | | | 175 | |
| Ile | Gln | Asn | Gly | Asp | Trp | Thr | Phe | Gln | Thr | Leu | Val | Met | Leu | Glu | Thr |
| | | | 180 | | | | | 185 | | | | | 190 | | |
| Val | Pro | Arg | Ser | Gly | Glu | Val | Tyr | Thr | Cys | Gln | Val | Glu | His | Pro | Ser |
| | | 195 | | | | | 200 | | | | | 205 | | | |
| Val | Thr | Ser | Pro | Leu | Thr | Val | Glu | Trp | Arg | Ala | Arg | Ser | Glu | Ser | Ala |
| | 210 | | | | | 215 | | | | | 220 | | | | |
| Gln | Ser | Lys | Met | Leu | Ser | Gly | Val | Gly | Phe | Val | Leu | Gly | Leu | Leu | |
| 225 | | | | | 230 | | | | | 235 | | | | | 240 |
| Phe | Leu | Gly | Ala | Gly | Leu | Phe | Ile | Tyr | Phe | Arg | Asn | Gln | Lys | Gly | His |
| | | | | 245 | | | | | 250 | | | | | 255 | |
| Ser | Gly | Leu | Gln | Pro | Thr | Gly | Phe | Leu | Ser | | | | | | |
| | | | 260 | | | | | 265 | | | | | | | |